(12) United States Patent
Calvo

(10) Patent No.: US 12,029,300 B1
(45) Date of Patent: Jul. 9, 2024

(54) DEVICE, SYSTEM AND METHOD FOR STORING, PROCESSING AND DISPENSING HAIR BUILDING MATERIAL

(71) Applicant: Joseph J. Calvo, Miami, FL (US)

(72) Inventor: Joseph J. Calvo, Miami, FL (US)

(73) Assignee: INVENTZ, INC., Miami, FL (US)

( * ) Notice: Subject to any disclaimer, the term of this patent is extended or adjusted under 35 U.S.C. 154(b) by 1092 days.

(21) Appl. No.: 16/670,743

(22) Filed: Oct. 31, 2019

Related U.S. Application Data

(63) Continuation-in-part of application No. 16/399,605, filed on Apr. 30, 2019, which is a continuation-in-part of application No. 14/585,563, filed on Dec. 30, 2014, now Pat. No. 10,271,627.

(60) Provisional application No. 61/936,001, filed on Feb. 5, 2014.

(51) Int. Cl.
*A45D 24/22* (2006.01)
*A45D 24/10* (2006.01)
*A61K 8/02* (2006.01)
*A61K 8/04* (2006.01)
*A61Q 5/00* (2006.01)
*A45D 24/00* (2006.01)

(52) U.S. Cl.
CPC ............ *A45D 24/22* (2013.01); *A45D 24/10* (2013.01); *A61K 8/022* (2013.01); *A61K 8/042* (2013.01); *A61Q 5/00* (2013.01); *A45D 2024/002* (2013.01); *A45D 2200/10* (2013.01); *A61K 2800/87* (2013.01); *A61K 2800/88* (2013.01)

(58) Field of Classification Search
CPC .......... A45D 2019/006; A45D 2019/02; A45D 24/22; A45D 24/24; A45D 24/28; A45D 24/26
See application file for complete search history.

(56) References Cited

U.S. PATENT DOCUMENTS

| | | | |
|---|---|---|---|
| 25,585 | A | 4/1882 | Goodyear |
| 1,594,636 | A | 8/1926 | Smith |
| 1,818,281 | A | 8/1931 | Soss |

(Continued)

FOREIGN PATENT DOCUMENTS

| | | |
|---|---|---|
| GB | 191109638 | 2/1912 |
| KR | 20060127914 | 10/2007 |

(Continued)

*Primary Examiner* — Rachel R Steitz
*Assistant Examiner* — Brianne E Kalach
(74) *Attorney, Agent, or Firm* — Malloy & Malloy, PL; Jennie S. Malloy

(57) ABSTRACT

A device, system and method for treating the scalp hair of an individual including the storing, processing, and dispensing hair building material, wherein the device includes at one or more housings connected to a base and a plurality of bristle elements disposed in a flow receiving relation to hair building material contained within the different housings of the base. A vibratory force is exerted on the base, housings and/or hair building material contained therein to facilitate a con current dispensing of different portions of the hair building material in a manner which accomplishes and at least partial blending of the different portions of the hair building material in the area of a bristle portion of the base. Once blended the hair building material is distributed throughout intended portions of the hair of a user by the bristles.

32 Claims, 34 Drawing Sheets

(56) References Cited

U.S. PATENT DOCUMENTS

| | | |
|---|---|---|
| 2,383,967 A | 9/1945 | Hernon |
| 2,819,723 A | 5/1955 | Meyer |
| 2,737,190 A | 3/1956 | Magnusson et al. |
| 2,771,890 A | 11/1956 | Jaberg |
| 3,960,160 A | 6/1976 | Hogan |
| 4,121,602 A | 10/1978 | Young |
| 4,202,361 A | 5/1980 | Bills |
| 4,213,423 A | 7/1980 | Bryan et al. |
| 4,520,831 A | 6/1985 | Schumann et al. |
| 4,792,250 A | 12/1988 | Turner |
| 4,902,154 A | 2/1990 | Valenza |
| 5,054,504 A | 10/1991 | Winrow |
| 5,076,298 A | 12/1991 | Busch et al. |
| 5,119,838 A | 6/1992 | Nakazima |
| 5,215,106 A | 6/1993 | Choi |
| 5,241,974 A | 9/1993 | Tsai |
| 5,261,427 A | 11/1993 | Dolev |
| 5,622,192 A | 4/1997 | Chiou |
| 5,762,433 A | 6/1998 | Cary |
| 5,927,290 A | 7/1999 | Thiruppathi |
| 6,877,924 B1 | 4/2005 | Mears et al. |
| 6,962,158 B1 | 11/2005 | Anguelo |
| 7,261,108 B2 | 8/2007 | Dallianis et al. |
| 7,322,363 B1 | 1/2008 | Dillard |
| 7,465,114 B2 | 12/2008 | Kress et al. |
| 7,530,358 B2 * | 5/2009 | Elliott .................. A45D 19/012 132/270 |
| 7,814,917 B2 | 10/2010 | Hurwitz |
| 8,347,894 B1 * | 1/2013 | Stewart .................. A45D 24/28 132/114 |
| 8,777,132 B2 | 7/2014 | Isaacs |
| 10,271,627 B1 | 4/2019 | Calvo |
| 2003/0150126 A1 | 8/2003 | Chang et al. |
| 2003/0159306 A1 | 8/2003 | Yeung |
| 2005/0016559 A1 | 1/2005 | Saida et al. |
| 2006/0021627 A1 | 2/2006 | Lee |
| 2006/0042643 A1 | 3/2006 | Delan |
| 2008/0138138 A1 | 6/2008 | Gueret |
| 2008/0149124 A1 | 6/2008 | McKay |
| 2008/0202544 A1 | 8/2008 | Hurwitz |
| 2009/0025247 A1 | 1/2009 | Yde et al. |
| 2009/0101159 A1 | 4/2009 | Bonnafous |
| 2010/0186762 A1 | 7/2010 | Spagnuolo |
| 2011/0206445 A1 | 8/2011 | Hurwitz |
| 2011/0293680 A1 | 12/2011 | Jo |
| 2013/0048003 A1 | 2/2013 | Antons |
| 2013/0115183 A1 | 5/2013 | Ko |
| 2015/0059798 A1 | 3/2015 | Mazed |

FOREIGN PATENT DOCUMENTS

| | | |
|---|---|---|
| KR | 100768540 | 12/2007 |
| WO | WO2009015802 | 1/2011 |

* cited by examiner

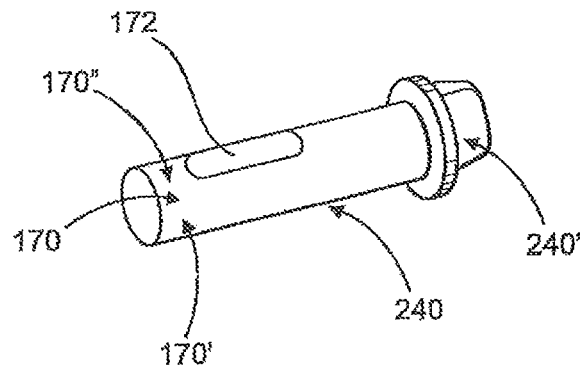
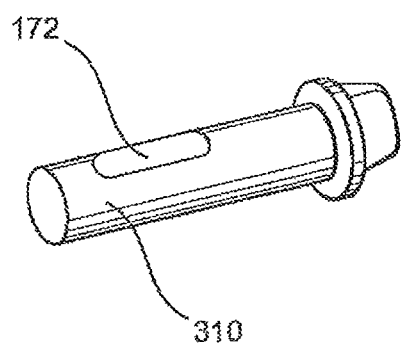
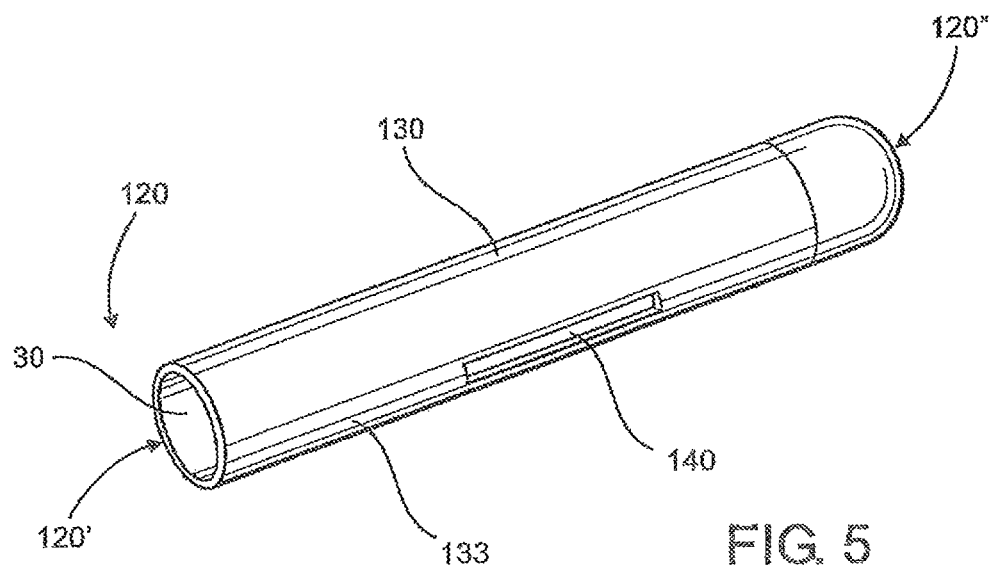

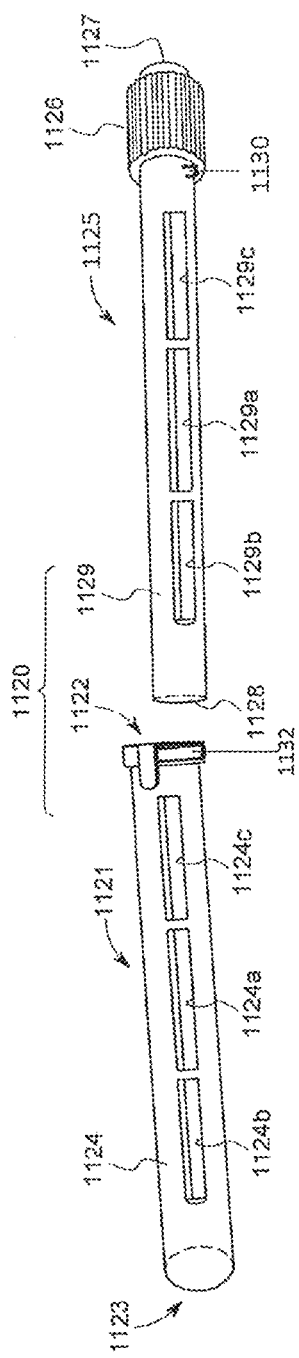
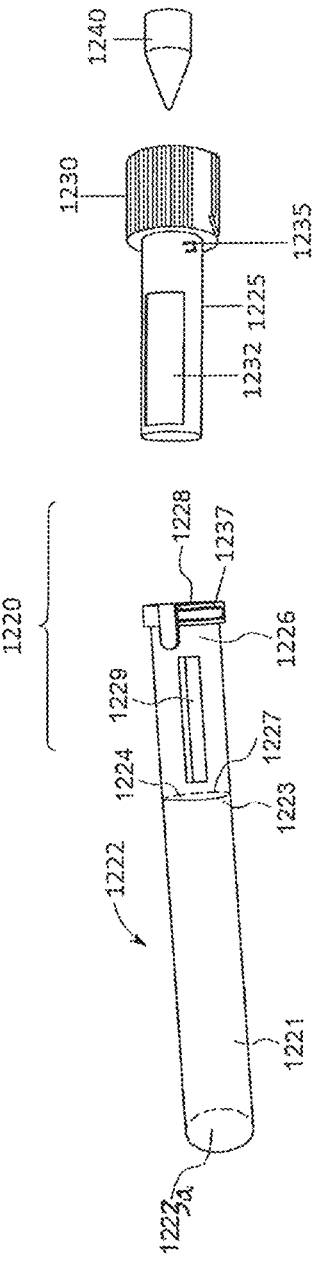
FIG. 16
FIG. 17

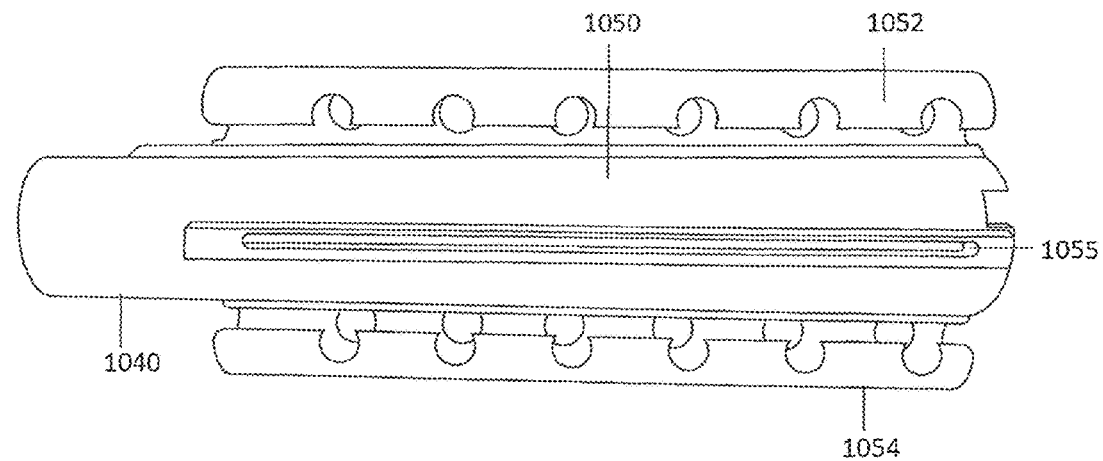
FIG 18-A
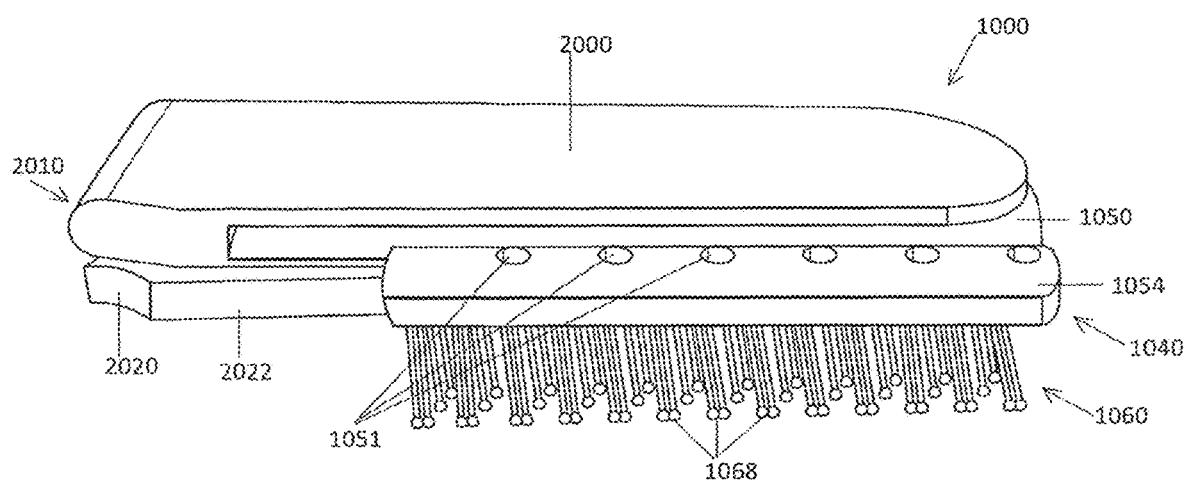
FIG. 18

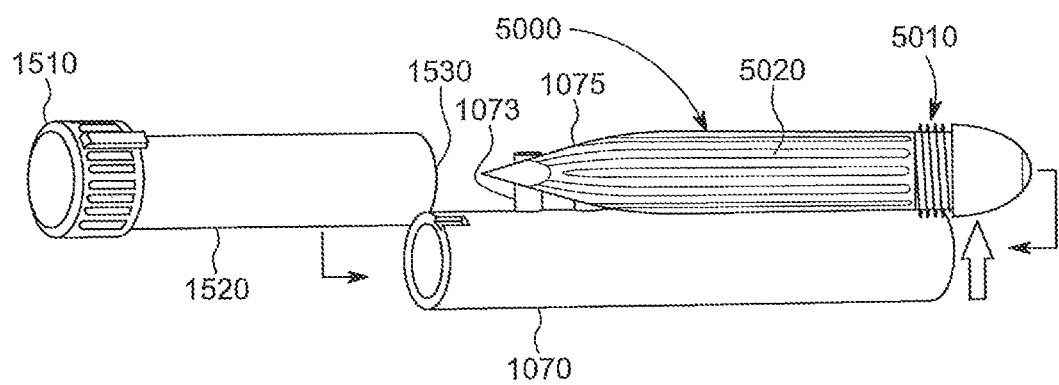
FIG. 22-C

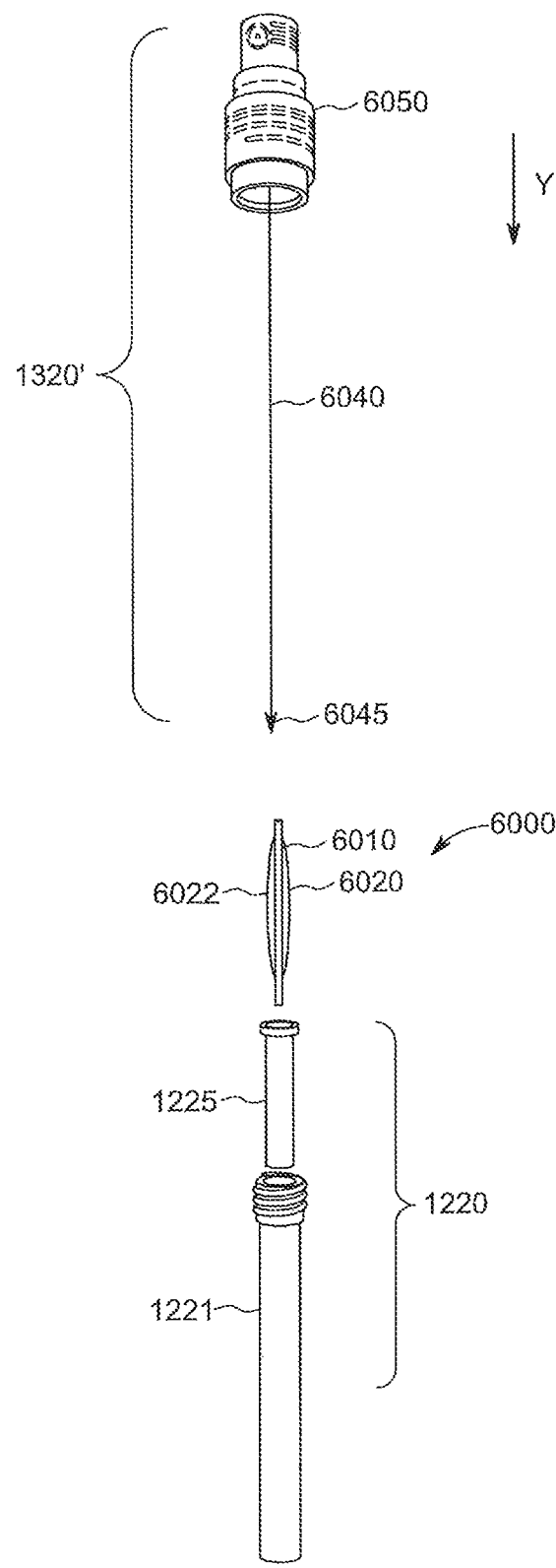
FIG. 22-D

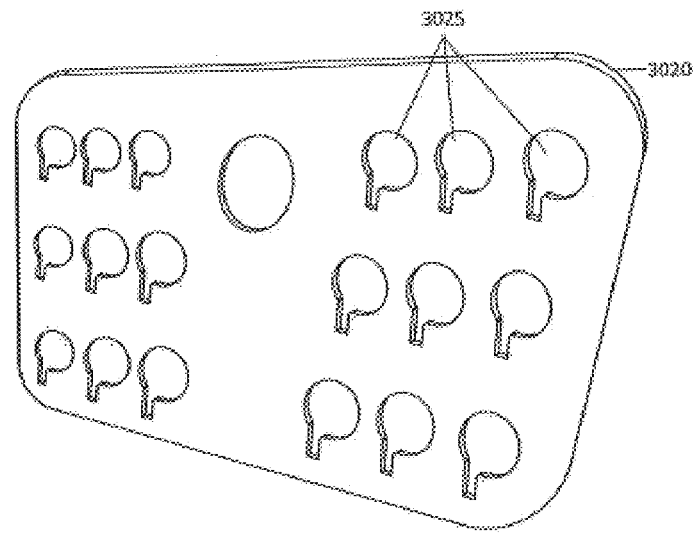
FIG. 26-A
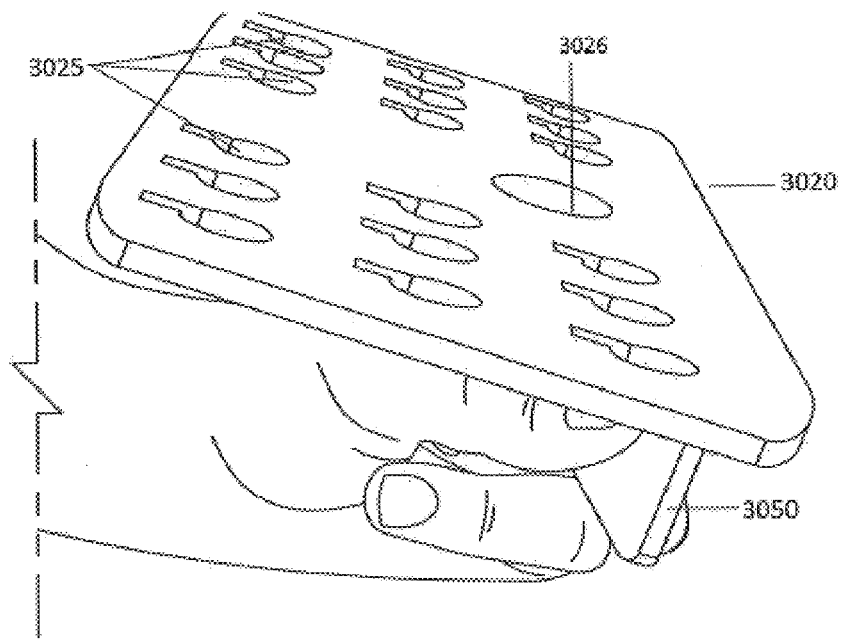
FIG. 27

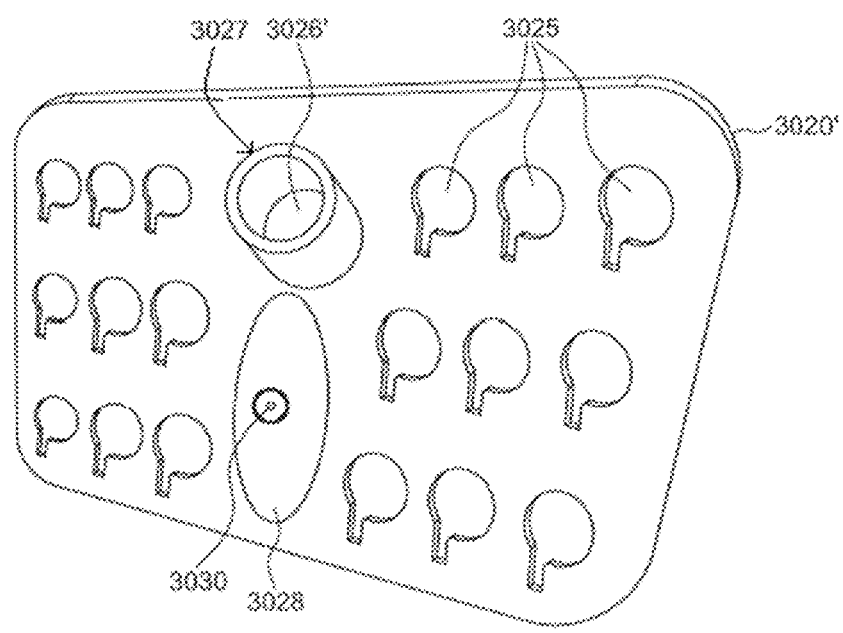
FIG. 26-B

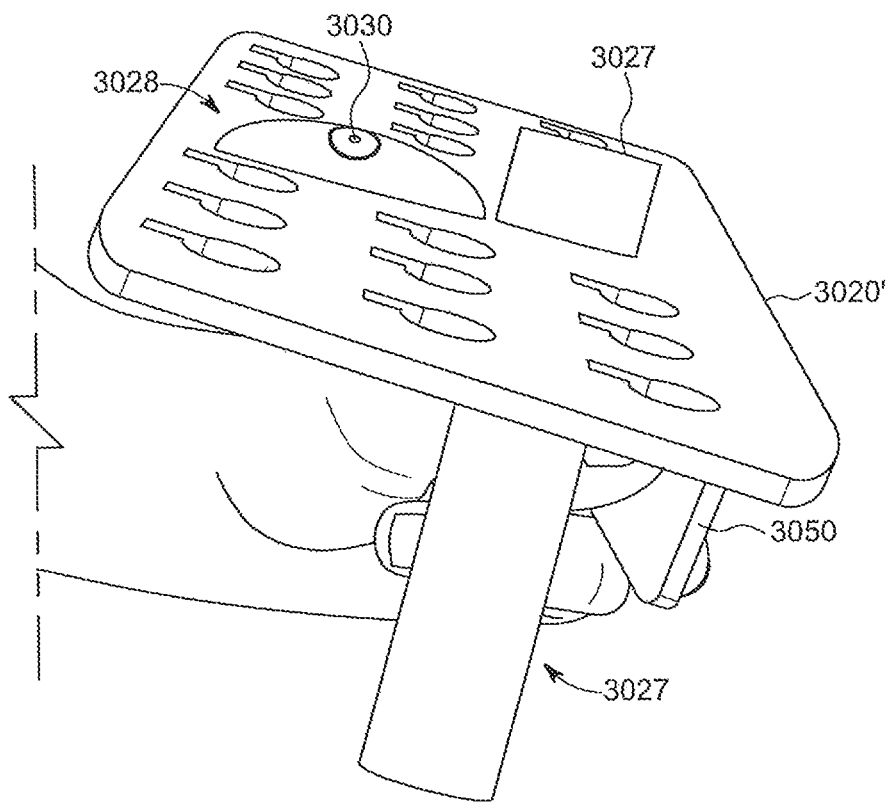
FIG. 27-A

DEVICE, SYSTEM AND METHOD FOR STORING, PROCESSING AND DISPENSING HAIR BUILDING MATERIAL

CLAIM OF PRIORITY

The present application is based on and a claim of priority is made under 35 U.S.C. Section 120 to a currently pending, U.S. "Continuation-in-Part" (CIP) patent application filed on Apr. 30, 2019 and having Ser. No. 16/399,605, which claimed priority to an earlier filed U.S. Non-Provisional patent application having Ser. No. 14/585,563 filed on Dec. 30, 2015, and now issued as U.S. Pat. No. 10,271,627 dated Apr. 30, 2019, which in turn, made a claim of priority under 35 U.S.C. Section 119(e) to a Provisional patent application filed in the U.S. Patent & Trademark Office on Feb. 5, 2014 and assigned Ser. No. 61/936,001, all of which are incorporated herein by reference in their entireties.

BACKGROUND OF THE INVENTION

Field of the Invention

The present invention is directed to a new and improved device for storing, processing, and dispensing hair building material, including or alternatively, other hair care products, and also to one or more improved cartridge assemblies for use with the device. The present invention is also directed to a foldable mirror assembly for use with the device, and in another embodiment, to a kit including the device, as well as a storage tray, one or more cartridge assemblies and other items. In addition, the present invention is directed to a system and method of treating scalp hair with hair building material(s) using the device.

Description of the Related Art

Alopecia is a medical term used when referring to a condition of thinning hair, partial hair loss or complete hair loss. In effect, nearly any form of hair loss can be considered as alopecia. With several contributing factors for hair loss and limited research available, comprehending hair loss can be intimidating to many. Equally daunting is finding solutions readily available for hair loss treatment. Certainly, hair loss is more common in men, albeit many women also suffer from various forms of alopecia. Alopecia in men and women, however, can vastly differ in areas of baldness or thinning as evidenced by certain patterns. In other words, female pattern baldness and male pattern baldness can differ based on condition and configuration of baldness. More specifically, the reason behind areas of thinning or balding in both men and women can vastly differ based on conditions related to genetic disposition or medical abnormalities. Of course, in both men and women, however, each strand of hair is retained in a cavity of the skin called a follicle. Hair loss occurs when the follicle miniaturizes over time. This means that the follicle prohibits further hair growth causing the affected strand of hair to result in being shorter and finer than normal. Consequently over time, the follicle inhibits further new hair growth, causing the hair strand to eventually fall out of the follicle, and perish indefinitely. As such, with no new hair growth in the follicle, and collectively more strands of hair thinning and falling out of affected follicles, a resulting pattern of baldness is evidenced over a period of time.

For this and other reasons, there are a few non-surgical and surgical solutions available in the market. These solutions strive to help reduce hair loss or the miniaturization of the hair follicles. However, many of them tend to work in only a certain percentage of men and women. This leaves a vast sample of hair loss sufferers without help. For instance, some of the known non-surgical solutions include, but are not limited to, topical solutions and consumable drugs. Both of these recognized options, however, do not indiscriminately provide results to everyone. To illustrate this more specifically, most topical solution products that contain Minoxidil, a known ingredient to reduce hair loss and in some cases regrow hair, require a strict regimen of application to the affected area. This essentially means that any lag, inconsistency or discontinuation in application to the affected area will more than likely result in major setback. This may include losing some or most of the regrown hair and/or continued loss of existing hair. Furthermore, this loss of hair can occur within a short amount of time, despite months of consistent use by the user. Additionally, Minoxidils also thought by some to have many adverse effects on humans and their pets. For example, Minoxidil can be highly toxic to some domestic pets, causing death following mere skin contact with the animal. In humans, Minoxidil contains side effects including burning, irritation of scalp or eye, itching, redness as well as risk of unwanted hair elsewhere on the person's body other than the treated area. Side effects can also be serious in some cases. Allergic reactions, such as rashes, hives, tightness in respiration, swelling of the mouth, dizziness and even tachycardia are thought to have occurred from Minoxidil, just to name a few. Other ingredients besides Minoxidil in many topical solutions such as alcohol or propylene glycol can also present their own issues. Dryness of the scalp resulting in embarrassing dermatitis and dandruff is one of them.

Similarly, consumable drugs that are taken orally require the following of strict routine. First, effective consumable drugs to treat hair loss require a prescription by a medical practitioner. This means that the hair loss sufferer cannot merely go to a local pharmacy and get the consumable drugs over the counter, but instead, typically requires an expensive visit to a medical practitioner. Next, any delay or discontinuation in daily usage can result in the reverse; hair loss can quickly follow within 30 to 60 days. Additionally, some of the consumable drugs taken orally are prone to cause harmful side effects. For instance, Finasteride, an active ingredient in most of the orally consumed drugs for hair loss prevention has been proven to significantly decrease testosterone levels in some men, who have regularly taken them. Moreover, what is alarming is that the drop in testosterone level in these cases, can last an average of 40 months, sometimes even after the user has discontinued their use. This can be a devastating experience for men, who are not only losing hair, but are now also suffering from unwanted side effects of low testosterone. Accordingly, many of the side effects due to consumable drugs for hair loss prevention seem to be more cumbersome than the problem of losing hair itself.

Another drawback often associated with consumable drugs taken orally is that they must be taken regularly, often for an average of 18 months before the user taking them regularly can see desired results. Furthermore, in some cases, the user may not see any results at all. In other words, the consumable drugs do not guarantee hair regrowth or hair loss prevention for everyone. This means that the user may regularly use the drugs, yet not experience any benefits of reduction in hair loss. As a result, the person could have possibly spent hundreds, if not thousands of dollars on these consumable drugs, only to realize that the results are not guaranteed.

Comparatively, there are other alternatives to treat hair loss. These include surgical solutions, where the person experiences minimally invasive surgery to treat hair loss. More specifically, the minimally invasive procedure may require transplanting each strand of hair from a donation area, such as where hair growth is dominant, to a treatment area, where the hair loss is evident. The surgical solutions, in most cases, however, are expensive and generally not covered by insurance companies. For example, the average cost of a hair transplant by minimally invasive surgery can range anywhere from $7,000 to $15,000 or even more. These numbers can be even higher depending on the locality, experience and skill set of the surgeon. Furthermore, since many insurance companies do not cover such type of cosmetic surgeries, more often than not, the patient has to pay the expense of a hair transplant surgery from personal funds.

Meanwhile, the minimally invasive surgeries to treat hair loss are also time consuming. They require a lot of time and commitment on the part of the patient. For instance, hair transplant surgeries can last for hours based on the fact that each strand of hair has to be taken from the donation area and replaced in the affected area. The hair transplant surgery also requires a lot of follow-up time. For example, patients of hair transplant surgeries are succumbed to several time consuming follow-up visits with the surgeon, sometimes even months after the surgery has been completed. Many surgeons also require their hair transplant patients to follow-up regularly due to the possible inconsistency in the growth of follicles, given that new hair was transplanted only in some follicles. Furthermore, most of the surgical procedures are not aesthetically pleasing. For example, surgical procedures can leave an unpleasant scar on the person's head, usually in the donation area, where the surgeon has removed the scalp and hair. This means, that the patient has to leave his hair at a particular length, so that the scar can remain hidden from public eye.

Moreover, as with most other solutions, there are no guarantees in hair transplant surgeries. For instance, a hair loss patient with a larger balding area and smaller donating area from where hair will be taken to achieve the transplant, may not yield a favorable aesthetic gratification as a patient who has a smaller balding area and a larger donating area, who achieves a fuller hair look from the transplant. Therefore, in certain procedures, the hair loss solution due to a transplant may appear to be even worse than the original condition.

Another known viable alternative to treat hair loss is wearing a hair wig or toupee. These too, however, have detrimental results. For wearers, there is a constant fear of discovery, as it can be difficult to admit that they are wearing a wig or toupee. Furthermore, despite the quality of wigs ranging from synthetic to human hair, there is no guarantee that wigs or toupees will go completely undetected by the probing eyes of the public. Correspondingly, quality hair wigs or toupees made of real human hair are highly expensive and hard to find. An average cost of a human hair wig can be hundreds, if not thousands of dollars. Additionally, hair wigs and toupees also require a great detail of maintenance. Wearing a wig or toupee tends to call for constant upkeep and can be a time absorbing ordeal that requires frequent retightening, washing, brushing and cleaning. Moreover, because some wigs or toupees require a vacuum fit on the hair scalp to prevent bacteria, and a non-vacuum environment can breed bacteria on the exfoliated skin, increasing excess sebum and causing undesirable odor on the scalp. Clearly, there is an exorbitant amount of commitment and expense required in both the known non-surgical and surgical methods currently in the market, without any guarantee of satisfactory results.

Fortunately, technology has improved and thinning hair or hair loss is no longer a niche market confined only to the surgical and non-surgical solutions aforementioned. This is helpful because given the growing public use and acceptance of various social media, hair loss sufferers are ever more cognizant of their appearance and condition. Accordingly, the cosmetic industry directed to hair loss is no longer focusing only on topical solutions, drugs taken orally or surgical transplants as viable alternatives, and as a result, some new hair loss solutions are now becoming available. Amidst this, and for reasons already noted herein, hair loss victims are demanding a solution that requires little commitment, low cost and negligible distress. Furthermore, there is a demand that the solution be elegant and aesthetically appealing, without yielding an artificial look, especially as many hair loss sufferers are already conscious about their existing hair loss condition. Additionally, many hair loss sufferers are seeking solutions that are free from harmful side effects, which do not cost a lot of money or require an inordinate amount of time to yield results, and that do not prohibit aesthetic pleasure.

One technology that has gained notoriety in the cosmetic industry for hair loss prevention is providing hair loss victims with hair building materials, such as but not limited to hair building fibers. Treating hair loss with hair building fibers is increasingly becoming a preferred method of concealing hair loss because of the relatively small time commitment involved. For instance, hair building fibers can be applied once daily, and can be easily washed off. Hair building fibers also do not require much time during application. They can be applied anytime of the day or night with little to no effort and care. Furthermore, hair building fibers easily blend in with the person's natural hair, producing an authentic and fuller look. The pricing of hair building fibers also make them appealing. For instance, hair building fibers are relatively cheap compared to other expensive non-surgical and surgical solutions. Altogether, they are designed to conceal hair loss for people with various forms of baldness patterns, including both men and women. They come in different shades, colors and textures. They also blend in with the user's natural hair and almost seamlessly give a much sought after fuller, natural look. Hair building fibers are also proven to be highly durable. This is primarily due to the technology and ingredients involved. For instance, hair building fibers can be worn all day, and often even for several days, depending on the rigor and format of activities engaged by the user. All things considered, the key to the durable characteristics of hair building fibers is that they bind to the hair with an electrostatic charge created by a hair applicator, often by electrical and mechanical means. Unfortunately, the charge does not last long in many cases due to sweat and atmospheric conditions, and in some cases, this may cause the fibers to fall and clog the scalp pores, and has the potential to result in adverse skin conditions.

Given such issues, it would be ideal if a device were developed that were capable of storing and processing certain components or ingredients used as hair building materials in separate chambers, such as hair fibers and/or other hair care products. It would also be ideal if any such device were developed that were also capable of combining certain hair building materials in an advantageous way upon the device's being picked up and used by a person, so that as the person dispenses the hair building materials onto his or her scalp, these materials are applied to the person's hair both evenly and in as natural a way as possible, and so as to be long lasting, while offering the user an appearance similar to or equally as good as those devices that rely on an electrostatic charge. That is to say, there is a need in the market for a hair applicator that can store and dispense hair building materials containing a beneficial blend of ingredients, as well as potentially other types of hair care products, and that can effectively be used by anyone suffering from hair loss to achieve a satisfying result in appearance that is also relatively long lasting in terms of daily use.

SUMMARY OF THE INVENTION

This invention is intended to present a solution to these and other needs which remain in the relevant field of art. As such, the present invention can have various embodiments, but in one embodiment, is directed to a device, which can also be referred to as a Processor Dispensing Unit, that allows a user to store, process and dispense hair building material, and if desired, other hair care products. More specifically, the inventive device can store, process, and dispense a hair building material or a combination of hair building materials. This can include but is not limited to the dispensing of hair-like strands, hair like fibers, and also coloring material(s) if desired, onto a user's hair and/or scalp area, in an amount sufficient to result in a smooth, natural-looking blend with the natural hair. More in particular, the hair applicator device of the present invention is structured to separately store and process certain hair building materials, including but not limited to, a combination of a liquid and/or gel like composition on the one hand, and one or more dry powders on the other, and then to dispense these materials substantially simultaneously for blending and/or delivery of the blended hair building materials directly onto to the hair and/or scalp of the user. This can be accomplished with little effort, all while the user is brushing his or her hair with the inventive device. In this regard, the device can be utilized on a variety of different hair types, textures and colors, and in combination with a variety of hair building ingredients, and in some cases if desired, other hair care products.

As will be described in greater detail herein, in at least one embodiment the device of the present invention comprises a central housing that is constructed of a generally rigid material. The central housing has a hollow interior first chamber and is connected to a base. In at least one embodiment, the base and the central housing are formed as one integral unit. Additionally, the central housing of the device is sized, structured and configured to receive, within its hollow interior first chamber, a cartridge or a cartridge assembly containing hair building material. As will be explained in greater detail herein, the cartridge assembly may comprise a first cartridge assembly, and in some embodiments, a second cartridge assembly. Furthermore, in one embodiment, the base is structured to include or be connected to a handle having at least one actuator, which can be configured to have at least one power switch or take off. The base can also be made of a generally rigid material and configured, as noted above, to include or be connected with a handle, helping the user to effectively grasp and/or grip the device of the present invention as needed or required. The device can also include a motor operably connected to the power switch or take off and a power supply source. In some embodiments, the motor is sized and configured to be housed within the handle, and can include a plurality of gears fitted inside the interior portion or portions thereof, as well as suitable electrical wiring connecting the motor to the power source and/or power switch. The power supply source is also preferably disposed within the interior portion of the base and/or handle. Additionally, the power supply source can generally function on a low power voltage, preferably with the use of a battery as its primary power source. In some embodiments, however, the battery can be a super battery or a rechargeable battery. In contrast, the device can also be operable with other forms of power supply sources, including but not limited to electric power supplies and/or may be charged or recharged by a wireless charger or any other kind of electrical charger. Alternatively, the device can also function manually, requiring no power source. The base can be sealed in some embodiments to prevent its interior portion from any potential water damage or other user related damages.

Furthermore, the central housing of the device may be connected to the base, or in some embodiments, it may be formed to be integral with the base. In an alternative preferred embodiment, however, the central housing is structured to be removably attached to the base. More specifically, the present invention allows a user to selectively detach the central housing from the base, or alternatively, the base including the central housing can be selectively detached from the handle. This selective detachment and re-attachment of the housing to the base and/or the base including the housing to and from the handle, will be further explained in greater detail below, including the many advantages it offers of allowing the user to carry a portable device for dispensing hair building material(s) as needed, while on the go.

In addition to this, the central housing also has an exterior surface with a plurality of bristle elements attached thereto. The plurality of bristle elements can be detachable or permanently affixed to the exterior surface of the central housing or in some embodiments, of the base. More specifically, the hair applicator device of the present invention can, in some embodiments, be configured to allow the plurality of bristle elements to be completely detached from the base so as to allow the user to use the device as a pocket portable for "on the go" spot treatment of the hair. To illustrate this, the plurality of bristle elements can be detached from the base to store the device in a portable manner, allowing the user to spot treat the affected areas as and when needed. Additionally, the plurality of bristle elements can also be interchangeable. This allows the user to use various types of bristle elements, depending on the texture or style of the user's hair. Furthermore, each of the plurality of bristle elements can have a ball tip on each of their respective ends. As such, the ball tips of the plurality of bristles can be structured to create a mechanical friction on the user's hair scalp due to their movement by vibration in the embodiment wherein the hair applicator device includes a motor, and also by the user's manual movement of the bristles across his or her hair and scalp. This mechanical friction contributes to the smooth attachment of the hair building material onto the user's scalp and with greater ease.

Still referring to the central housing of the inventive hair applicator device, the first interior hollow chamber thereof may be defined by a first open end and a closed second end, although other embodiments are possible, such as but not limited to an open first end and an open second end. In addition, the central housing includes a plurality of pathways formed within it and disposed in a fluid flow connection between the hollow interior first chamber and the exposed surface of the central housing. For instance, a first supply of hair building material contained within a cartridge disposed within the hollow interior first chamber may take the form of a "wet" material such as a gel-like fluid, and through manipulation of the cartridge, and alignment of apertures formed therein, this wet or gel like fluid can flow freely from cartridge and the interior chamber of the central housing, out through the plurality of pathways and to the exterior surface of the central housing and/or base, and then onto the user's scalp hair, under the force of gravity, but preferably also a vibratory motion, and through the application of the bristle elements to the user's scalp and/or hair. As such, it is preferred that the plurality of pathways are located in between the plurality of bristle elements, so as to structurally coexist together with openings formed on the exterior surface of the central housing.

Furthermore, the inventive hair applicator device comprises a movable member. The movable member is preferably structured as part of and in association with the handle that is movably disposed within the hollow interior first chamber of the central housing to provide vibratory motion. At least a majority of the length of the movable member, if not the full length of it, is enclosed within the hollow interior first chamber of the central housing. In this regard, the movable member is coupled to the central housing or removably connected to the central housing and/or the base associated therewith, so as to be movable within at least a portion of the hollow interior first chamber. Correspondingly, the movable member may be powered by the power supply source disposed in the base or handle. The power from the power supply source to the movable member enables the movable member to sonically oscillate and/or vibrate within the hollow interior first chamber of the central housing. As such, the movable member vibrates and/or oscillates at a frequency that is sufficient to create a mechanical shear stress in the hair building material, when the movable member is introduced to it. The stress due to the vibrating movable member results in the hair building material, such as the first supply of a wet hair building material, decreasing its viscosity, thereby causing it to at least partially liquefy from its original gel-like form. The liquefaction of the hair building material facilitates its release or allows it to ooze and/or be "squeezed out" from its containment, meaning within the cartridge assembly.

Additionally, in one or more embodiments, the movable member may be structured to have an external surface configuration that is stepped, so as to have a lowest portion with a widest outer diametric dimension than an adjacent portion, which in turn has a wider outer diametric dimension that an uppermost or top portion. This stepped configuration, which effectively tapers from a wide to narrow diametric dimension from the lower portion, adjacent to or as associated with the handle, to the top portion of the movable member, allows a user to operably connect the handle to the base or central housing, and further, with the movable member being structured so as to be received within the central housing. Given this stepped external configuration, wherein the peripheral portions adjacent to the lowest portion of the movable member are matingly secured, such as by a friction fit, with the open first end of the central housing (formed so as to be considered a receiving member) and/or base, the movable member and/or handle is securely attached and ensures a secure fit to the central housing and base. In the preferred embodiment, the secure connection of the movable member into the lower end or receiving member associated with the central housing and base, allows these components to also vibrate and oscillate when the movable member is in operational use.

The inventive hair applicator device further comprises at least one cartridge assembly, cartridge, or a canister. In one or more embodiments, however, the device can include a plurality of cartridges, such as a first cartridge assembly and a second cartridge assembly and possibly others, as described further below. Each of the cartridge assemblies contains at least a portion of the hair building material or in some cases, another hair care product. In a preferred embodiment, the first cartridge assembly containing a hair building material is sized, structured and configured to be received within the hollow interior of the central housing of the base, or the first chamber thereof. In another embodiment, the inventive device can include one cartridge assembly having dual interior chambers, so that a different portion of hair building material can be stored within each of the interior chambers on a single cartridge assembly, until it is desired to dispense the same. In a further embodiment of the at least one cartridge assembly having dual interior chambers, one of the interior chambers may be structured and configured to receive a smaller sized cartridge therein.

More specifically, and while the cartridge assembly could easily assume other embodiments within the spirit and scope of this invention, the first cartridge assembly will preferably have an open end and a penetrable closed end that is structured to receive the movable member, upon application of a suitable predetermined force by the user. For instance, the movable member is structured to penetrate through the penetrable closed end of the first cartridge assembly, when the user applies the suitable amount of force. To further illustrate this, a suitable force is applied by the user in directing the first cartridge assembly into and fully inserting it within the hollow interior first chamber of the central housing, with the penetrable closed end of the first cartridge assembly directly facing the movable member disposed inside the hollow interior first chamber of the central housing. As such, the first cartridge assembly containing the hair building material is inserted into the hollow, interior first chamber of the central housing. Given this, it is important to note that the outer diametric dimensions of the first cartridge assembly are preferably close to but slightly smaller than the inner diametric dimensions of the central housing and its hollow interior chamber, so as to create a frictional fit between them. The frictional fit ensures that the first cartridge assembly will remain in place during use, despite the vibrational movement of the movable member, and also allows for the first cartridge assembly to be removed from the hollow interior first chamber of central housing, when that is desired. To further illustrate, as force is continued to be applied on the first cartridge assembly during its insertion into the housing, the penetrable closed end establishes contact with the movable member. As such, the movable member is sized, structured and configured to penetrate within the first cartridge assembly. As the insertion of the first cartridge continues and the contact signifies, the movable member penetrates so as to intrude through the penetrable, closed end of the cartridge, becoming exposed to and contacting the hair building material contained therein. As a result, the movable member is exposed directly to the hair building material contained in the first cartridge assembly. Additionally, the force applied to the first cartridge assembly should be sufficient to frictionally secure a majority portion of the first cartridge assembly within the hollow interior first chamber of the central housing, so as to ensure that the first cartridge assembly is removably affixed on the movable member when in operational use.

Furthermore, the first cartridge assembly has an exterior surface extending between the two ends thereof, and further, includes at least one slit communicating with the interior of the cartridge assembly containing the hair building material. This slit, or alternatively a plurality of slits or other openings, can be aligned with the plurality of pathways disposed on the central housing, as for instance, by inserting the first cartridge assembly into the hollow interior first chamber of the central housing, and rotationally moving it there-within, so as to align the slit in the same direction of fluid flow travel with the plurality of pathways. So, once the first cartridge assembly is rotated into the preferred alignment, the hair building material contained in the cartridge, once liquefied, is ready to freely flow out through the slit of the first cartridge assembly, and to pass through the plurality of pathways on the exterior surface of the outer wall of the central housing and out, onto the plurality of bristles.

The device of the present invention preferably also comprises a second housing connected to the central housing at an upper surface thereof. This may also be referred to as an auxiliary housing which in some embodiments, can be removably connected to the base associated with the central housing or chamber. The second housing has an exterior surface with a plurality of openings that are in a fluid flow connection with the plurality of bristle elements. Accordingly, as the hair building material contained in the second cartridge assembly, which is inserted in the second housing, flows through the plurality of openings, it is directed to simultaneously blend with the hair building material from the first cartridge assembly contained in the central housing and flowing through the plurality of pathways. More specifically, the second cartridge assembly includes an outer wall with an exterior surface extending the length thereof. The outer wall of the second cartridge assembly includes and is structured to define at least one incision or alternatively other opening(s), extending completely through and between the exterior surface and an interior surface thereof, so as to allow the one or more ingredients of the hair building material carried inside the second cartridge assembly to freely flow out of and through the incision.

Given this, the second cartridge assembly containing additional hair building material (such as, for example, another type of hair building material or a hair coloring material) is inserted into a hollow interior second chamber of the second housing. As such, the hollow interior second chamber of the second housing is sized, structured and configured to receive and secure the second cartridge assembly there-within. Accordingly, the user inserts the second cartridge assembly within the hollow interior second chamber of the second housing and rotationally aligns the incision on the exterior surface of the second cartridge assembly with the plurality of openings of the second housing so as to ensure that the incision on the second cartridge assembly is in a fluid flow connection with the plurality of openings disposed on the second housing. As a result of this, the additional hair building material contained in the second cartridge assembly is able to flow relatively freely through and out from the incision of the second cartridge assembly, passing through the plurality of openings disposed on the second housing and out, onto to the bristle assembly and/or user's hair or scalp.

Furthermore, the second cartridge assembly is preferably also structured to be frictionally fit within the hollow interior second chamber of the second housing. As such, the outer diametric dimensions of the second cartridge assembly are ideally also about the same but slightly smaller than the inner diametric dimensions of the second housing, so as to create a frictional fit, and as such, secure at least a portion of the second cartridge assembly within the hollow interior second chamber of the second housing. Moving forward, as the force is continued to be applied on the second cartridge assembly as it is inserted into the second housing, the frictional fit secures a majority portion of the second cartridge assembly within the hollow interior second chamber of the second housing, so as to ensure that the second cartridge assembly is operationally in use and yet also removably affixed therein to allow for being replaced with another cartridge assembly having a fresh supply of hair building material or for the refilling of the cartridge assembly.

It will be appreciated that in a preferred embodiment, one or more additional types of hair building material can be contained in the second cartridge assembly that is inserted into the second housing, and that once the incision thereof is aligned with the plurality of openings formed in the second housing, this hair building material can flow through and out from the incision, pass through the plurality of openings, and blend with the other type of hair building material contained in the first cartridge assembly, which flows through the plurality of pathways, to dispense directly on to the bristle assembly and/or user's hair or scalp, with the plurality of bristle elements contacting, engaging or interacting with the user's hair and/or scalp. While not necessary in all cases, this should occur concurrently as the user brushes the inventive device directly on the user's hair scalp. Also, in a most preferred embodiment, hair building materials which are dry, whether in the form of a powder, granular mixture and/or fiber like strands will be carried individually, i.e., separately within an individual chamber or in a separate cartridge assembly.

The inventive hair applicator can include, in another preferred embodiment, a third housing. In this embodiment, the third housing will preferably be connected to the central housing at an upper surface thereof, and similar to central housing, is formed of a rigid material so as to have a first closed end, a second open end and a hollow interior third chamber. As such, the hollow interior third chamber is sized, structured and configured to receive a cartridge assembly, which may be identical to the second cartridge assembly. In some embodiment, however, the second cartridge assembly may take the form of an atomizer or pump sprayer insertable in and removable from the third housing, when it is desired to dispense the material(s) or product carried within it. Furthermore, the third housing also comprises an outer body wall between said first and second ends with a plurality of slots formed within it. As such, the third housing is also in a fluid flow connection with the plurality of bristle elements.

In this regard, additional ingredients used as hair building material can be contained in another or separate second cartridge assembly and can freely flow through and out from the incision formed therein, and also pass through the plurality of slots, and consequently, on to the user's hair scalp to blend with one or more ingredients dispensed from the first cartridge assembly located within the central housing and the other second cartridge assembly located within the second housing. In other words, in one preferred embodiment and while not always necessary, one or more ingredients of the hair building material contained in a cartridge assembly in the third housing flows through the plurality of slots, to simultaneously be blended on the user's hair and scalp, with one or more ingredients of the hair building material contained in the second cartridge assembly in the second housing which flow through the plurality of openings, and to collectively further blend with one or more ingredients contained in the first cartridge assembly inserted in the central housing flowing through the plurality of pathways. The blending and processing of all the ingredients collectively, occurs as the device is engaged in use and while brushing the user's hair scalp and/or hair. As noted above, in certain other embodiments, a cartridge in the form of an atomizer or pump sprayer may be used in the second, third or other auxiliary housing.

Furthermore, the inventor herein contemplates that the inventive device may in one embodiment include only two housings. Byway of an example only, in this alternative embodiment each of the two housings can be structurally and functionally identical and generally similar to the housing described in earlier embodiments. Accordingly, one of the two housings can have the plurality of bristles attached thereto. Additionally, given this embodiment, it will be appreciated by those skilled in the art that at least one cartridge inserted in one of the two housings, contains the hair building material in a "wet" form, whether gel, cream and the like, while at least one cartridge inserted in the other of the two housings, contains the hair building material in "dry" form, such as but not limited to powder, fiber-like strands, etc. As such, the processing, blending and dispensing of the hair building materials in this alternative embodiment of two housings will work substantially similar to the aforementioned preferred embodiments. Additionally, in this alternative embodiment, the handle (which may comprise and/or include a base) still has the movable member mounted thereon, and while it could be structured to comprise a dual or second movable member, it is preferably a single movable member connected to the handle and still also removably connected to the central housing. As a result, and similar to the operational features mentioned in embodiments earlier, the hair building material contained in one of the cartridges inserted into one of the two housings is penetrated by the movable member, sonically blended by the vibration, and dispensed directly on to the user's hair to blend with the hair building material contained in one of the other cartridges inserted in the other of the two housings. As a result, the hair material contained in each of the cartridges in each of the two housings collectively may be dispensed onto the user's hair, when the inventive device is in operative use.

Looking even further, the inventor herein also contemplates that the inventive device may in another embodiment include only one housing. In this additional preferred alternative embodiment, the inventive device comprises a handle (which may comprise and/or include a base), with a movable member and one housing with plurality of bristles connected thereto. As such, the user connects the housing with the plurality of bristles to the base, which has the movable member mounted thereon.

To illustrate this further, as the user attaches the housing to the handle (which as noted above may comprise and/or include the base), the movable member is mounted and structurally received within an inner cavity of the housing. As such, the inner cavity of the housing is sized, structured and configured to receive the movable member so as to ensure a secure fit but which also permits at least partial movement of a distal section of the movable member. Similarly, as described in earlier preferred embodiments, the movable member is structured to vibrate and/or oscillate at a frequency that allows the entire inventive device to vibrate as well, at least slightly, if not more. As such, the movable member is connected to a power supply that ensures its vibration when actuated. To further illustrate, the operational features in this embodiment, the user attaches the cartridge or cartridge assembly containing the hair building materials in the housing, with a frictional fit therebetween. However, even in this additional alternative embodiment, the movable member will preferably vibrate so as to cause the plurality of bristles to also vibrate as the user applies the hair building material on his or her hair.

As a result, and similar to the operational features mentioned in embodiments earlier, the hair building material contained in the cartridge inserted into the housing is penetrated by the movable member, sonically blended by the vibration, and dispensed directly on to the user's scalp and/or hair as one complete blend of the hair building material containing all the ingredients necessary to promote hair building attributes on the user's scalp and/or scalp hair. More specifically, the one cartridge inserted within the housing, contains the hair building material in the form of gel, dry powder, fiber-like strands, hair coloring agent(s) and/or structural combination thereof. Therefore, it may be appreciated by a person skilled in the art that the hair material contained in the cartridge in the housing would be blended all together internally within the cartridge, before it will be collectively dispensed as a complete hair building material comprising of all the ingredients necessary to promote hair building attributes onto the user's hair, when the inventive device is in operative use.

The inventor herein has also conceived of yet another embodiment for his inventive device. In this additional alternative embodiment, the inventive device comprises a handle (which may be referred to herein in places as a base) with a movable member and a bristle holder, but which does not include a central housing or any other housing. As such, the user securely connects the bristle holder to the handle, which has the movable member mounted thereon. To illustrate this further, as the user attaches the bristle holder on to the handle, the movable member is mounted and structurally received within an inner cavity of the bristle holder. As such, the inner cavity of the bristle holder is sized, structured and configured to receive the movable member so as to ensure a secure fit. Similarly, as in earlier preferred embodiments, the movable member is structured to vibrate and/or oscillate at a frequency that allows the entire inventive device to vibrate as well. As such, the movable member is connected to a power supply that ensures its vibration when actuated. To further illustrate the operational features in this embodiment, the user simply dips the plurality of bristles in each of the hair building material located within an external container and can thereby apply it directly onto the user's scalp and/or hair. However, even in this additional alternative embodiment, the movable member will preferably vibrate so as to cause the plurality of bristles to also vibrate as the user applies the hair building material on his or her hair.

Also in a preferred embodiment, the inventive hair applicator device comprises of a mirror attachment. The mirror attachment may be removably connected to the base and/or the central housing. Preferably, the mirror attachment is also movably disposed on the base and/or housing and is movable between an open orientation and a closed orientation which in one embodiment, is in opposing relation to the plurality of bristle elements on the exterior surface of the central housing. In other words, the mirror attachment is positioned on the opposite side of the plurality of bristle elements. This positioning of the mirror attachment can be deliberate in order to allow the user to visually observe the application and placement of hair building material(s).

Furthermore, in one of the preferred embodiments, the mirror attachment is detachable. The detachment allows the user to remove the mirror attachment, if and when desired.

As such, the mirror attachment can be detached from its connection to the base and/or central housing, and reattached when desired. To further characterize this, the central housing has a connecting member structured to receive and removably secure the mirror attachment to the central housing. Accordingly, it may be appreciated that in one of the preferred embodiments, the mirror attachment can be connected to the central housing in a snap fit, press-fit or other similar type of joint fit connections that allow the user to attach and detach the mirror attachment from the central housing, as and when preferred. Comparatively, in one of the other preferred embodiments with one housing, the housing has at least two connecting members. As such, each of the two connecting members are structured to receive at least a portion of the mirror attachment, sufficient to removably secure the mirror attachment to the inventive device. Alternatively, in one of the embodiments, the mirror attachment can also be permanently affixed to the central housing so as to avoid any detachment.

Additionally, the connected mirror attachment can be pivotally moved back and forth from a closed position to an open position, as briefly noted above. To further illustrate this, the closed position allows the mirror attachment to be folded in a manner that allows the mirror attachment to be generally and/or sufficiently aligned with the base and/or central housing. This alignment results in a parallel positioning of the mirror attachment relative to the exterior surface of the central housing, from which the plurality of bristle elements extend. Additionally, the pivotal nature of the mirror attachment improves visibility, particularly when the device is used to focus on specific areas of the hair scalp for concealment.

Furthermore, it will be appreciated from the description above and by those skilled in the art that in the preferred embodiments, one or more components of the hair applicator device are detachable from the handle and/or the base, such as the central housing, first housing, second housing and/or other auxiliary housing(s), mirror attachment, etc. Thus, for example, the mirror attachment and the central housing with the plurality of bristles can be collectively detached from the handle and/or base. For instance, while attaching the handle and/or base to the housing, the user may align the housing with the stepped configuration, slide it into place on the handle and/or base and rotate it to securely connect it to the housing. More particularly, as the handle and/or base is secured to the housing, the movable member mounted is substantially received within the hollow interior chamber of the housing so as to ensure a secure fit. Additionally, and as has been noted previously, the housing can have a first open end and a second open end, but when the handle and/or base is secured to the housing, the second open end closes to form a closed end.

Comparatively, when detaching the handle and/or base from the housing, it can be rotated in an opposite direction relative to the housing or in some embodiments, pulled apart. The opposite rotation may allow the handle and/or base to disengage from the housing, and be detached therefrom. More particularly, as the handle and/or base is detached from the housing, the movable member mounted is released from its secure fit in the hollow interior chamber of the housing. Additionally, the closed end of the housing is re-opened into the second open end. To further illustrate this preferred embodiment in a detailed manner, the handle and/or base is secured to the housing during attachment by a retention member disposed on the movable member. As a result, when the handle and/or base is rotated in e.g., a counter-clockwise direction relative to the housing and inserted therein, the retention member disposed on the movable member and positioned inside the housing, secures the handle and/or base to the housing, sufficient to present the inventive device as a one piece construction. Alternatively, as the handle and/or base is turned in e.g., a clockwise direction relative to the housing, the retention member unlocks and releases the handle and/or base from the housing, sufficient to illustrate the inventive device as a two piece construction, one being the handle or base and the other being the combination of the mirror attachment, the housing and the plurality of bristles attached thereto.

In an alternative embodiment, the hair applicator device of the present invention can include a compression member. The compression member may be disposed within the hollow interior of the first chamber of the central housing. As such, the compression member is sized, structured and configured to connect to the cartridge or the cartridge assembly, including but not limited to the first cartridge assembly and/or the second cartridge assembly. As such, and merely as an illustration, pressure is generated towards, into and/or within one or more ingredients of the hair building material carried in the cartridge assembly, which is securely connected to the compression member that is movable and disposable into and within the hollow interior of the first chamber of the central housing. This is accomplished when a predetermined force is exerted on the cartridge assembly towards the compression member, or vice versa, sufficient to secure the cartridge assembly on to the compression member. Accordingly, the predetermined amount of force in connecting the cartridge assembly to the compression member induces sufficient pressure to cause one or more ingredients of the hair building material contained in the cartridge assembly to forcibly release and be pushed into, through and from the slit, incision, or access opening through the plurality of pathways directly on to the plurality of bristle elements disposed on the exterior surface of the central housing.

Additionally, one or more ingredients of the hair building material can form a dry powder blend comprising all or some of the hair building ingredients. Furthermore, the hair building material can also be in the form of fibers that resemble hair like strands comprising all or some of the hair building ingredients. As such, the fiber resembling hair like strands may further comprise natural or synthetic colored pigments and/or activated charcoal. Given this, the hair like fibers and the powder blend of the hair building material can be stored in one cartridge or cartridge assembly, or preferably in separate, individualized cartridges or cartridge assemblies. Accordingly, and merely as an example, the powder, fiber and/or other dry forms of the hair building material can be contained in one cartridge, namely, the second cartridge assembly or contained in separate second cartridge assemblies. To further illustrate this, in one embodiment, the second cartridge assembly containing either the powder or fiber forms of the hair building material is inserted in the second housing of the device, while another second cartridge assembly containing either the powder or fiber form of the hair building material is inserted in the third housing of the inventive device. Additionally, at least one separate cartridge, preferably the first cartridge assembly, containing hair building material in a wet form, such as gel may be inserted in in the central housing of the inventive device.

Furthermore, the hair building material is preferably stored in the cartridge or the cartridge assembly including, but not limited to first cartridge assembly and second cartridge assembly. However, it can also be stored in other forms of containers such as a tube, tub, jar, plastic bag, or any other apparatus, that is/are sized, structured and configured to be received and secured in the central housing, second housing, and third housing, and concurrently while maintaining the fluid flow connection as illustrated earlier.

Additionally, in an embodiment of the device of the present invention, each of the second cartridge assemblies can be connected to a sleeve member having a sleeve cap. The sleeve member and the sleeve cap can help the user rotate the second cartridge assembly into and/or within the housings. Alternatively, however, any and all of the cartridge assemblies can be free of any connections to the sleeve member and inserted and/or rotated into the first, second or third housing securely. Furthermore, in an embodiment of the inventive device, the plurality of bristles, the central housing, the secondary housing, the third housing and the mirror attachment are collectively detachable from the handle and/or base. In this regard, it is ensured that the user is able to use the inventive device for spot treatment on the affected areas of the hair scalp by easily carrying the device in the pocket, thus making it effortlessly maneuverable and accessible.

Furthermore, in one of the preferred embodiments of the device of the present invention, the cartridge or cartridge assembly may not necessarily have a penetrable closed end. As such, the cartridge may have a closed end and an open end that is sealed with a sealing member before the cartridge or cartridge assembly is operationally put to use. To further illustrate this point, the user would peel off or remove the sealing member as the cartridge is ready to be inserted within the housing. Similarly, in the relevant embodiments, the access opening, slit or incision on the cartridge assembly may also be sealed with the sealing member. To further illustrate this, the user can peel or remove the sealing member off the access opening, slit, or incision of the cartridge assembly as it is ready to be inserted into the housing. Alternatively, in one of the preferred embodiments, the user may simply peel off the sealing member on the access opening, but retain the sealing member on the open end. This may allow the movable member to contact and easily penetrate the sealing member on the open end and ensure its exposure with the hair building material contained therein, when the cartridge is inserted into the housing using suitable force.

It is an object of the present invention to provide the user with a solution for addressing hair loss using hair building materials that can be stored, blended and dispensed from a substantially compact yet highly efficient device, capable of blending and dispensing hair building materials in both wet and dry forms, simultaneously, without requiring substantial modification or alternation of the device's structure.

It is a further object of the present invention to provide a device for storing and dispensing hair building material, which can be easily used, which is affordable if not low in cost, portable in nature and inexpensive to manufacture.

It is still another object of the present invention to provide a device for storing and dispensing hair building material, which can effectively create hair building fibers for a fuller look of hair on the user's scalp, through the blending and application of hair building materials subjected to mechanical sheer stress or mechanical friction.

Yet another object of the present invention is to provide a device for storing and dispensing hair building material, which can be used with a power supply or without a power supply, and can also function as a daily solution for hair loss or spot treatment.

Still another object of the present invention is to provide a device for storing and dispensing hair building material which has several components capable of being attached together for use, but also detachable for purposes of storage and also cleaning.

A further object of the present invention is to provide a kit having the inventive device intended for storing and dispensing hair building material, including a plurality of cartridges carrying various hair building materials, as well as a mirror assembly for the device and if desired, other components such as batteries, a cape, a storage tray, etc.

Yet another object of the present invention is to provide a storage tray into which the inventive device can be mounted, and onto which a plurality of cartridge assemblies can also be held and displayed, and which includes connectivity to a power source for providing a vibratory force or recharging any battery/batteries associated with the device.

It is also an object of the present invention to provide a device intended for storing and dispensing hair building material which can also be used with other hair care products, including color, conditioners, wet or dry shampoo, or even body soap if desired.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 3 is a perspective view of a second cartridge assembly that can be utilized with the inventive device according to one of the preferred embodiments.

FIG. 3A is a perspective view of a third cartridge assembly that can be utilized with the inventive device according to one of the preferred embodiments.

FIG. 5 is a perspective view of a first cartridge assembly in one of various preferred embodiments having an open end and a closed, penetrable end, as well as an elongated opening or slit.

FIG. 16 is a perspective view of an improved cartridge assembly, which may be considered a second cartridge assembly according to the description of the invention set forth below, and comprising a sleeve and a separate cartridge cooperatively structured and sized for insertion and rotation within the sleeve.

FIG. 17 is a perspective view of another improved cartridge assembly, which may be considered a first cartridge assembly, according to the description of the invention set forth below and somewhat similar to that shown in FIG. 5, but with the improved cartridge assembly defined by a single tube have at least two separate chambers formed within it, and a cartridge that is insertable into one of the two chambers of the tube.

FIG. 18-A is a front view of a combined base and central housing associated with the inventive device according to yet another preferred embodiment.

FIG. 18 is a side view of the inventive device shown in FIG. 18-A but with a bristle assembly attached thereto as well as a mirror attachment (similar to that shown in FIGS. 2, 6-7 and 10) mounted thereon, in a closed or collapsed orientation.

FIG. 19-A is an isolated side view of the mirror attachment shown in FIGS. 18 and 19, but in an open orientation.

FIG. 22-A is a perspective view of another cartridge for the inventive device shown in FIGS. 20-21, wherein the cartridge takes the form of an atomizer spray.

FIG. 22-B is a perspective view of another cartridge for the inventive device shown in FIG. 20-21, wherein the cartridge takes the form of a pump spray.

FIG. 22-C is a side view in exploded form of another type of cartridge for the inventive device, such as one capable of receiving a compression member, also illustrated.

FIG. 22-D is a view in exploded form of a cartridge assembly in yet another embodiment illustrating a component associated with an atomizer sprayer, similar to that shown in FIG. 22-A, but additionally including a stirring member.

FIG. 23-B is a close-up view of the reverse side of the base and central housing of the inventive device shown in FIGS. 18-A and 23-A.

FIG. 26-A is a top perspective view of a storage tray, as may be associated with the kit shown in FIGS. 25 and 26, and into which the inventive device can be mounted, and onto which a plurality of cartridge assemblies can also be held and displayed.

FIG. 26-B is a top perspective view of another storage tray, similar to that shown in FIG. 26-A, but into which the inventive device can be mounted, and which includes connectivity to a power source for applying a vibratory force to the storage tray and/or recharging any battery/batteries associated with the device.

FIG. 27 is a side view of the tray illustrated in FIG. 26-A.

FIG. 27-A is a side view of the tray illustrated in FIG. 26-B.

FIG. 28 is a perspective view of the cover guard shown in FIG. 28-A but illustrated as being attached to the inventive device.

Like reference numerals refer to like parts throughout the several views of the drawings.

DETAILED DESCRIPTION OF THE PREFERRED EMBODIMENT

Figure 1:
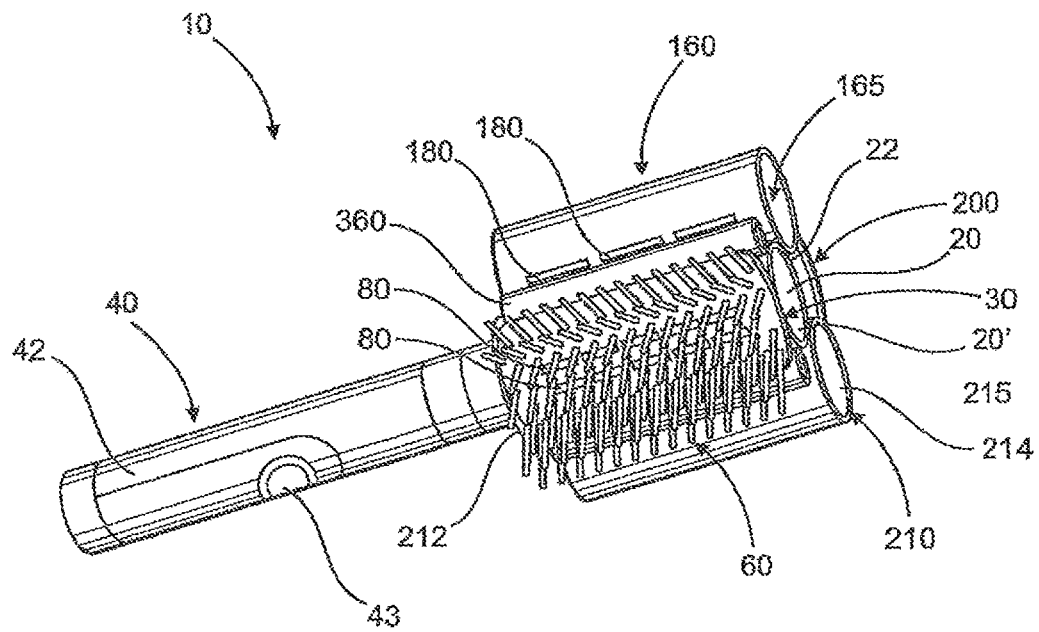
FIG. 1 is a perspective view of the inventive device according to one of the preferred embodiments.
Figure 2:
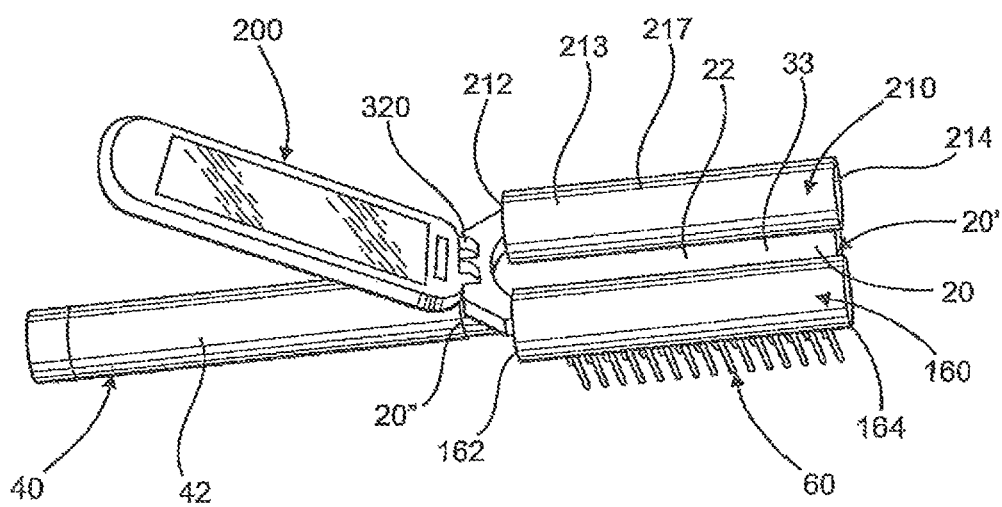
FIG. 2 is also a perspective view of the inventive device in accordance with the present invention, but illustrating one of the preferred embodiments including a mirror attachment in an open orientation.
Figure 4:
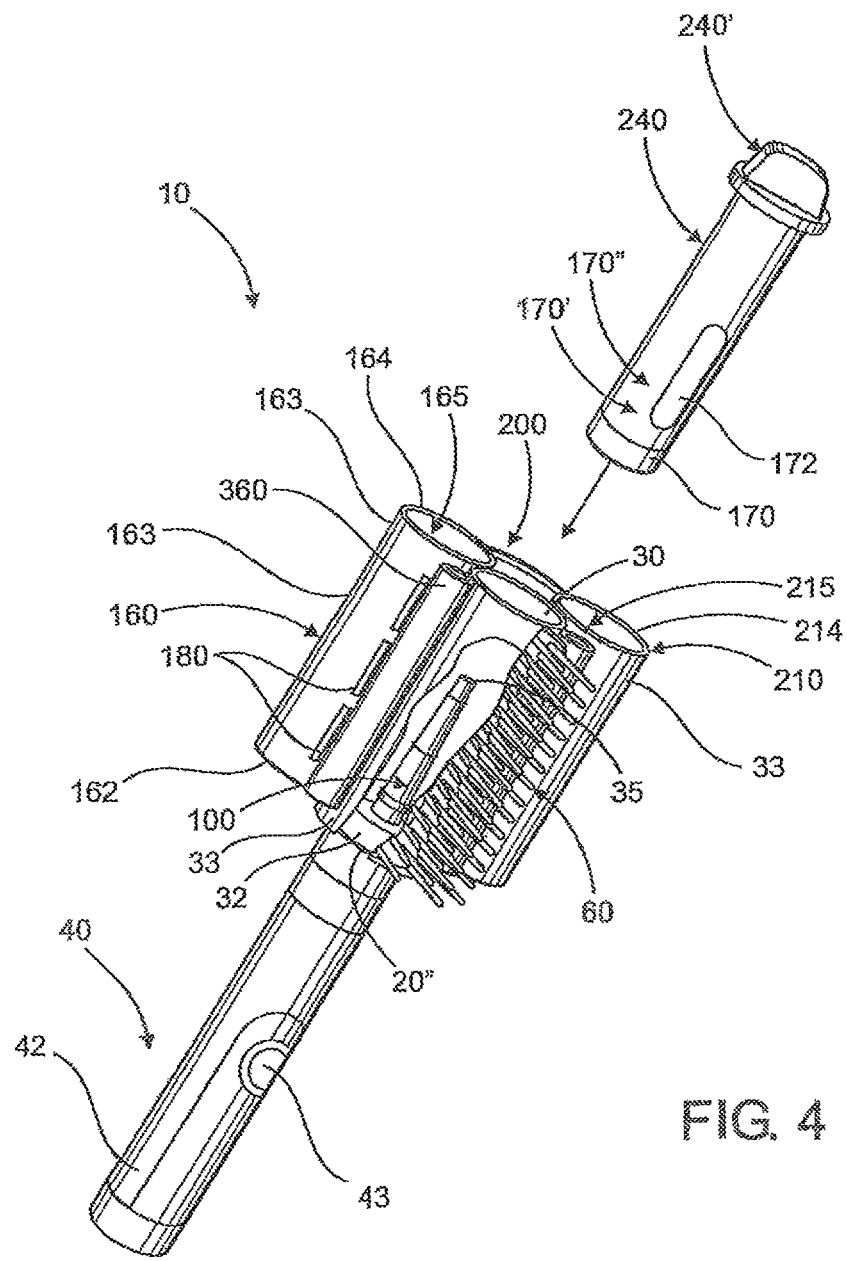
FIG. 4 is an exploded view in partial cutaway of the device shown in FIG. 1 illustrating insertion of the second cartridge assembly into one of the housings thereof, according to one of the preferred embodiments.
Figure 22:
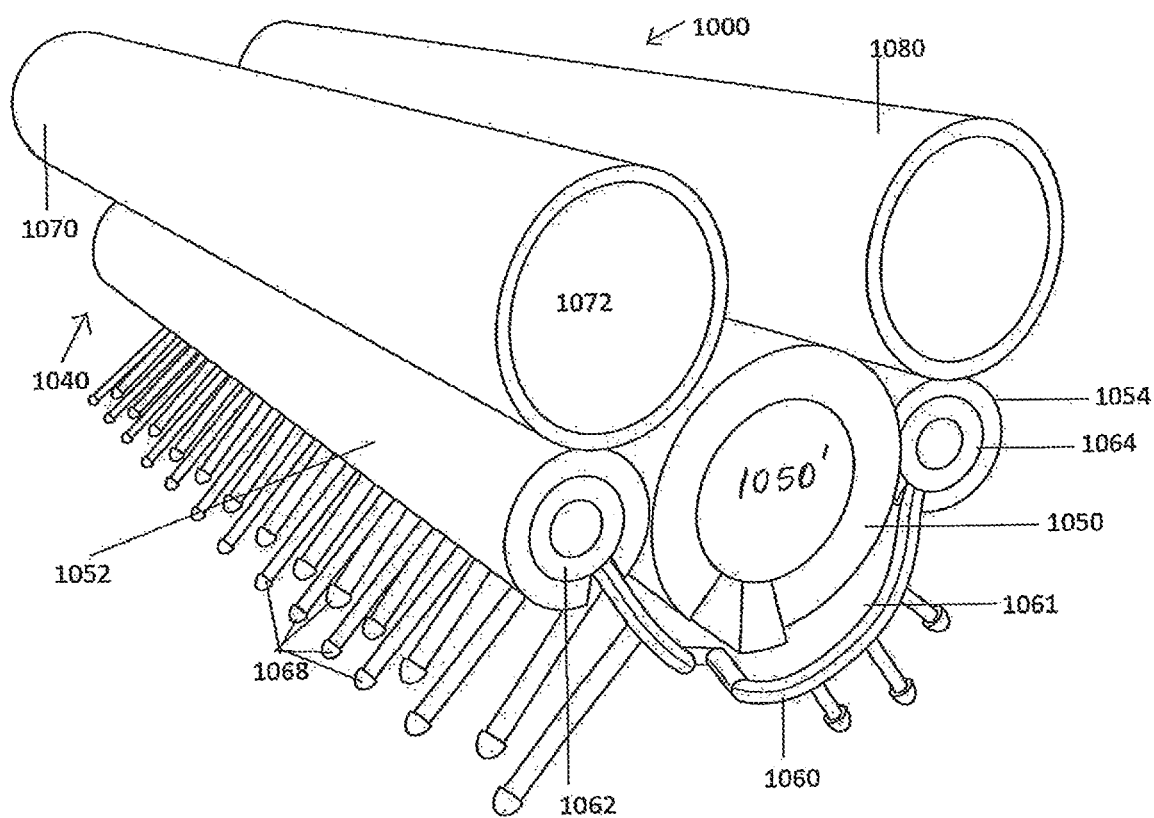
FIG. 22 is a perspective view of the inventive device shown in FIGS. 20-21, but illustrating both a first and second auxiliary housing mounted to the base, also without a mirror attachment.

The present invention is directed to a device, generally indicated as 10 in FIGS. 1-2 and 4, and to an improved device 1000 as illustrated in FIGS. 18 and 22, for storing, processing and dispensing hair building material(s). More specifically, the device 10 and 1000, is structured to store, process, and dispense different types or portions of the hair building material, such as a "wet" form and a "dry" form, and wherein each portion includes different ingredients. Further, each of the different portions and corresponding ingredients of the hair building material may be independently stored on the device 10 and 1000. In addition, the different portions are concurrently dispensed and substantially or partially blended with one another in the area of a plurality of bristles 60, 1060 associated with the device 10, 1000, prior to and concurrent with application of the blended hair building material onto the hair and scalp of the user. In at least one embodiment, the different portions of hair building materials are concurrently dispensed by the device 1000 to the plurality of bristles elements 1060 along flow paths that are in spaced apart relation to each other, for application and blending by the bristles upon application to and brushing of the hair scalp by a user.

The inventive device 10 and 1000 can be utilized on a variety of different hair types, hair textures and colors. Additionally, the inventor hereof has developed a unique and proprietary hair building composition, based on a variety of ingredients disclosed herein, which is intended for primary use as the hair building material(s) to be stored, processed, and dispensed by the device 10 and 1000. However, it is emphasized that the inventive device 10 or 1000 could also be used to store, process and dispense a variety of other hair building materials, containing a variety of one or more other ingredients, including or alternatively, other hair care products, such as coloring agents, conditioners, shampoos, sprays, and the like. As such, each of the embodiments of the device 10 and 1000 as well as the scope of the present invention should not be limited to use with the unique hair building composition described in detail herein.

Figure 24:
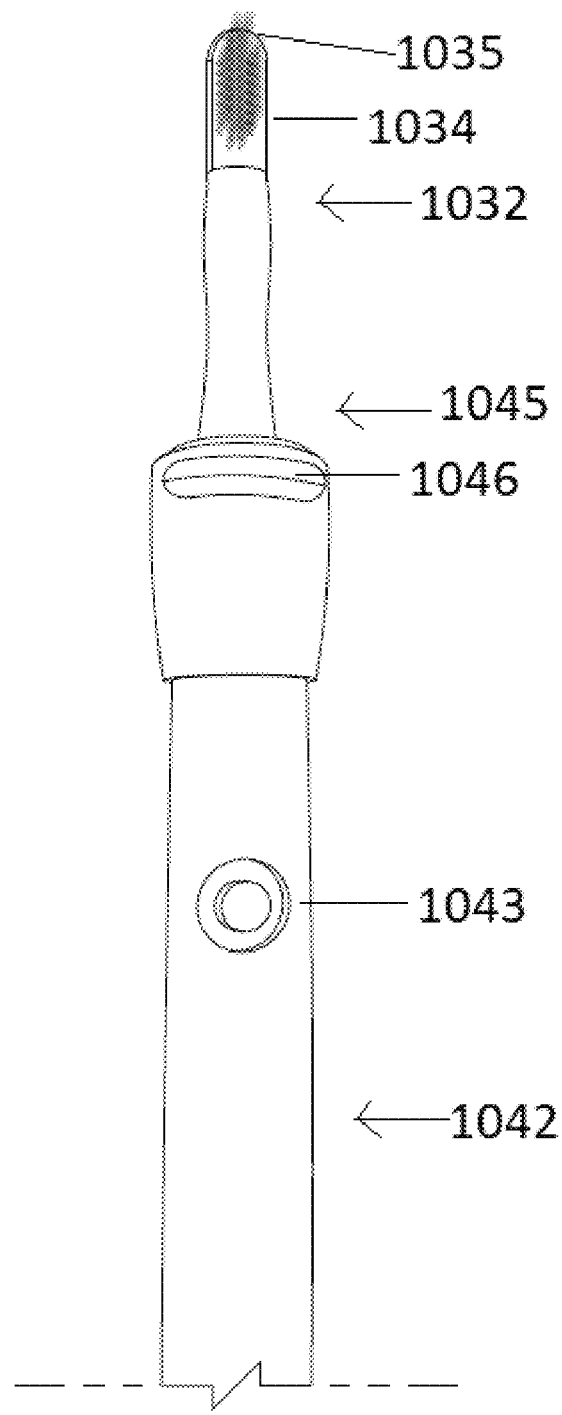
FIG. 24 is a perspective view of a handle associated with the inventive device shown in FIGS. 18-23B, including a movable member mounted thereon and having a puncturing tip formed at a distal end thereof.

Referring now to FIGS. 1 and 2, the device 10 of the present invention is illustrated in one preferred embodiment and is seen to include a base 40 having a central or first housing, 20 connected thereto. In some embodiments described subsequently herein, however, the base 40 and central housing 20 are integrally formed as a single piece, and include a detachable handle. As shown in FIGS. 1 and 2, the first or central housing 20 is defined by a body or wall 22 that will preferably be, but is not limited to, a generally cylindrical shape. Further, the central housing 20 includes an open end 20', a second, oppositely disposed closed end 20", and a hollow interior or first chamber 30. The central housing 20 is sized, structured, configured to receive a first supply of the hair building material, such as a "wet" hair building material, which may be contained and/or stored in a first cartridge assembly 120 as shown in FIG. 5. As indicated, the first supply of hair building material comprises one of a plurality of portions of the hair building material which are eventually blended with one another. Accordingly, as shown in FIG. 5, the first cartridge assembly 120 carries a first supply of a predetermined portion of hair building material and is disposed within the hollow interior or first chamber 30 of the central housing 20. Also, as shown in FIGS. 1 and 2, the first housing 20 is constructed of a generally rigid material and, at its closed end 20" is connected to a corresponding portion of the base 40. Further, the base 40 includes a handle or grip 42 which is preferably structured to be easily grasped by a user of the device 10 for manipulation thereof, thereby facilitating its use in a manner similar to a common hairbrush or comb. As described further herein, in some embodiments such as shown in FIGS. 18-A and 22, the first central housing 1050 and base 1040 may be formed integrally together or otherwise joined together, and a separate handle 1042 (e.g., as shown in FIG. 24) may be connected thereto.

Still referring to FIGS. 1 and 2, the body 22 of the first central housing 20 has an exterior surface 33 disposed adjacent to and/or in communication with a plurality of bristle elements 60 connected thereto, and/or to the base 40, in a generally communicating relation with the first central housing 20 and first cartridge assembly 120 including the first supply of hair building material contained therein. In addition, a plurality of apertures or pathways 80 are formed in the first central housing 20 and define a flow path or path of fluid flow for the portion of the hair building material contained within a corresponding or first cartridge 120 within the first central housing 20. Each of the plurality of apertures or pathways 80 are formed in the body 22 of the first housing 20 so as to define a flow path of the hair building material from the cartridge 120 to the plurality of bristle elements 60. Also, each of the apertures or pathways 80 are sized, structured, and configured to accommodate the consistency of the ingredients of the portion of the hair building material within the first cartridge 120. The flow path or pathways for the corresponding portion of the hair building material at least partially defined by the plurality of apertures 80 facilitate its delivery from the interior of a corresponding first cartridge, to the plurality of bristles 60, for blending with the other portions of the hair building material, as described hereinafter. Further, in the embodiment of FIG. 1, the plurality of pathways or apertures 80 defining a part of the aforementioned flow path is/are preferably be disposed to deliver the corresponding portion of the hair building material between the bristle elements 60.

The plurality of bristle elements 60 are structured to create a mechanical friction on the user's scalp as the hair building material is dispensed thereon. More particularly, while each, or at least a majority of the plurality of bristles 60 are formed of a substantially rigid material, they are also movable due at least in part to the oscillation and/or vibrations of the inventive device 10 in the embodiment including a motor, as described further below, but also have at least some flexibility so as to be movable while undergoing the motion caused and forces applied by the user's movement of them in brushing his or her hair. It should be evident that the motorized or non-manual movement of the plurality of bristle elements 60 can be provided by a power supply source disposed in the handle 42 or base 40 of the inventive device 10.

That is, and in at least one embodiment of the present invention, the base 40 and/or handle portion 42 is/are structured to include a drive motor and appropriate drive linkage, which is not shown in the drawings. Further, and as shown in FIG. 1, at least one actuator switch 43 is operatively connected to a power supply, also not shown for purposes of clarity. Suitable wiring and/or control circuitry may also be disposed within an interior of the base 40 and/or handle 42 for connection to the power supply. The power supply may be a self-contained battery carried within an appropriate portion of the base 40 and/or handle 42. In the alternative, the device 10 can also be operated with other electric power sources, such as being connected by an appropriate electrical cord or the like to a common electrical outlet. Also, the base 40 and/or handle 42 can be sealed to prevent any water damage.

Therefore, in use, activation of the aforementioned drive motor through manipulation of the activating switch 43 will exert a vibrational force on at least a portion of the base 40 and/or handle 42 associated with the mounting or connection of the plurality of bristle elements 60 and on one or more housings, specifically including the first housing 20. As explained in greater detail hereinafter, such a vibratory force will be sufficient to alter the viscosity of at least one portion of the hair building materials, such as a gel form, and to facilitate dispensing of the various portions of the hair building material from each of a possible plurality of hair building material supplies or cartridges 120 located in different ones of a plurality of housings on the base 40. However, it is to be noted that in at least one alternative embodiment, the device 10 can function manually, requiring no power, as described subsequently herein.

With further regard to the generation of a vibratory force and with primary reference to FIG. 4, the device 10 may further comprise a movable member 100 connected to and at least partially, movably disposed within the hollow interior 30 of the first or central housing 20. The movable member 100 is formed of a rigid material, and has a first end 32 connected to the end 20" of the housing 20 so as to close that end 20". An opposite distal end 35 preferably includes a pointed configuration, wherein at least a portion of the movable member 100, including the distal end 35, is at least partially enclosed within the hollow interior 30 of the first housing 20. When so disposed, the distal end 35 may be in connecting, penetrating, etc. relation to the first cartridge, such as 120, disposed within the hollow interior 30. In use, and as at least partially described above, the movable member 100 may be electronically connected in driven relation to the drive motor contained within the base 40 and/or handle 42. Once activated, through appropriate electrical and mechanical connection between the movable member 100 and the self-contained drive motor, the movable member 100 will sonically oscillate and/or generate a vibratory force. This vibratory force is transferred to at least the first cartridge 120 within the hollow interior 30 of the central housing 20, as well as to the portion of the hair building material contained therein. Such vibratory force exerted on or transferred to the first cartridge 120, as well as its contents will be sufficient to vary the viscosity of the hair building material to the point where it may be at least partially liquefied. By way of example only, the portion of the hair building material retained within the cartridge may be in a gel-form. As such, the viscosity of such a gel must be reduced, possibly to the point of being at least partial liquefied, so as to facilitate the dispensing of the gel-like portion along the flow path from the cartridge 120 and out of the access openings or apertures 80 formed in the first housing 20.

Figure 11:
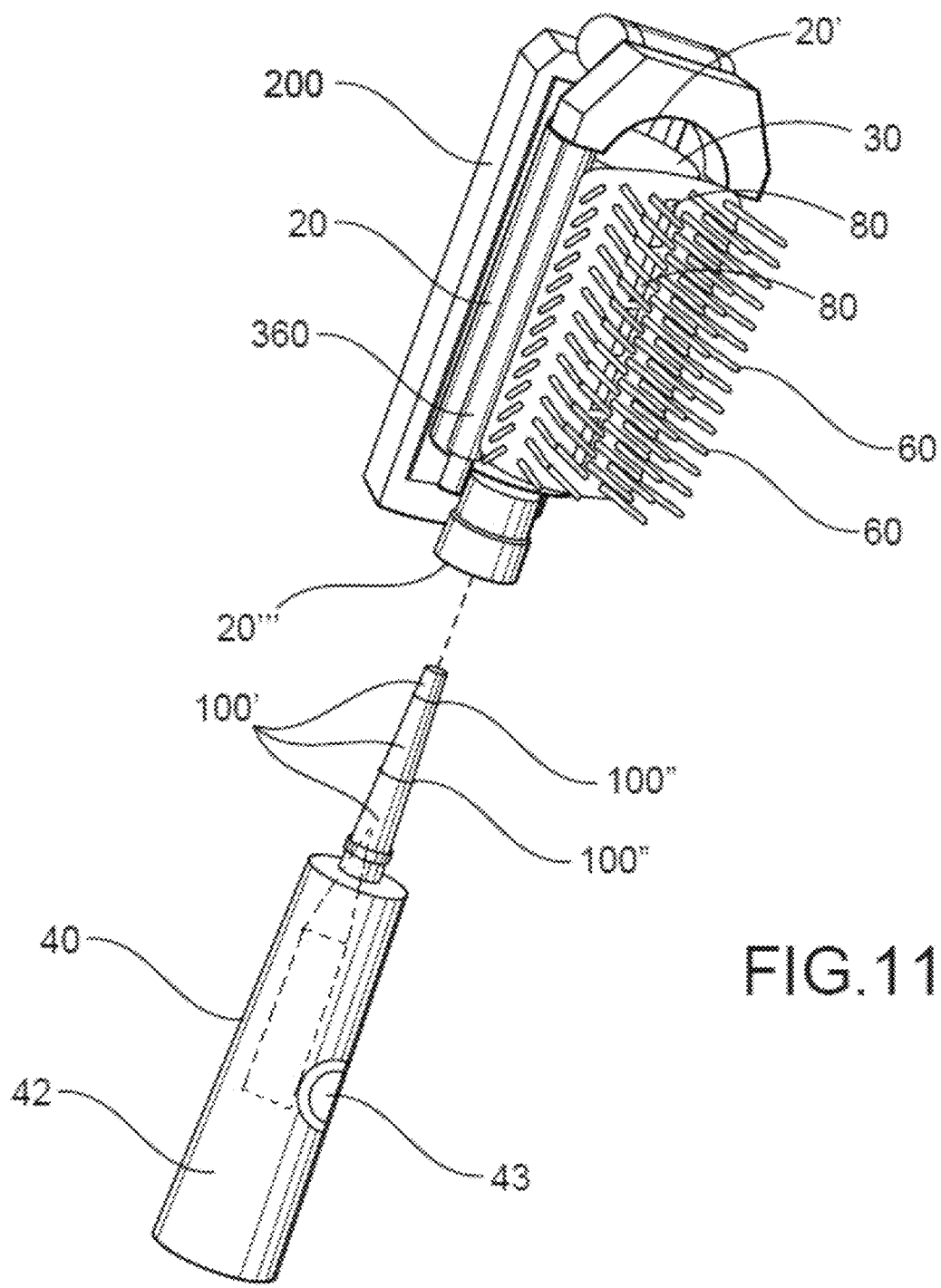
FIG. 11 is an exploded view of the inventive device shown in FIGS. 9 and 10, illustrating the handle (which may comprise and/or include a base) with a movable member mounted thereto, and in a position detached from the central housing of the device.
Figure 12:
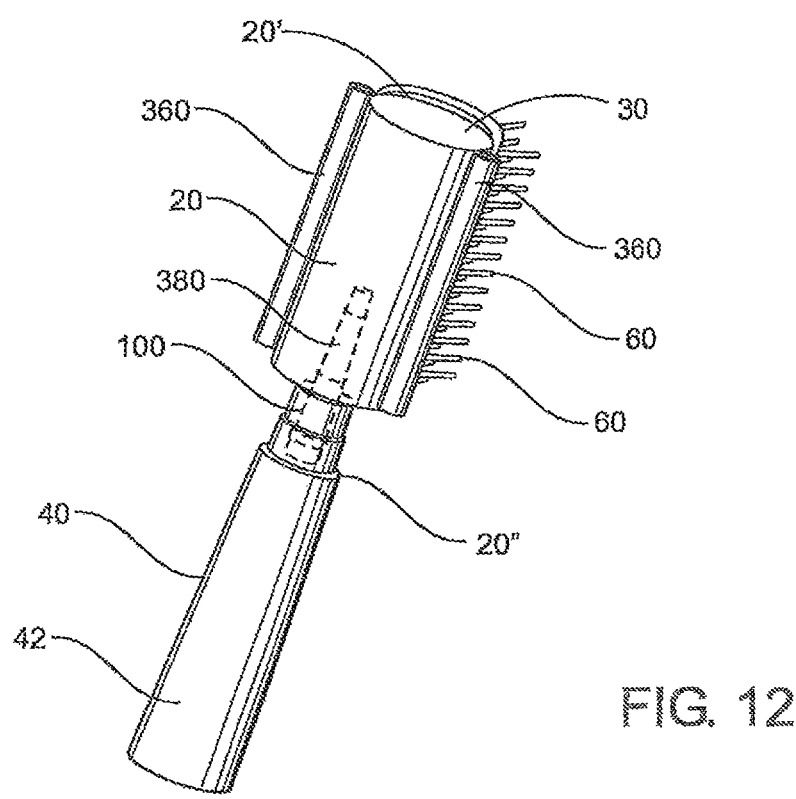
FIG. 12 is a perspective view in partial phantom of the inventive device illustrating the movable member disposed within the hollow interior chamber of the housing, when the handle and/or base is attached to the housing, according to one of the preferred embodiments.

With further regard now to another one of the preferred embodiments, and as shown in FIGS. 11 and 12, the movable member 100 can be structured to have an external surface configuration that is stepped as at 100', so as to have a lowest portion with a widest outer diametric dimension than an adjacent portion, which in turn has a wider outer diametric dimension that an uppermost or top portion. This stepped configuration on the movable member creates a ledge 100" around each of the layers, approximately where the plurality of steps 100' connect to each other. Accordingly, when the user connects the base 40 and/or handle 42 to the first central housing 20, the movable member 100 mounted on the base 40 and/or handle 42 is structured to be received within a receiving member 380 disposed within the central housing 20. More particularly, the stepped exterior configuration of the movable member 100 allows for it to be removably secured to the receiving member 380, and helps to ensure a secure fit of the base 40 to the central housing 20 for operation of the device. In the preferred embodiment, the secure connection of the movable member 100 into the receiving member 380 allows the receiving member 380 to also vibrate and oscillate when the movable member 100 is in operational use.

With further regard to the interaction and the exertion of a vibratory force by the movable member 100 on the first cartridge 120, primary reference is directed to FIG. 5. As previously described, a first supply of hair building material may be contained within the first cartridge assembly 120. The portion of the hair building material contained within the cartridge may be a "wet" form, such as but not limited to a gel, lotion, cream etc. and/or may be another type of hair care product, which will be dispensed for blending with other portions of the hair building material, and application onto a user's hair and/or scalp. As also indicated, the first cartridge assembly 120 is sized, structured and configured to be received within the hollow interior chamber 30 of at least the first housing 20. As shown in FIG. 5, the first cartridge assembly 120 can include an open end 120' and a penetrable closed end 120". The closed end 120" may alternatively be closed by way of a heat seal or membrane. The closed end 120" is structured to be pierced by the pointed configuration of the end 35 of the movable member 100, upon the application of a suitable force being exerted on the cartridge 120, when it is moved into or placed within the interior 30 of the housing 20 (or vice versa, when the movable member 100 is connected to the base). As such, the movable member 100 can penetrate through the closed end 120" of the first cartridge assembly 120 when the user exerts a suitable predetermined force on the cartridge 120. The exertion of the predetermined force and resultant penetration of the closed end 120", serves to connect the first cartridge assembly 120 to the movable member 100 inside the hollow interior 30 of the housing 20. As a result of this connection, the exertion of a vibratory force by the movable member 100 will result in a reduction of the viscosity of the portion of the hair building material within the cartridge 120 to a point of possible liquidation.

As also illustrated in FIG. 5, the first cartridge assembly 120 includes an outer wall 133 with an exterior surface 130 extending the length thereof between the open end 120' and penetrable closed end 120". The outer wall 133 of the first cartridge assembly 120 also includes and is structured to define at least one access opening or slit 140 completely through the outer wall 133, between the exterior surface 130 and an interior surface thereof, so as to allow one or more ingredients of the hair building material carried inside the first cartridge assembly 120 to flow out of and through the access opening or slit 140. Preferably, this slit 140 extends longitudinally along at least a portion of the outer wall 133 as shown in FIG. 5, and ideally along a majority of the length thereof. Additionally, in use of the inventive device 10, the access opening or slit 140 can be aligned with the plurality of apertures or pathways 80 on the body of the central housing 20 to further define the flow path of the hair building material. However, in an alternative embodiment, the first cartridge assembly shown in FIG. 5 does not have to include a slit 140, as the open end 120' may serve as an access opening, as described further herein with regard to FIG. 22-C.

To align the access opening or slit 140 with the plurality of apertures 80 of the central housing 20, the first cartridge assembly 120 is rotated within the hollow interior 30 of the central housing 20 until the access opening or the slit 140 is facing and/or in communicating relation to the plurality of apertures or pathways 80 of the central housing 20. As a result, such communicating relation of the flow path for the hair building material is at least partially defined. Thus, the portion of the hair building material carried by the first cartridge 120 can flow and/or be dispensed out of the first cartridge assembly 120 through the access opening or slit 140 and through the plurality of apertures or pathways 80 on the exterior surface 35 of the housing 20 into the area of the plurality of bristle elements 60. Once dispensed into the area of the plurality of bristle elements 60, the gel-like material may be at least partially blended with other portions of the hair building material which, as described in greater detail herein, are concurrently dispensed into the area of the bristle elements 60 from the other supplies and/or cartridges of the hair building material. Thereafter, the blended hair building materials will be applied onto the user's scalp and/or hair as the user uses a device 10 in a conventional hair brushing manner.

From the foregoing, it may be appreciated that the outer diametric dimensions of the first cartridge assembly 120 are substantially similar to and yet somewhat or sufficiently smaller than the inner diametric dimensions of the first central housing 20 and its hollow interior chamber 30, so as to create a frictional fit between them. The frictional fit ensures that at least a portion of the first cartridge assembly 120, but preferably all or substantially of it, is removably secured within the hollow interior chamber 30 of central housing 20. To further illustrate, as force is continued to be applied on the first cartridge assembly 120 during its insertion into the central housing 20, the penetrable closed end 120" establishes contact with the movable member 100. As such, the movable member 100 is sized, structured and configured to penetrate within the first cartridge assembly 120. Moving forward, as the insertion of the first cartridge assembly 120 continues and the contact increases, the movable member 100 penetrates so as to intrude through the penetrable closed end 120" of the first cartridge assembly 120, becoming exposed to and contacting the hair building material contained therein. Thus, the movable member 100 is exposed directly to the hair building material contained in the first cartridge assembly 120. Additionally, it is preferable that the force applied to the first cartridge assembly 120 be sufficient to frictionally secure a majority portion of the first cartridge assembly 120 within the hollow interior first chamber 30 of the central housing 20, so as to ensure that the first cartridge assembly 120 is removably affixed on the movable member 100 when in operational use.

As also indicated, one or more preferred embodiments of the inventive device 10 include a plurality of cartridges, respectively indicated as a second cartridge 170 in FIG. 3, and a possible third cartridges 310, shown in FIG. 3A. Each of the plurality of cartridges 120, 170, 310 will preferably define an individual supply and/or different portion of the hair building material or other hair care product. Further, each of the plurality of first, second, third, etc. cartridges are disposed in a different one of a possible plurality of housings, each of which are connected to or mounted on the base 40 and as perhaps best illustrated in FIGS. 1 and 4. Therefore, and as described further herein, the device 10 will be structured to provide for the substantial blending of the different portions of the hair building material originally contained in and dispensed from a plurality of different supplies, which may be in the form of the cartridges or canisters, as set forth above. Moreover, such substantial blending and concurrent dispensing will occur in the area of the plurality of bristles 60 and/or the hair and/or scalp of the user.

Therefore, and as illustrated in FIGS. 1, 2 and 4, at least one preferred embodiment of the present invention includes the device 10 having a second housing, generally indicated as 160. The second housing 160 is preferably connected to the base 40 at an upper surface thereof and/or adjacent to and in cooperating relation with the first central housing 20. Similar to the first central housing 20, the second housing 160 may be formed of a rigid material and may have a first closed end 162, a second open end 164 and a hollow interior second chamber 165. In another embodiment, however, the second housing may have two open ends. The second housing 160, as shown in FIG. 4, also comprises an outer wall 163 between the first and second ends 162 and 164, having a plurality of access openings 180, so as to establish or at least partially define a flow path for the portion of the hair building material contained within another cartridge disposed within the second housing 160. More specifically, the plurality of access openings 180 formed in the second housing 160 allow for the flow of one or more ingredients of the hair building material from the cartridge disposed within the second housing 160, and to be disbursed onto the plurality of bristle elements 60, and then onto the user's hair while the plurality of bristle elements 60 are engaged in a brushing movement on the user's hair and scalp. From FIGS. 1 and 3, it will be appreciated that the flow path of hair building materials through the access openings 180 in second housing 160 are spaced apart from the plurality of apertures or pathways 80 formed in the central housing 20.

Thus, and with reference again to FIG. 3, in one or more preferred embodiments the present invention further comprises a second supply of hair building material, which may be a "dry" form, contained within a cartridge assembly such as 170. The second cartridge assembly 170 includes an outer wall 170' with an exterior surface 170" extending the length thereof. The outer wall 170' of the second cartridge assembly 170 also includes and is structured to define at least one access opening 172 extending through the exterior surface 170" in communicating relation with the interior of the second cartridge 170. The access opening 172 is disposed and structured to allow the portion of the hair building material contained within the cartridge 172 to pass from the interior thereof and along the corresponding flow path, at least partially defined by the plurality of openings 180 in the second housing 160, to a plurality of the bristle elements 60, as shown in FIGS. 1 and 4. In other embodiments, the access opening 172 of the second cartridge 170 may alternatively comprise an elongated slit or a plurality of openings.

In use, the second cartridge assembly 170 containing a portion of the hair building material is inserted into the hollow interior second chamber 165 of the second housing 160. As such, the hollow interior of the second chamber 165 of the second housing 160 is sized, structured and configured to receive and reasonably secure the second cartridge assembly 170 within it. More specifically, the dimensions of the second housing 160 are sufficient to allow the second cartridge assembly 170 to be removably received and yet remain snugly secured within the hollow interior second chamber 165. When ready for use, the user aligns the access opening 172 with the plurality of openings 180 formed in the second housing 160. More specifically, the second cartridge assembly 170 is inserted into the hollow interior of the second chamber 165 of the second housing 160. Once located therein, the cartridge 170 may be rotated or otherwise appropriately positioned to align and establish a flow path between the access opening 172 with the plurality of openings 180 of the second housing 160 and to remain reasonably secured therein. As such, rotating the second cartridge assembly 170 into alignment facilitates the portion and/or one or more ingredients of the hair building material carried in the second cartridge assembly 170 to flow along the flow path. As indicated, the flow path for the hair building material is at least partially defined by the access opening 172 and the plurality of openings 180 so as to facilitate it being dispensed onto the plurality of bristle elements 60 for blending at the hair or scalp of the user. As set forth above, the plurality of openings 180 on the second housing 160 are also in communication with the plurality of bristle elements 60. As a result, once the portion of the hair building material within the cartridge 170 passes through the plurality of openings 180, it is concurrently dispensed and substantially blended, with the portion of the hair building material being simultaneously dispensed from the first cartridge, as at 120, within the first central housing 20, through the plurality openings 80 formed therein, as best shown in FIG. 1.

Furthermore, it is equally important to note that the second cartridge assembly 170 is structured to frictionally fit within the hollow interior second chamber 165 of the second housing 160. Given this, it is important to that the diametric dimensions of the second cartridge assembly 170 are sufficiently smaller than the diametric dimensions of the second housing 160, so as to create a frictional fit, and as such, secure at least a portion of the second cartridge assembly 170 within the hollow interior second chamber 165 of the second housing 160. Moving forward, as the force is continued to be applied on the second cartridge assembly 170 as it is inserted into the second housing 160, the frictional fit secures a majority portion of the second cartridge assembly 170 within the hollow interior second chamber 165 of the second housing 160, so as to ensure that the second cartridge assembly 170 is operationally in use and removably affixed therein.

As represented in FIGS. 1, 2 and 4, in another preferred embodiment, the device 10 of the present invention may comprise a third housing 210. The third housing 210 is connected to the base 40 adjacent to and in operative relation to the first central housing 20. As shown in several of the drawings, the first central housing 20, second housing 160 and third housing 210 are preferably all disposed in generally parallel, but spaced apart relation to each other. Similarly, the third housing as shown in FIG. 2, may also be formed of a rigid material and may include a first closed end 212, a second open end 214 and a hollow interior. In an alternative embodiment, the third housing 210 may have two open ends. The third housing 210 also comprises an outer wall 213 having a plurality of slots 217, which similar to the plurality of openings 180 in the second housing 160, are disposed in flow communicating relation with the plurality of bristle elements 60. As such, the third housing 210 is sized, structured and configured to receive a third supply of the hair building material contained within an additional cartridge therein. The third or additional cartridge may be substantially equivalent in size, structure and configuration as the second cartridge assembly 170. It will be appreciated that the flow path of hair building materials through the plurality of slots or other openings 217 in the third housing 210 are spaced apart from the plurality of apertures or pathways 80 formed in the central housing 20, as well as the plurality of openings 180 in the second housing.

More specifically, the dimensions of the third housing 210 are sufficient to allow another one of the second cartridges 170, or it structural equivalent, to be received and remain secured within the hollow interior thereof. Once disposed within the interior of the third housing 210, a third or additional one of the second cartridges 170 is aligned, such as by rotation, to dispose the access opening 172 with the plurality of slots 217 formed in the third housing 210. As a result, the flow path between the cartridge within the interior of the third housing 210 and out onto the bristle elements 60 is at least partially defined by a corresponding access opening formed in the inserted cartridge and appropriate openings or apertures formed in the third housing 210. As such, rotating the second cartridge assembly 170 into alignment ensures that the access opening 172 on the second cartridge 170, or other access openings 172 on a different third cartridge 310, is in a flow facilitating connection with the plurality of bristle elements 60.

As a result, a portion of the hair building material contained within the cartridge disposed within the third housing 210 will be dispensed along a flow path, at least partially defined by the access opening 172 in the contained cartridge within the third housing 210 and the plurality of openings 217 contained within the third housing 210 itself. As set forth above, the portion of the hair building material within the third cartridge 310 will be concurrently dispensed and substantially blended with the other portions of the hair building material passing from the first and second cartridges 120 and 170 through the first and second housings 20 and 160 onto the plurality of bristle elements 60. The blended portions or ingredients of the hair building material will thereby be distributed onto the hair of the user during the performance of a combing or brushing action of the device 10.

Figure 6:
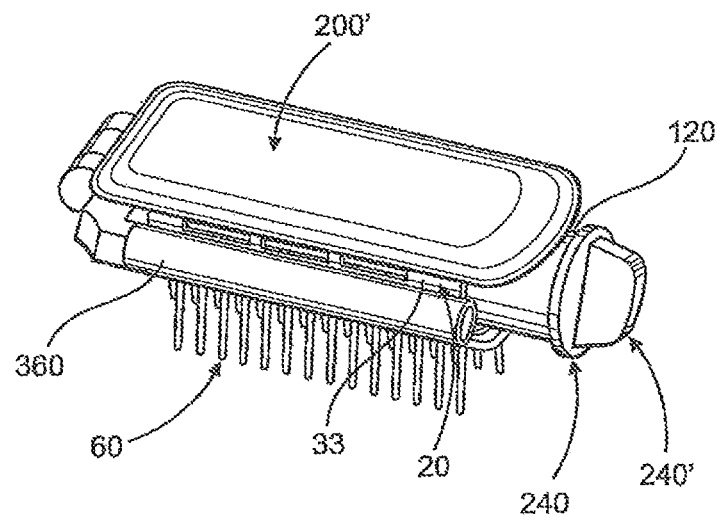
FIG. 6 is a side view of the inventive device illustrating a cartridge assembly, such as that shown in FIG. 3, loaded into the hollow interior first chamber of the central housing and a mirror attachment in a closed orientation in one of the preferred embodiments.
Figure 7:
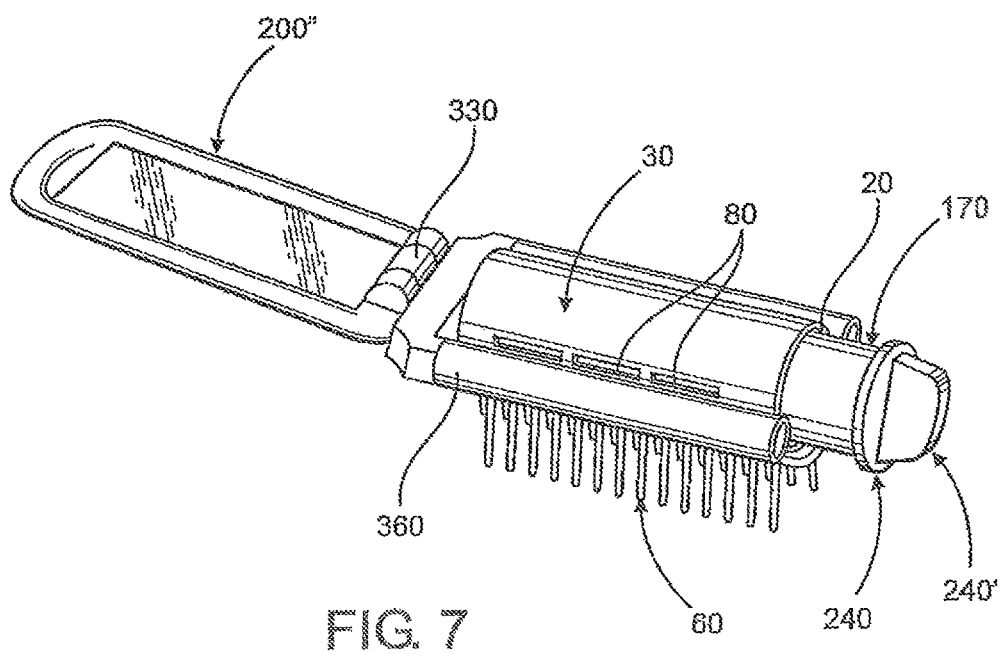
FIG. 7 is a perspective view of the inventive device illustrating the hollow interior first chamber receiving a cartridge assembly, such as that shown in FIG. 3, and a mirror attachment in an open orientation, according to one of the preferred embodiments.

With reference now to FIGS. 2, 6 and 7, one or more preferred embodiments of the present invention may include a mirror attachment, generally indicated as 200. The mirror attachment 200 is preferably connected to the base 40 adjacent to and in partially surrounding relation to the first central housing 20. In addition, in a preferred embodiment, the mirror attachment 200 is movably mounted and pivotally disposed relative to the exterior surface 33 of the first central housing 20. As such, the mirror attachment 200 is movable and allows the user to pivot the mirror attachment 200 from a closed position 200', which may be substantially hidden and in generally parallel relation to the central housing 20, as illustrated in FIG. 6, and to an open, exposed position 200" as illustrated in FIG. 7. Additionally, the pivotal connection of the mirror attachment 200 to the central housing 20 readily allows for movement thereof into the open position and offers improved visibility to the user when applying the applying hair building material, especially to selected areas of the user's hair and/or scalp during use of the inventive device 10.

Figure 8:
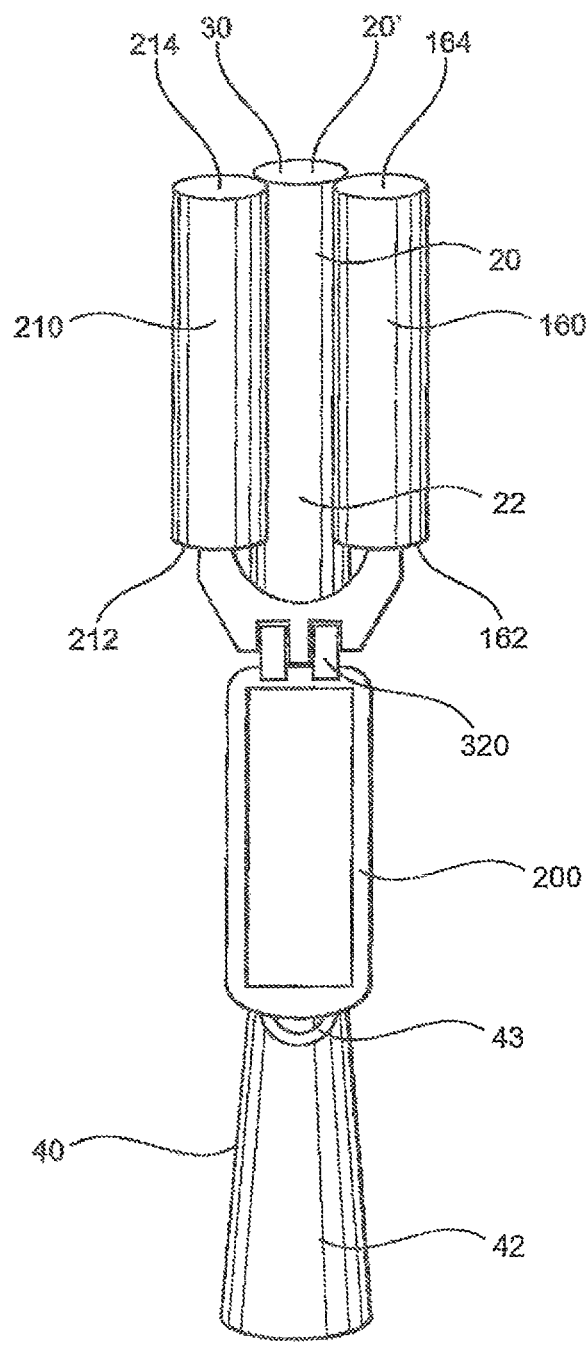
FIG. 8 is a perspective view of the inventive device illustrating a mirror attachment having a connecting member structured to be received within and removably secured to the device according to one of the preferred embodiments, with the mirror attachment being shown in an open position overlaying the handle of the device.
Figure 10:
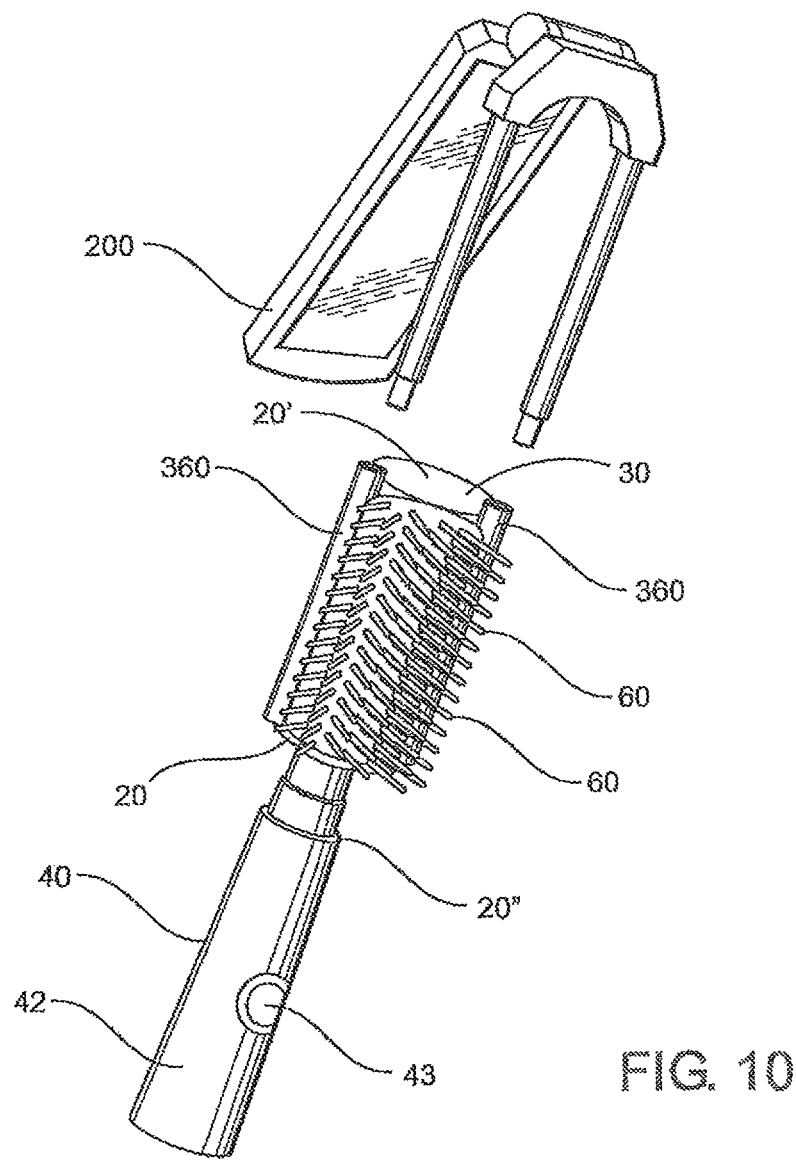
FIG. 10 is an exploded view of the inventive device shown in FIG. 9, but illustrating the mirror attachment detached from the connecting members according to one of the preferred embodiments.

Furthermore, in one of the preferred embodiments as shown in FIGS. 8 and 10, the mirror attachment 200 is detachable. The detachment allows the user to remove the mirror attachment 200, if and when desired. As such, the mirror attachment 200 can be detached from its connection to the central housing 20, and reattached when desired. To further characterize this, the central housing 20 has a pivoting connecting member 320 structured to receive and removably secure the mirror attachment 200 to the first central housing 20. Accordingly, the mirror attachment 200 can be connected to the central housing 20 in a snap fit, press-fit or other similar type of joint fit connections that allow the user to attach and detach the mirror attachment 200 from the central housing 20, as and when preferred.

Figure 9:
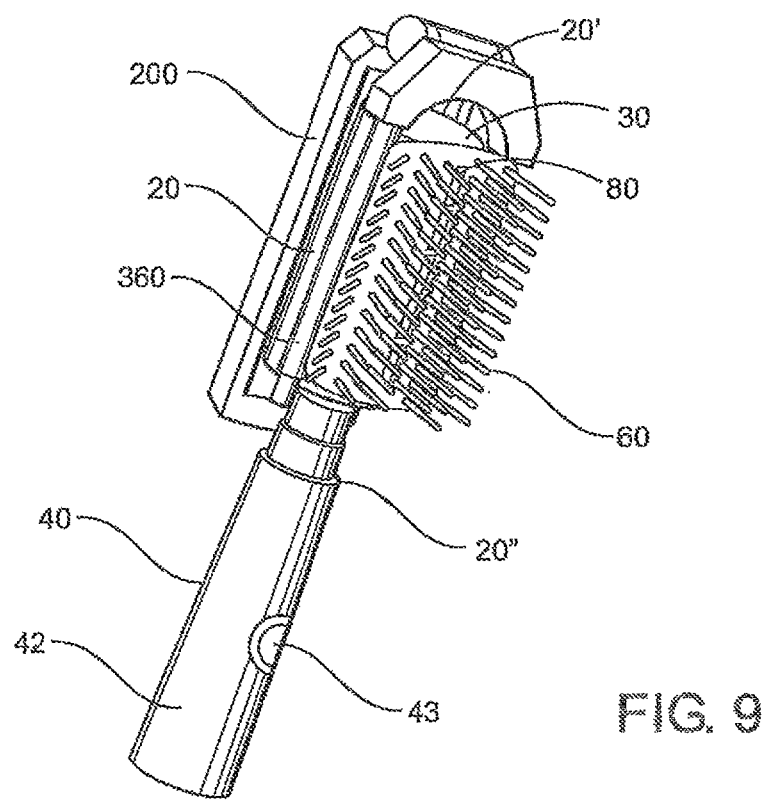
FIG. 9 is a perspective view of the inventive device in one possible embodiment having a single central housing, and with at least two connecting members, each disposed on an opposite side of the central housing and structured to receive the mirror attachment, sufficient to removably secure the mirror attachment to the inventive device.

Comparatively, in one of the other preferred embodiments with one central housing 20 as shown in FIGS. 9 and 10, the central housing 20 has at least two connecting members 360. As such, each of the two connecting members 360 are structured to receive at least a portion of the mirror attachment 200, sufficient to removably secure the mirror attachment 200 to the inventive device 10. Alternatively, in one of the embodiments, the mirror attachment 200 can also be permanently affixed to the housing so as to avoid any detachment.

Figure 13:
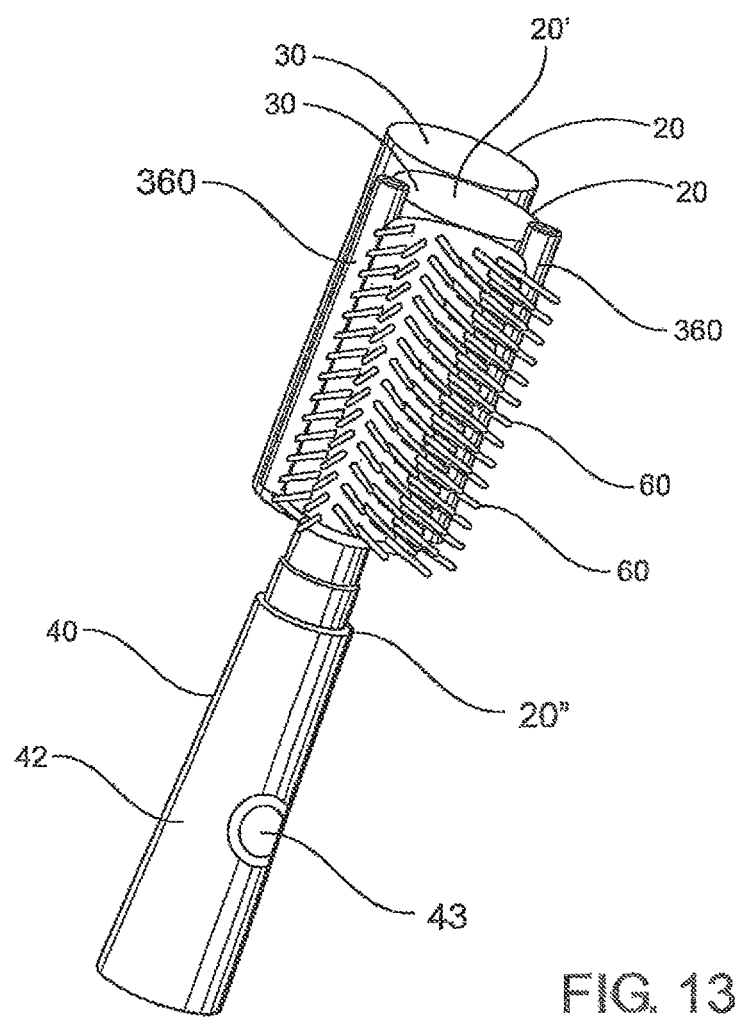
FIG. 13 is a perspective view of the inventive device illustrating two housings with the handle (which may comprise and/or include a base) removably attached to at least one of the two housings according to one of the preferred embodiments.

Referring now to FIG. 13, in another embodiment the inventive device 10 may include no more than two housings, such as a first central housing 20 and a second housing 20'. Each of the two housings 20 and 20' may be structurally and functionally similar, if not identical, to the ones described in earlier embodiments. Accordingly, one of the two housings 20, 20' has the plurality of bristle elements 60 attached thereto. Additionally, given this embodiment, it will be appreciated by those skilled in the art that at least one cartridge or cartridge assembly 120 inserted in one of the two housings 20 or 20', contains the hair building material in wet form, whether gel-like or another form, while at least one cartridge or cartridge assembly 120 inserted in the other of the two housings 20, contains the hair building material in dry form, such as powder, fiber-like strands etc. As such, the processing, blending and dispensing of the hair building materials in this embodiment of the device 10 with two housings 20 and 20' works substantially identical to the aforementioned preferred embodiments. Additionally, in this embodiment, and as shown in FIG. 12, the base 40 and/or handle 42 has the movable member 100 mounted thereon, and is removably connected to one of the two housings 20, 20'. As a result, similar to the operational features described in one of the preferred embodiments described earlier herein, the hair building material contained in one of the cartridges 120 inserted in one of the two housings 20, 20' is penetrated by the movable member 100, sonically blended by the vibration, and dispensed for blending with the hair building material contained in one of the other cartridges 120 inserted in the other of the two housings 20, 20', and substantially concurrent application to the hair and/or scalp of the user. As a result, the hair building material contained in each of the cartridges 120 and in each of the two housings 20 and 20' collectively may simultaneously dispensed and blended at the user's hair, when the inventive device 10 is in operative use.

With reference now to FIGS. 9 and 10, the inventor herein also contemplates that the inventive device 10 may include only one housing 20. In this additional preferred alternative embodiment, and as shown in FIG. 12, the inventive device 10 comprises a base 40 and/or handle 42 with a movable member 100 and a central housing 20 with plurality of bristle elements 60 connected thereto. As such, the user connects the housing 20 with the bristles to the base 40 and/or handle 42, which has the movable member 100 mounted thereon. To illustrate this further, as the user attaches the housing 20 to the base 40 or handle 42, the movable member 100 is structurally received within an inner cavity or the interior hollow chamber of the housing 20. As such, the inner cavity of the housing 20 is sized, structured and configured to receive the movable member 100 so as to ensure a secure fit. Similarly, as in earlier preferred embodiments, the movable member 100 is structured to vibrate and/or oscillate at a frequency that allows the entire inventive device 10 to vibrate as well. As such, the movable member 100 is connected to a power supply that ensures its vibration when actuated. Additionally, and while not shown in any particular Figure exclusively, the user frictionally attaches the cartridge or cartridge assembly 120 containing hair building material(s) in the housing 20 from the open end 20'.

In one embodiment, the cartridge assembly may be structured to include a pair of interior chambers with one type of hair building material, such as in a wet form, contained within one chamber and another type of hair building material, such as a dry form, contained within the other chamber. FIG. 17 illustrates one example of such a "dual" cartridge assembly and will be described more in detail below. As such, even in this additional alternative embodiment, as in others previously illustrated, the movable member 100 will preferably vibrate so as to cause the plurality of bristle elements 60 to also vibrate as the user applies the hair building material on his or her hair. As a result, and similar to the operational features mentioned in embodiments earlier, the hair building material contained in at least one interior chamber of the cartridge 120 inserted into the housing 20 is penetrated by the movable member 100, sonically blended by the vibration, and dispensed for blending with another hair building material contained within another interior chamber of the cartridge 120, and application directly on to the user's hair and/or scalp as one complete blend of the hair building material with all the ingredients necessary to promote hair building attributes on the user's scalp. Therefore, it may be appreciated by a person skilled in the art that the hair material contained in the cartridge 120 within the housing 20 will be blended within the cartridge 120 as a complete solution, before it can be dispensed collectively as hair building material comprising of all the ingredients necessary to promote hair building attributes onto the user's scalp/hair, when the inventive device 10 is in operative use.

Figure 15:
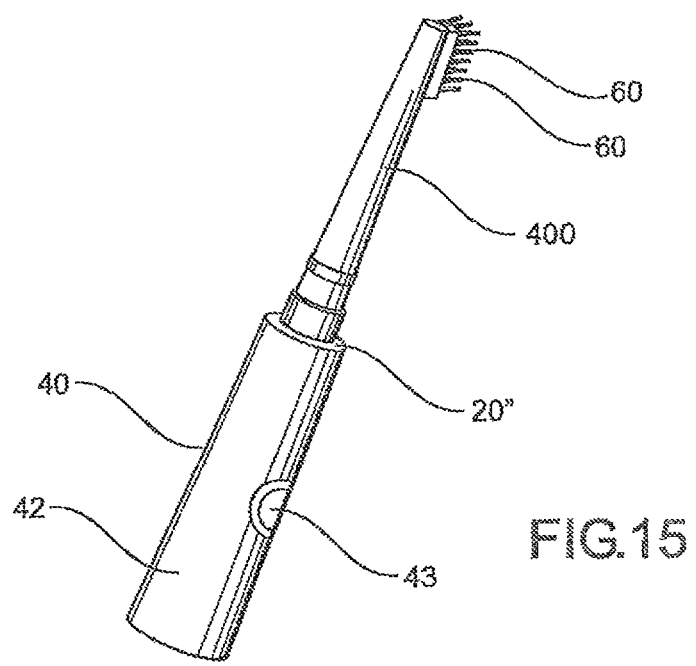
FIG. 15 is a perspective view of the inventive device illustrating the handle (also referred to herein at times as a base) attached to a movable member and bristle holder including a plurality of bristles attached thereto, according to another one of the preferred embodiments.

With reference now to yet another one of the other preferred embodiments, and as shown primarily in FIG. 15, the inventive device 10 has the base 40 and/or handle 42 connected to a bristle holder 400 with the plurality of bristle elements 60 attached thereto. However, it will be noted that in this preferred embodiment, the inventive device 10 does not include any housings 20. As such, the user securely connects bristle holder 400, to the base 40 or handle 42, which has the movable member 100 mounted thereto. To illustrate this further, as the user attaches the bristle holder 400 on to the base 40, the movable member 100 mounted on the base 40 is structurally received within an inner cavity of the bristle holder 400. As such, the inner cavity of the bristle holder 400 is sized, structured and configured to receive the movable member 100 so as to ensure a secure fit. Similarly, as in earlier preferred embodiments, the movable member 100 is structured to vibrate and/or oscillate at a frequency that allows the entire inventive device 10 to vibrate as well. As such, the movable member 100 is connected to a power supply that ensures its vibration when actuated. To further illustrate the operational features in this embodiment, the user simply dips the plurality of bristles 60 in each of the hair building material contained in an external container and applies it directly on the scalp and/or hair. However, it is equally important to note that in this preferred embodiment, the movable member 100 vibrates so as to ensure that the plurality of bristles 60 vibrate, as the user applies the hair building material on the hair and/or scalp.

With reference now to FIG. 7, in yet another and alternative embodiment, the device 10 of the present invention can comprise a compression member. It will be noted that in this embodiment, the first central housing 20 is absent the inclusion of the movable member 100. Instead, the compression member may be connected to the first central housing 20 within the hollow interior chamber 30 therein, and possibly in coaxial alignment therewith. Furthermore, the compression member is sized, structured and configured to connect a selected cartridge disposed therein, including the first cartridge 120 or the second cartridge assembly 170. As represented in FIGS. 6 and 7, and as used, a user inserts a selected cartridge, such as the second cartridge assembly 170 containing a portion of the hair building material. The second cartridge assembly 170 is securely connected to the compression member with a predetermined amount of force by the user, sufficient to allow the second cartridge assembly 170 to connect, secure, and remain affixed therein. As a result, the pressure exerted in connecting the second cartridge assembly 170 to the compression member causes one or more ingredients of the portion of the hair building material contained in a corresponding one of the supplies or cartridges of hair building material to flow out of and through a corresponding access opening, through and along the flow path comprising the plurality of pathways 80 in the first housing 20, onto the plurality of bristle elements 60.

It is noted at this juncture that the inventor herein contemplates other embodiments for the compression member, including as an example, that illustrated in FIG. 22-C and which will be described more in detail below.

Additionally, in one embodiment of the device 10 of the present invention, as illustrated in FIG. 3, the first cartridge assembly 120 or the second cartridge assembly 170 can be connected to a sleeve member 240 having a sleeve cap 240'. The sleeve member 240 is sized, structured and configured to secure at least a portion of a different one of each of the cartridge assemblies 120, 170, etc. As such and by way of example, the sleeve member 240 and the second cartridge assembly 170 are secured to each other, sufficient to ensure that the access opening 172 remains exposed to allow one or more ingredients of the hair building material contained in the second cartridge assembly 170 to flow out freely. Therefore, as an illustration and as shown in FIG. 3, the second cartridge assembly is 170 is securely connected with the sleeve member 240. Then, as shown in FIG. 4, the second cartridge 170 is inserted into the second housing 160 and/or the third housing 210 of the inventive device 10. The sleeve member 240 and the sleeve cap 240' can aid the user to rotationally align the second assembly cartridge 170 when disposed into one of the housings 160, 210, by manipulation of an exteriorly accessible member 240'. Alternatively, however, the second cartridge assembly 170 can be free of any connections, like the sleeve member 240, and inserted directly and then rotated so that the access opening 172 is in alignment with the plurality of pathways, such as 180 in the second housing 160.

Furthermore, it will be appreciated by those skilled in the art that in one of the preferred embodiments, the inventive device 10 includes various detachable components and arrangements. For example, the mirror attachment 200 may be removably attached to at least one housing, such as central housing 20 having the plurality of bristle elements 60 attached thereto as shown in FIG. 9. As another example, the mirror attachment 200 and the central housing 20 with bristle elements 60 can be collectively detached from the base 40 or handle 42, as shown in FIG. 11. For instance, and as described previously herein, to attach the base 40 or handle 42 to the housing 20, the user may execute a counter-clockwise rotation of the base 40 relative to its connection to the housing 20. The counter-clockwise rotation allows the base 40 to engage to the housing 20, and attach itself thereto. More particularly, as shown in FIG. 12, as the base 40 or handle 42 is secured to the housing 20, with the movable member 100 mounted on the base 40 being substantially received within the hollow interior chamber 30 of the housing 20, so as to ensure a secure fit. Additionally, in this preferred embodiment, the central housing 20 has a first open end 20' and a second open end 20''' as shown in FIG. 11. However, when the base 40 or handle 42 is secured to the housing 20, the second open end closes to form a closed end 20'' as shown in FIGS. 9 and 10.

Comparatively, when detaching the base 40 or handle 42 from the housing 20, the base 40 or handle 42 may be rotated in a clockwise direction relative to the housing 20. The clockwise rotation allows the base 40 or handle to disengage from the housing 20, and detach thereof. More particularly, as the base 40 is detached from the housing 20, the movable member 100 mounted is released from its secure fit in the hollow interior chamber 30 of the housing's open end 20''' as shown in FIG. 11. Additionally, the closed end 20'' of the housing 20 is re-opened as the second open end 20'''. To further illustrate this preferred embodiment in a detailed manner, the base 40 or handle may be secured to the housing 20 during attachment by a retention member no disposed on the movable member 100. As a result, when the base 40 is rotated in the counter-clockwise direction relative to the housing 20 and inserted therein, the retention member no disposed on the movable member 100 and positioned inside the housing 20, secures the base 40 to the housing 20, sufficient to illustrate the inventive device 10 as a one piece construction. Alternatively, as the base 40 is turned in the clockwise direction relative to the housing 20, the retention member unlocks and releases the base 40 from the housing 20, sufficient to illustrate the inventive device 10 as a two piece construction, one being the base 40 and the other being the combination of the mirror attachment 200, the housing 40 and the plurality of bristles 60 attached thereto.

Figure 14:
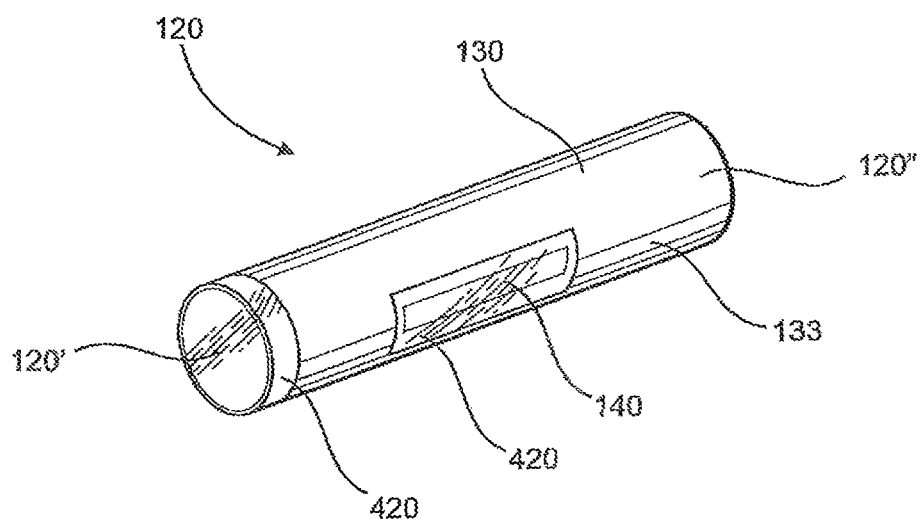
FIG. 14 is a perspective view of a cartridge with an open and closed end, and a sealing member disposed to seal the open end and the access opening of the cartridge according to one of the preferred embodiments.

Furthermore, in one of the preferred embodiments of the inventive device 10, the cartridge or cartridge assembly 120 may not necessitate a penetrable closed end 120'' as shown in FIG. 5. More specifically, and as shown primarily in FIG. 14, the cartridge 120 may have a closed end 120''' and an open end 120' that is sealed with a sealing member 420 before the cartridge or cartridge assembly 120 is operationally put to use. To further illustrate this, the user may peel off or remove the sealing member 420 as the cartridge 120 is ready to be inserted within one of the housings. Similarly, in the relevant embodiments, the access opening, slit or incision 140 on the cartridge 120 assembly may also be sealed with the sealing member 420. To further illustrate this, the user can peel or remove the sealing member 420 off the access opening, slit, or incision 140 of the cartridge assembly 120 as it is ready to be inserted into the housing 20. Alternatively, in one of the preferred embodiments, the user may simply peel off the sealing member 420 on the access opening 140, but retain the sealing member on the open end 120'. As such in this embodiment, the movable member 100 may initiate contact and penetrate the sealing member 420 on the open end 120' when the cartridge 120 is inserted into the hollow interior chamber 30 of the housing 20, and thus, ensure its exposure with the hair building material contained therein.

With reference now to FIGS. 16 and 17, an improved cartridge assembly is illustrated for use with the device 10 and 1000 of the present invention, and will now be described relative to one or more alternative embodiments.

More specifically, and as shown in FIG. 16, an improved cartridge assembly is illustrated in one embodiment as 1120, which may be described as a second cartridge assembly. The improved cartridge assembly is structured to carry and dispense a hair building material or hair care product, intended to be a dry material, but not necessarily limited to the same, while disposed within an auxiliary housing, such as 1070 or 1080, associated with the device 1000 and described in detail further below. As shown in FIG. 16, the improved cartridge assembly 1120 comprises a sleeve 1121 and a separate cartridge 1125, that is carried within the sleeve 1121. As also shown in FIG. 16, the sleeve 1121 has an open first end 1122, an open second end 1123, and a hollow interior extending therebetween defined by a sidewall 1124. In addition, the sidewall 1124 of the sleeve 1121 includes at least one opening 1124*a* formed within it, but preferably, a plurality of openings such as at 1124*a*, 1124*b*, 1124*c*, in fluid flow communication with the hollow interior thereof, with each opening 1124*a*, 1124*b* and 1124*c* formed as a slit and that collectively, extend in a linear array between the first open end 1122 and second open end 1123 of the sleeve. The separate cartridge 1125 has a first end 1127 which should be partially, if not fully closed, an oppositely disposed and closed second end 1128, and at least one opening 1129*a*, formed in the body 1129 defining the cartridge 1125 that extends between said ends 1127 and 1128 thereof. Preferably, however, the separate cartridge 1125 includes a plurality of openings 1129*a*, 1129*b*, 1129*c* each of which, as shown in FIG. 16, is formed as a slot and that collectively, also extend in a linear array between the first end 1127 and second end 1128 of the cartridge 1125. These openings in the cartridge 1125 may be sealed initially as described previously herein with regard to the cartridge(s) illustrated in FIGS. 3 through 5 and/or 14, but do not have to be.

In addition, the sleeve 1121 of the improved cartridge assembly 1120 shown in FIG. 16 is cooperatively structured, sized and configured to receive the cartridge 1125 within its hollow interior. Accordingly, the inner diameter of sleeve 1121 is larger than the outer diameter of the cartridge 1125. While the cartridge 1125 may be snugly received within the hollow interior of the sleeve 1121, the outer diameter of the cartridge 1125 is sized to permit at least some rotation of the cartridge within the sleeve 1121, which may be accomplished by a manipulation of a ridged surface or knob 1126 formed at end 1127 of the cartridge 1125. The ability to rotate the cartridge 1125 within the sleeve 1121 allows for the opening 1129*a* or plurality of openings/slots 1129*a*, 1129*b* and 1129*c* of the cartridge to be fully aligned or if desired, partially aligned, with the slits 1124*a*, 1124*b* and 1124*c* of the sleeve 1121 to permit selective distribution of the hair building materials or other hair care material(s) carried within the cartridge 1125. Similarly, the cartridge 1125 can be selectively rotated within the sleeve 1121 so that the openings/slots 1124*a* to 1124*c* do not align with the slits 1124*a* to 1124*c*, which serves to close these openings and prevent any further distribution of the materials carried within the cartridge. To assist with alignment and smooth rotation of the cartridge 1125 within sleeve 1121, the cartridge 1125 can include a small nub 1130 that is sized and configured to be received within a track 1132 or groove formed within the sidewall 1124 of the sleeve 1121 as shown in FIG. 16.

With reference now to FIG. 17, yet another improved cartridge assembly 1220 is illustrated for use with the device of the present invention, such as but not limited to the device 10 shown in FIGS. 4, 6 and 7, and also, device 1000 shown in FIG. 22 and described further below. While this cartridge assembly 1220 is somewhat similar to that shown in FIGS. 3 through 5 and can be referred to as a first cartridge assembly, it comprises a single tube 1221, having two chambers 1222 and 1226 structured to carry and dispense both a dry material and a wet material. In an additional embodiment, a separate "mini" cartridge 1225 can be received for use within one of the chambers, such as 1226. This cartridge assembly 1220 is particularly structured to carry different types of hair building material, such as a gel or other wet material in chamber 1222 and a powder or other type of dry material in chamber 1226, whether alone, or ideally within a separate mini cartridge 1225 as described herein. Thus, the improved cartridge assembly 1220 of FIG. 17 allows for both wet and dry forms of hair building material to be carried in one sleeve or tube, but also without allowing these materials to come into contact with each other, until such time as that is desired.

To that end, and still referring to FIG. 17, chamber 1222 of the sleeve 1221 may comprise a first end 1223*a* and an oppositely disposed closed end 1223, defined by an interior wall 1224 within the tube or sleeve 1221. The open end 1223*a* of chamber 1222 will preferably be closed with a heat seal or other membrane (not shown) that can be punctured, such as by a penetrating tip 1034 of a handle 1042 of the device 1000, when the device is about to be used, i.e., when there is a new supply of hair building material in the chamber 1222, as described further herein. Chamber 1226 may also have a closed end 1227, such as defined by the interior wall 1224 within the tube 1222, and an open opposite end 1228, and further, may include at least one opening, such as slot 1229. However, in another possible embodiment, the end 1227 may also be closed with a heat seal or other membrane so that an elongated puncturing tip 1034 can penetrate through it and into chamber 1226 as well, for purposes described herein relating to the mixing of the hair building materials or other hair care products carried within both chambers 1222 and 1226 and/or mini cartridge 1225.

Still referring to FIG. 17, a separate and smaller sized "mini" cartridge 1125 may be snugly received within the hollow interior of the chamber 1126, with the outer diameter of the cartridge 1225 also being sized to permit at least some rotation of the cartridge within the upper chamber 1226 of tube 1222. This may be accomplished by manipulation of a ridged surface 1230 formed at the outer end of the cartridge 1225. The ability to rotate the mini cartridge 1225 within the upper chamber 1226 of tube 1222 allows for the opening 1232 of the mini cartridge 1225 to be fully aligned, or if desired, partially aligned, with the slot 1229 of the upper chamber 1226 of tube 1222 to permit selective distribution of the hair building materials (or other hair care material(s)) carried within the cartridge 1225. To assist with alignment and smooth rotation of the cartridge 1225 within tube 1222, the mini cartridge 1225 can include a small nub 1235 that is sized and configured to be received within a track 1237 or groove formed within the sidewall of the tube's upper chamber 1226, as shown in FIG. 17. Similarly, the mini cartridge 1225 can be selectively rotated within the tube's upper chamber 1226 so that the opening 1232 does not align with the slit 1229, so as to lose these openings and no longer permit any further distribution of the materials carried within the cartridge 1225. The mini cartridge 1225 is well suited for carrying a dry type of hair building material, such as but not limited to a powder. Also, in some embodiments, a plug 1240 can be inserted into the open upper end of the tube's mini cartridge 1225 to close it and prevent any of the material from exiting or leaking out of the cartridge 1225 and chamber 1126. A similar plug 1240 can be used in some embodiments to close the open end of cartridge 1125 shown in FIG. 16.

In addition, the improved cartridge assemblies of the present invention, such as those shown in FIGS. 16 and 17, but including other embodiments, may be made from a waterproof material, such as plastic, but ideally one that is also bio-degradable. For example, in at least one embodiment, the cartridge assembly 1120 and/or 1220 is made of Polylactic Acid (PLA) so as to offer a suitable shelf life of two years or more, but which can degrade whether in a landfill, in the ocean, composting facility etc. Thus, the improved cartridge(s) described herein may be readily disposable. Moreover, in at least one embodiment, a resin using polybutylene adipate terephthalate (PBAT), such as that made by the European (German) company known as BASF, S.E., is added to the PLA as part of the composition used to form the improved cartridge assemblies 1120 or 1220. Further, in certain embodiments of the invention wherein the hair building material(s) carried by the cartridge includes keratin proteins, one or more components of the Polylactic Acid (PLA) may interact with the keratin over time and soften them, and may thereby assist with the hair building process, in that such further softened material should help to form a phyto-skeleton on an existing strand or strands of hair. Additionally, in certain embodiments of the cartridge, which can be called "Bio-Active" polymer," the materials used to construct it may biodegrade into lactic acid internally, and sonically infuse trace amounts into the formula of hair building material(s) carried by the cartridge, which act as a catalyst to activate the formulation into fiber strands. Also, because the inventive device 1000 is structured to allow for concurrent blending of the formulations of first and second supplies of hair building materials, phyto-skeletal hair color strands may also be produced.

Further, the lactic acid from the "Bio-Active" cartridges, as noted above, can bond, link and soften the "dry" multi-dimensional cellulosic fiber compounds together, also forming strands, by the sonic activation of the brush. These cellulose fiber strands may therefore comprise a compound of pulverized particles of different sizes (e.g., of anywhere from 5-900 microns), which allow molecular penetration into and/or under the cuticle scales of the hair, and branch out, thickening and thereby, creating fuller scalp concealment and a more permanent bond than what is known with prior art hair fiber compounds. The "wet" or gel portion of the secondary compound is bonded and linked together by the bio polymers in the gel, reacting to the lactic acid and the sonic activation, which is then molecularly aligned by the sonic mechanical sheer stress of the central housing or cylinder and other components of the brush device forming fiber strands.

Also, and as set forth above, the present invention may also include an inventive composition or formulation for the aforementioned hair building material(s) usable with the device 10 of the present invention, or variations of such composition(s) and formulation(s) and/or other formulations. The inventive device is thought to be unique in that, among other things, different portions of the hair building material(s) may be disposed in the different first, second and third cartridges, with the ability to apply a vibratory force to the same, for concurrent delivery from the cartridges and through various structures and openings in the device, to the plurality of bristles 60 where the different portions of the hair building material are substantially blended together during use of the device for application of such materials(s) onto a user's scalp and/or hair.

The preferred and unique composition of the hair building material to be used in the inventive device 10 and/or 1000 comprises at least a first portion in the form of the aforementioned wet, liquid and/or gel-like material, which may also contain a plurality of bio-active polymeric materials. The gel-like material may contain organic lignin polymers and polysaccharide chains, such as but is not limited to, *Aloe ferox* and *Aloe barbadensis* Leaf along with Cellulose and Keratin protein fiber. The Cellulose and Keratin protein fiber can help in the formation of the bio-active polymeric structure, which facilitates the binding together of at least some portions of the ingredients of the hair building material. In this regard, the gel-like material is preferably contained in the first cartridge assembly or in the improved cartridge assembly 1220 shown in FIG. 17, such as in the larger chamber of tube 1221 between end 1222 (which as described previously may sealed with a membrane that can be punctured prior to use) and divider wall 1223. As such, the cartridge assembly 120 or 1220 containing the gel-like material is also preferably inserted in the central housing 20 and subject to the vibratory force from movable member 100, as set forth above. Additional ingredients of the hair building material can also include: Decolorized *Aloe barbadensis*, Lemon, Cotton Cellulose, Iron Oxides, $CO_2$, Phenoxyethanol/Capryl Glycol/Sorbic Acid, Apple Cider Vinegar, Citric acid, Arrowroot Powder, Xanthan Gum, Keratin protein, Dimethicone, Coconut Oil, Tea tree oil, Rosemary Oil, Argan Oil, Black Castor Oil, Maltodextrin, Epsom Salt, Himalaya Salt, Silk Amino Acids, Caffeine, Cannabidiol (CBD), Hemp Extract, and further, for dry hair building materials can include: Activated Charcoal, Potato Starch, #2 baking soda, sodium acid pyrophosphate and Amla Powder.

In addition, one or more ingredients of the hair building material can also contain other secondary ingredients such as water, glycerin, carbomer, polysorbate 20, PVP, Aminomethyl Propanol, Methylparaben, Fragrance, Glyceryl, Polymethacrylate, Rahnella and Soy Protein Ferment, Propylene Glycol, Peg 8, Palmitoyl, Tripeptide-1, Keratin Amino Acids, Panthenyl Ethyl, Ether, Diazolidinyl, Urea, Potassium Sorbate, Tetrasodium EDTA, Methylchloroisothiazolinone, Methylsothiazolinone, and Benzophenone-4 Blue 1 and Violet 2. Additional ingredients may be: whole oranges, whole cucumbers, soybean, sugarcane, hyaluronic acid, lactobacillus, lactic acid, polyquaternium-4, sodium benzoate, witch hazel, Pantenol $B_5$, Vegetable emulsifying wax, Ethelhexyl stearate, I Ethelhexyl palmitate, hydrogenated olive oil unsaponifiables; and Potassium cocoate.

Furthermore, the hair building material can utilize 150-200 minerals, enzymes, vitamins, and amino acids to promote hair building characteristics. As such, the secondary ingredients may not be limited to any particular known combination of polymeric materials known in the industry. Given this, the hair building material can be processed in combination with all the necessary ingredients for the desired bonding effect onto the hair and the hair scalp. Accordingly, some portion of the secondary ingredients of the hair building material are contained in the second cartridge assembly 170 collectively and/or individually. In this regard, the hair building material in the second cartridge assembly 170 can be formed of a dry powder blend comprising some portions of the hair building ingredients. Likewise, the second cartridge assembly 170 and/or a third cartridge 310 can also contain the hair building material in the form of fibers that resemble hair like strands and/or fiber segments comprising one or more ingredients of the hair building material.

With reference now to FIGS. 18 through 30, the inventive dispensing device 1000 for storing and dispensing hair building materials is illustrated in yet one or more additional preferred embodiments. As described previously herein with other embodiments, the inventive device 1000 is preferably structured to store, process and dispense different types and/or portions of hair building materials, with some types of hair building material having a wet form, such as a liquid or gel-like form, and other types of hair building material having a dry form, such as powder, granular, fiber strands, etc. Thus, in certain embodiments of the inventive device disclosed herein these materials are stored separately from each other, but are dispensed either concurrently, or substantially concurrently, and so as to allow for blending of these materials at the plurality of bristle elements, and concurrent with the application of the blended materials to the scalp of a user. It will also be appreciated from the description which follows that the inventive device 1000 is readily structured to store and dispense other types of hair care products, including but not limited to, shampoo, conditioning treatments, coloring agents and the like, regardless of whether in liquid, cream or another "wet" form, or alternatively, in dry form.

Accordingly, and with initial reference now to FIGS. 18-A and 22, the inventive device 1000 is illustrated in yet another embodiment and includes a base 1040, comprising a central housing 1050 constructed of a rigid material and formed to have a hollow interior 1050'. As illustrated in FIG. 22, the central housing 1050 is ideally cylindrical in shape, and while it may assume other shapes, it is sized, structured and configured to receive, within its hollow interior chamber 1050', a cartridge or a cartridge assembly, such as but not limited to that shown in FIG. 17, containing one or more types of hair building material. As shown in FIG. 18-A, the central housing 1050 also includes at least one opening 1055, such as a single elongated slit as shown, or alternatively, a plurality of openings, formed completely through the sidewall of the housing 1050 into the interior chamber 1050'. For reasons that will be explained further below, in this embodiment of the base 1040, the one or more openings 1055 in the central housing 1050 face outwardly and define a plurality of pathways that allow for fluid flow communication of the hair building material(s) onto a bristle assembly 1060 having a plurality of bristle elements 1068.

Figure 23A:
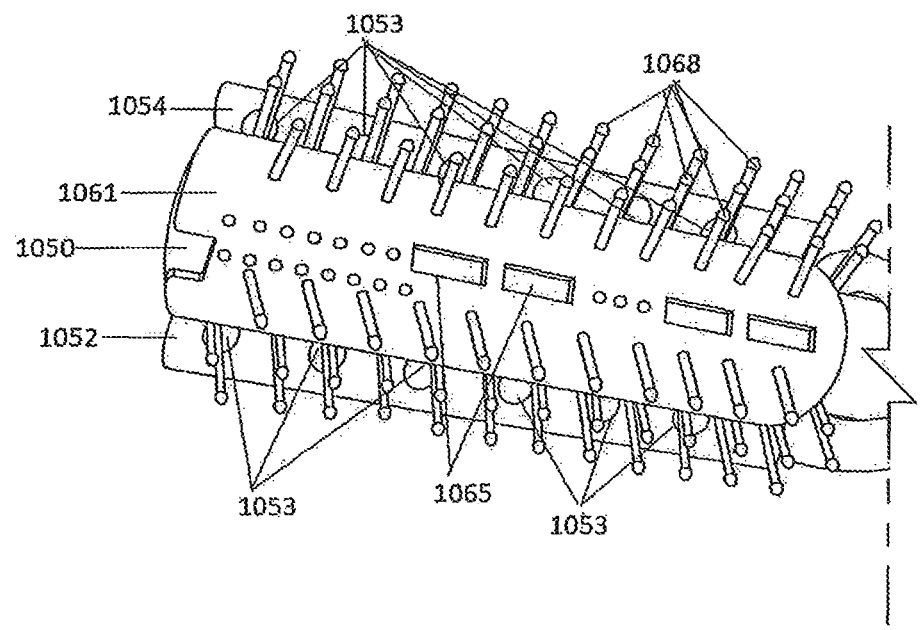
FIG. 23-A is a bottom, close-up view of the inventive device shown in FIG. 22, and illustrating several openings associated with the bristle assembly as well as the base or central housing.
Figure 23B:
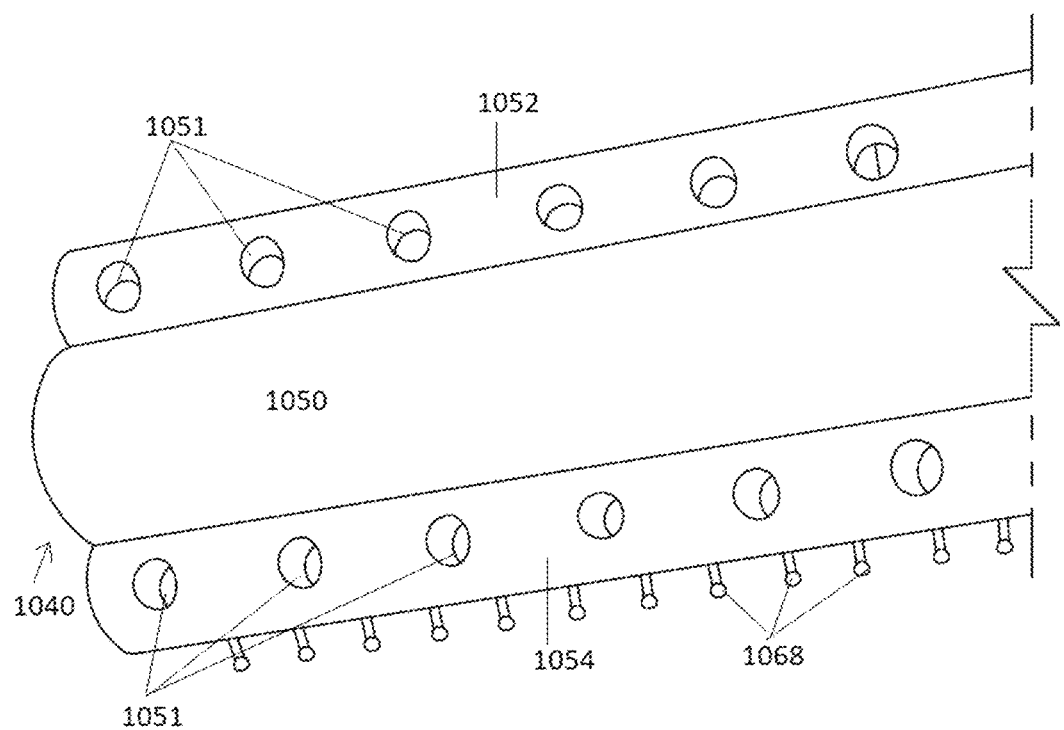

More specifically, and as perhaps best shown in FIG. 23-A the inventive device 1000 additionally comprises a bristle assembly 1060 joined to the base 1040, In at least one embodiment, but not necessarily in others, the bristle assembly 1060 is at least partially flexible and further, is removably joined to the base 1040. For example, in the illustrated embodiment of FIGS. 18-A and 22, the base 1040 additionally comprises a first retaining channel 1052 and a second retaining channel 1054, each disposed on an opposite side of the central housing 1050. In this illustrated embodiment, each of the first and second retaining channels 1052 and 1054 has a hollow interior and also, is preferably cylindrical in shape, yet smaller in size than the central housing 1050. Ideally, each of these retaining channels 1052 and 1054 is also disposed in substantially parallel relation to the central housing 1050, and further, each also has a plurality of openings formed therein, which as shown in FIG. 18-A, extend longitudinally across the channels 1052 and 1054 in spaced apart, and substantially parallel relation to the opening 1055 formed in the central housing 1050 of the base 1040.

Figure 19:
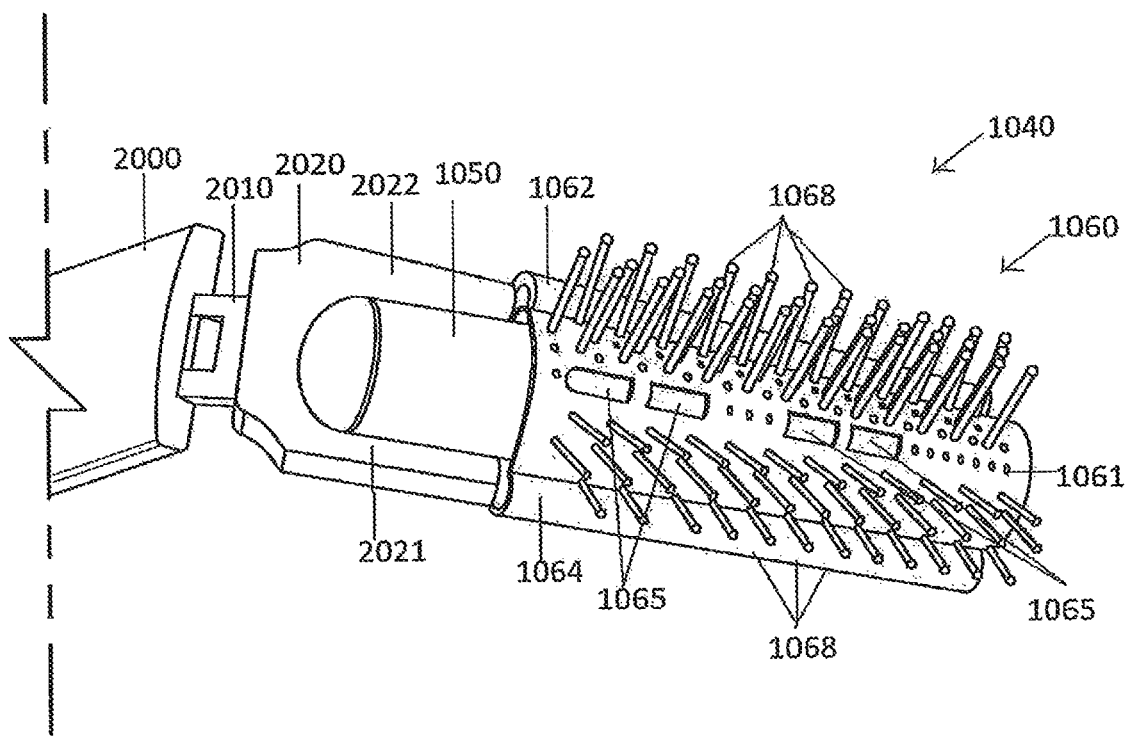
FIG. 19 is a perspective view of the inventive device shown in FIG. 18, but illustrating a side thereof having the bristle assembly associated with the device, as well as the mirror attachment in an open orientation.
Figure 19A:
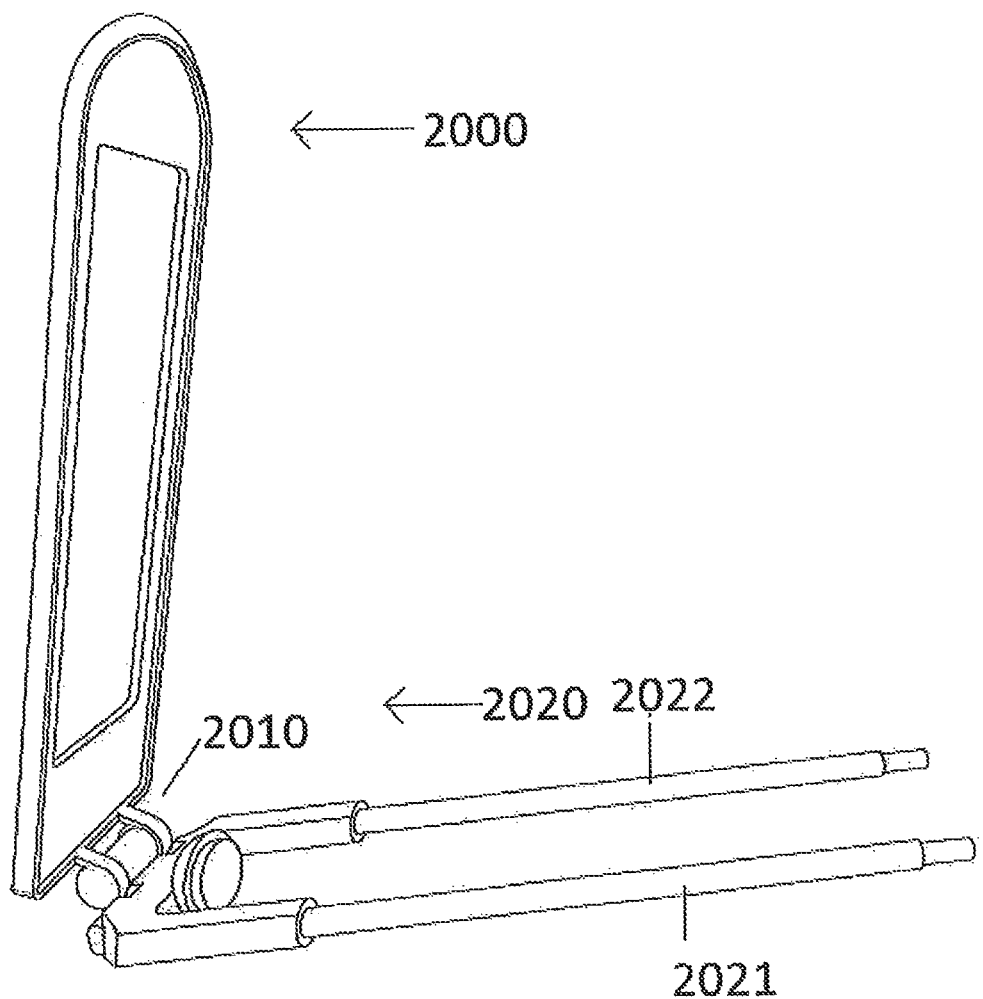

As shown in the illustrated embodiment of FIG. 22, the bristle assembly 1060 comprises a flexible mat 1061, as well as a plurality of bristle elements 1068 connected thereto. Each of the bristle elements 1068 may be formed from a somewhat rigid material and/or with other features described previously herein. The illustrated bristle assembly 1060, as best shown in FIG. 22, preferably also includes a mating structure 1062 and 1064 disposed at each opposite longitudinal end thereof, each of which is sized, structured and configured to be slidably received within one of the hollow interiors of either the first retaining channel 1052 and second retaining channel 1054 of the base 1040. As shown, the flexible mat 1061 and mating structures 1062 and 1064 are preferably sized and structured to closely correspond with the length and width, or overall size of the base 1040. In addition, the flexible mat 1061 includes one or more openings 1065 formed therethrough, as best shown in FIGS. 19 and 23-A, which may comprise a plurality of slots. The size and placement of these openings 1065 within the flexible mat 1061 are preferably strategically selected so as to correspond to the opening(s) 1055 formed in the base 1040. The alignment of these openings is helpful in allowing hair building material, hair color or another hair care treatment carried by a cartridge received within the central housing 1050 to be selectively dispensed by a user from the cartridge, which also has openings as described previously herein, through the aligned openings 1055 and 1065 of the first central housing and the flexible mat 1061, respectively.

It will also be appreciated from FIGS. 19 and 23A, that the flexible mat 1061 of the bristle assembly 1060 will generally be sized and configured to lay across an outer surface of the base 1040 corresponding to and substantially over the exposed and longitudinally extending surface of the central housing 1050, between the first and second retaining channels 1052 and 1054. Further, the flexible mat 1061 is sized and configured to be snugly but removably attached to the base 1040, with one of each of the mating structures 1062 and 1064 thereof, respectively, slidably received and retained within one of the retaining channels, 1052 or 1054, respectively. Accordingly, the flexible bristle assembly 1060 can be slidably maneuvered into place on the base 1040 for use and also, is ideally removable therefrom to allow for cleaning and/or replacement by another or new flexible bristle assembly 1060, if and when that is desired.

With reference now to FIGS. 18, 19 and 19-A, the base 1040 of the device 1000 will, in some embodiments, allow for a mirror attachment 2000 to be mounted thereon. This mirror attachment 2000 is similar to that which was shown as 200 or 200' in FIGS. 2 and 7, and similar to FIG. 6, is illustrated in FIG. 18 as being in a closed or collapsed orientation. That is, mirror attachment 2000 is structured for movement between the closed orientation shown in FIG. 18 and an open orientation shown in FIGS. 19 and 19-A. The mirror attachment 2000 can be structured to pivot or swing from the closed orientation to the open orientation while attached to the base 1040. Ideally, however, this mirror attachment 2000 can be removed from the base 1040 and used separately to assist one with viewing locations on the scalp to which the hair building material should be applied. As such, the mirror attachment 2000 may comprise a hinged body 2010 with a lower portion 2020 that comprises a "U" shaped configuration including pair of legs, 2021 and 2022, as best shown in FIG. 19-A. Each of the legs 2021 and 2022 is sized and configured to be slidably received into and within one of the oppositely disposed, hollow interiors of retaining channels 1052 or 1054 on the base 1050, even with the flexible bristle assembly 1060 mounted on the base 1050. Additionally, the lower portion 2020 may be sized and configured to overlay the open lower end of the central housing 1050 of the base 1040 when the mirror 2000 is attached to the base 1050. It is pointed out that FIGS. 20 through 23-B illustrate the device 1000 with the mirror attachment 2000 removed.

It is also pointed out that the device 1000 shown in FIG. 18 with a folding mirror attachment 2000 is suitable for use as a stand-alone and readily portable device. That is, the inventive device 1000 of FIG. 18 does not include a handle and can receive a single cartridge assembly therein. For example, a cartridge assembly 1120 such as is shown in FIG. 16, but including possibly other cartridges described herein, can be inserted into the base 1050 and interior 1050' of the central housing thereof. This cartridge assembly 1120 is well suited, given its length dimension, for use in the device 1000 shown in FIGS. 18 and 19, and for carrying a hair building material or other hair care product, ideally but not limited to a dry form, such as powder. In at least one embodiment, the device 1000 shown in FIGS. 18 and 19 can be packaged alone and/or sold with several cartridges.

Figure 20:
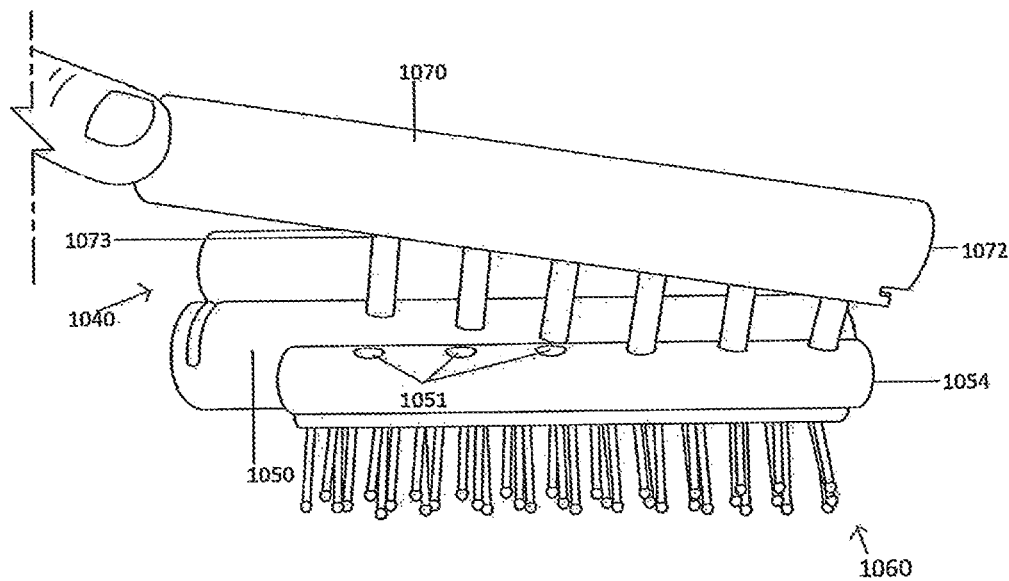
FIG. 20 is a side view of the base shown in FIGS. 18-A, 18 and 19, but with a first auxiliary housing associated therewith being mounted thereon, and no mirror attachment.
Figure 21:
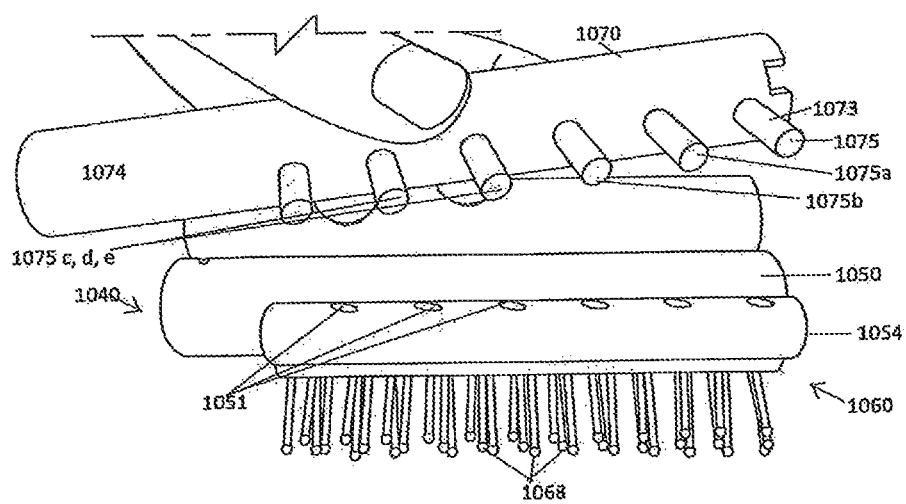
FIG. 21 is a perspective view of the invention shown in FIG. 20 and illustrating a bottom side of the first auxiliary housing.

With reference now to FIGS. 20 through 22, the inventive device 1000 further comprises at least one auxiliary housing 1070 joined to the base 1040. Preferably, and as best shown in FIG. 22, the illustrated device 1000 will comprise a pair of auxiliary housings, 1070 and 1080. Each of the auxiliary housings 1070 and 1080 is preferably constructed of a rigid material and formed to have a hollow interior, which may also be cylindrical in shape. As described below, each of the auxiliary housings 1070 and 1080 is also preferably structured for being removably connected to the base 1040, such as by a joining peg structures 1073, shown in FIGS. 20 and 21. The auxiliary housings 1070 and 1080 are preferably disposed on the base 1040 so as to be in adjacent and substantially parallel relation to the base 1040, as shown in FIG. 22. Additionally, the auxiliary housing 1070, including the second auxiliary housing 1080 if there is one, is sized, structured and configured to receive, within its hollow interior, a cartridge assembly, such as but not limited to that shown in FIG. 16, containing one or more types of hair building material. Consequently, the auxiliary housing 1070 includes at least one open end, such as 1072, to allow access to the hollow interior thereof for insertion and removal of a cartridge or cartridge assembly, or an atomizer sprayer as discussed further herein. Moreover, and to allow for fluid flow delivery of hair building material contained within a cartridge assembly (such as through openings 1124a to 1124c and 1129a to 1129c shown in FIG. 16), the auxiliary housing 1070 also includes at least one opening 1075 formed in the body 1074 thereof, as best shown in FIG. 21. Preferably, however, the auxiliary housing 1070 includes a plurality of openings 1075a to 1075d formed therein as shown in FIG. 21. Also, and as illustrated in FIGS. 20 and 21, each opening such as at 1075 may be positioned at the end of a joining peg structure 1073 connected to the body 1074 of the auxiliary housing 1070, having a hollow interior channel that further comprises a fluid flow path for the hair building material to follow for treatment of a user's hair and scalp.

Still referring to FIGS. 20 and 21, the joining peg structures, such as at 1073 of the first auxiliary housing 1070 are each structured, sized and configured for being matingly attached to another set of openings formed on either the first retaining channel 1052 or second retaining channel 1054 of the base 1040 to supply hair building materials and/or other hair care product(s). More specifically, the first and second retaining channels 1052 and 1054 formed on opposite sides of the base 1040 include a plurality of openings formed therein, such as at 1051 in FIGS. 20-21 and which also extend therethrough, including through the mating structure 1062 of the flexible mat 1061, as shown by openings 1053 in FIG. 23A. As best shown in FIG. 20, the auxiliary housing 1070 can be mounted onto the base 1040 of the device 1000, with the joining peg structure 1073 and openings 1075 in mating alignment with the openings 1051 through to 1053 on the retaining channel 1052 of the base 1040 and thereby, allow the hair building materials or other hair care product to flow out along fluid flow pathway extending from the openings formed in a cartridge assembly, such as 1120, through the auxiliary housing 1070 in fluid communication with the joining peg structure 1073 and the openings 1075, as well as through the openings 1051 and 1053 on the retaining channel 1052, and onto the bristle assembly 1060 for blending and application to a user's scalp. The second auxiliary housing 1080 is similarly disposed on an opposite longitudinal side of the base 1040 and structured to perform in a similar manner relative to the other retaining channel 1054 and openings thereof.

From FIGS. 23-A and 23-B, it will be appreciated that the device 1000 comprising the base 1040 and central housing 1050, including the auxiliary housings 1070 and 1080, and bristle assembly 1060, is structured and disposed to dispense different types of hair building material to the plurality of bristle elements 1068 and along different fluid flow paths, each disposed in spaced apart and generally parallel relation to each other, for being blended by the bristle elements 1068 at the hair scalp of a user during the application process. In one or more embodiments, each of the auxiliary housing 1070, 1080 is also removably attached to the base 1040 to allow for cleaning thereof.

Additionally, it is contemplated and should be considered to be part of the invention to utilize a different type of cartridge with the device 1000. For example, and as shown in FIG. 22-A, an atomizing sprayer could be alternatively used as the cartridge, which would also be structured to be insertable and removable from one of the housings associated with device 1000, preferably such as auxiliary housings 1070, 1080 shown in FIG. 22. Alternatively, a pump sprayer 1420 can be used as the cartridge, as shown in FIG. 22-B. The atomizing sprayer 1320 and/or the pump sprayer 1420 can contain different forms of hair building material or another hair care product, such as liquid, cream, shampoo, conditioning treatments, hair spray or even a body gel or soap. Thus, the hair treatment product within the sprayer cartridge 1420 could be selectively applied by a user either before hair building materials are applied, or more hair building materials are applied, or after. In some instances, the atomizing sprayer 1320 may be aided by sonic vibrations, described further hereinafter, to assist with blending the ingredients of the hair building material or other hair care products in the cartridge together.

Similarly, and with reference now to FIG. 22-C, it should be considered part of the invention to utilize another type of cartridge assembly with the device, such as one having a compression member 5000. More specifically, and as described previously herein, the device 1000 shown in FIGS. 20, 21 and 22 includes at least one auxiliary housing 1070, and preferably two auxiliary housings 1070 and 1080. Each of the auxiliary housings 1070, 1080 may have an open first end and also an open second end. As described elsewhere herein, a cartridge assembly 1220, such as that shown in FIG. 17, and containing hair building material (or if desired, other hair care products) can be inserted into and utilized with the auxiliary housing 1070. With reference now to FIG. 22-C, in an additional embodiment, however, the cartridge assembly can be a cartridge such as 1520, which may not have any openings formed in the sidewall thereof, inserted into and utilized with an auxiliary housing such as 1070 or 1080. This cartridge 1520 may have a first end 1510 that is partially or fully closed, or by way of an example only, this end 1510 may be closed, similar to what has been described relative to the cartridge assembly 1120 shown in FIG. 16, or relative to the mini cartridge 1225 and end 1230 thereof shown in FIG. 17. Additionally, and as shown in FIG. 22-C, this cartridge 1520 may be sized and configured to have a somewhat smaller inner and outer diameter, for purposes which will become clear below. Cartridge 1520 may also have a lower end 1530, which may be closed initially such as by a heat seal, or other type of penetrable material, which may include a sealing, closed cell sponge. Further, and as also shown in FIG. 22-C, the lower end 1530 of the cartridge assembly 1520 may be structured to receive and be operable with a compression member 5000. As shown in FIG. 22-C, the compression member 5000 comprises in a preferred embodiment, a one-piece probe. In this embodiment, the compression member 5000 will preferably also have a hollow interior, and further, will be sized and configured to be inserted within and used with an auxiliary housing, such as 1070 or 1080. In addition, however, the compression member 5000 comprising a probe will also be sized and configured to be inserted within the cartridge assembly 1520 which carries hair building material, typically a wet material. The compression member 5000 in the form of a probe is structured and disposed to penetrate any heat seal or other membrane that initially closes lower end 1530 of cartridge 1520 and is movable into the interior chamber thereof for contact with the hair building material. More specifically, the compression member 5000 in the form of a probe may be manually adjusted and incrementally advanced into the interior chamber of cartridge 1520 for the purpose of applying pressure to and causing a quantity of the hair building material contained therein to flow out of the cartridge 1520 and auxiliary housing 1070. Because it is structured to apply pressure to the contents of the cartridge 1520, as discussed further below, the compression member 5000 is able to disperse the contents more quickly. It is emphasized that the cartridge 1520 can also carry, if desired, another hair care product, such as a shampoo, or a conditioner or a coloring agent, which will typically be in a liquid, gel or cream form, to be delivered to a user's hair and scalp. If desired, this cartridge 1520 could also carry a body soap for dispensing.

Still referring to FIG. 22-C, the compression member 5000 in the form of a probe includes structure for allowing the probe to be incrementally advanced into the cartridge 1520 and to apply pressure to the hair care material contained therein. More specifically, and as shown in FIG. 22-C, the probe may include a threaded section 5010 formed at or near a first end thereof. By way of example, the threaded section 5010 may comprise male threads or a male thread structure. In addition, the internal portion of the auxiliary housing 1070 may also include a threaded structure near one open end thereof, which may be in the form of female threads formed therein which can receive and mate with threaded section 5010 formed on the probe 5000. As also shown in FIG. 22-C, the compression member 5000 in the form of a probe will preferably include an external configuration having a plurality of longitudinally extending grooves 5020 to help the hair building material, or other hair care product, or body soap, as the probe 5000 is manipulated, inserted into the end 1530 of and into the cartridge 1520 disposed within the auxiliary housing 1070, and compression applied to the hair building or other contents within the cartridge 1520, such that flow thereof is facilitated out of the cartridge 1520 and through the pathways of the auxiliary housing 1070 or 1080, i.e., through the peg structures 1073 and openings 1075 and onto the bristle assembly 1060. Additionally, the probe tip can also be foam, plastic, metal or made of a rubber material with either grooves 5020 as shown, or alternatively, pores to help with aligning the polymers of hair building material into fiber strands.

If desired, the compression member 5000 in the form of a probe may additionally include on the hollow interior thereof, a plurality of ball bearings that will further help to facilitate the flow of the hair building materials or other care products when a sonic vibration or other vibratory force is applied to the device 1000, such as through a motor associated with the handle 1042, as described further herein below. More specifically, in an embodiment of the compression member 5000 which includes ball bearings, when a vibratory force is applied to the device 1000, this force will also act upon the inner walls of the compression member and/or probe, which will aid in blending and aligning the various molecular components of the hair building materials, other hair care materials, etc. carried within the cartridge 1520. In at least one such embodiment, the ball bearings are made of a metallic material and sized to be small, such as about 2 mm in diameter, although other ball bearings and/or spheres or similarly shaped members may also be used. Moreover, in at least one further embodiment, the outside walls of the compression member 5000 may be electroplated in copper so that when a vibratory force is applied to the device 1000, a kinetic energy will help to start a reaction that further aids with the contents of the cartridge 1520 being blended or melded together. More specifically, once a vibratory force is applied to the device 1000, it will cause movement of the ball bearings inside of the compression member 5000, and the resulting friction including any heat conveyed thereby should help cause a thermo-conductive reaction that aids with the blending or melding the contents of the cartridge and dispersing of the same through the cartridge and auxiliary housing 1070 and onto the device 1000. Moreover, this thermo-conductive reaction should over time also aid with softening the materials used to form the cartridge itself.

Additionally, yet other embodiments of a cartridge assembly are possible for use with device 10 or 1000. For example, and with reference now to FIG. 22-D, a sprayer cartridge, similar to that shown as 1320 in FIG. 22-A (or a pump sprayer 1420 shown in FIG. 22-B) can additionally include a stirring member 6000. The stirring member 6000 is preferably sized and configured to be carried on a pump mechanism or siphon tube 6040 associated with the sprayer cartridge for drawing the hair care material or other hair care product up from the interior chamber of the cartridge 1320 or 1420 and to the sprayer head 6050 for dispensing. This pump mechanism or siphon tube 6040 may include a point formed at distal end 6045 for penetrating a heat seal or other membrane used to close the cartridge chamber initially. The stirring member 6000 is also preferably sized and configured to be received within and to extend at least partially, but preferably substantially within the longitudinal and lateral confines of the interior chamber of the sprayer cartridge 1320 or 1420, as shown. The stirring member 6000 may comprise a body having a centrally disposed rib or spine 6010, which may be hollow so as to fit over the siphon tube 6040 of pump sprayer 1420 or atomizer sprayer 1320. The body of the stirring member 6000 preferably extends longitudinally between opposite ends thereof, and a pair of tapered flanges 6020 and 6022 extending laterally therefrom, although ideally, the stirring member 6000 includes two pairs of tapered flanges so as to provide the body with a generally "X" or "+" shape in cross section. When the stirring member is manipulated, such as by being rotated within the cartridge 1320 or 1420, the flanges 6020 and 6022 of the stirring member 6000 act as paddles to help move and mix the hair building material or other hair care contents within the cartridge 1320 or 1420 so as to be in more suitable form for dispensing.

Similarly, and still referring to FIG. 22-D, a dual cartridge assembly is shown which may be similar to that shown in FIG. 17, and also is shown as including a stirring member 6000. Thus, two different types of hair care products, or other products can be carried within cartridge 1220, such as one type in tube 1221 and another in mini cartridge 1225. The stirring member 6000 is still preferably configured to be carried on pump mechanism or suction member 6040 associated with the sprayer head 6050 for dispensing, and may also include a point formed at distal end 6045 for penetrating a heat seal or other membrane used to close the mini cartridge 1225 chamber initially, whether at the top open end or bottom open end thereof, or both. Also, the stirring member 6000 is still preferably sized and configured to extend substantially within the longitudinal and lateral confines of the interior chambers of cartridge tube 1221, as the sprayer head is screwed on and into place for use with cartridge 1220, as shown by the directional arrow Y in FIG. 22-D.

With reference now to FIG. 24, the inventive device 1000 further comprises a handle 1042 and a movable member 1032 structured to be operably connected to the base 1040. The handle 1042 includes a first end, all or part of which is suitable for gripping by a user, and an opposite end that is structured and disposed to be mounted to the base 1040. In the preferred embodiments, the handle 1042 is securely but removably attached to the base 1040, such by a suitable friction fit, snap fit or other construction between the intermediate section 1045 and the lower open end of the central housing 1050, similar to that illustrated in FIG. 22. The handle 1042 includes at its opposite end a movable member 1032 that is structured and disposed to be slidably inserted into the open end and hollow interior of the central housing 1050, including into a cartridge assembly 1220 disposed therein and carrying a supply of hair building material or other hair care product. The movable member 1032, which is communicatively linked and responsive to an oscillating mechanism, described below, preferably includes a puncturing tip 1035 at a distal end thereof. The puncturing tip 1035, which in some embodiments is removable and replaceable, is structured and disposed to open the membrane or seal associated with the cartridge assembly, such as tube 1222 and chamber 1221 shown in FIG. 17, carrying hair building materials within it.

Still referring to FIG. 24, in at least one embodiment, the movable member 1032 will preferably also include a plurality of flexible bristle elements 1034, somewhat similar to a toothbrush, as shown. However, the movable member 1032 can assume alternative embodiments, such as a simple probe with a distal end that is suitably rounded or otherwise configured to allow it to enter through a membrane or seal associated with the cartridge assembly, which may be a pointed end but does not have to be. In another embodiment, the movable member 1032 can comprise a compression member, having one or more features that are similar to the compression member 5000 described relative to FIG. 22-C. In should be clear that in such additional embodiments, the movable member can, but does not have to include the small bristle elements shown in FIG. 24.

As also shown FIG. 24, the handle 1042 can include, in some embodiments, suitable structure, such as a spring actuator 1046 for allowing the handle to be quickly but removably attached to the base 1040. Such structure should preferably allow for the handle 1042 to be snugly interconnected with the lower end of the base 1040 and so that subsequent rotation between the base 1040 and handle 1042 is not possible. The handle 1042 also preferably includes a cut-out portion 1043 for receiving a suitable power switch, whether a push-on and off button, or other operating mechanism. Additionally, as described previously herein, and while not shown in the drawings, the handle 1042 carries within it suitable electrical wiring, a motor and a power source, such as a battery and/or super battery. Accordingly, upon activation, the power source provides power to the motor and an oscillating mechanism associated with and to transmit vibrational movement to movable member 1032, enabling sonic oscillation or vibration at a frequency sufficient for the mixing, liquefaction, and distribution of any hair building materials and/or other hair care products, skin care treatments, etc. from within the cartridge assembly and subsequently, onto a user's scalp, hair or skin.

Figure 25:
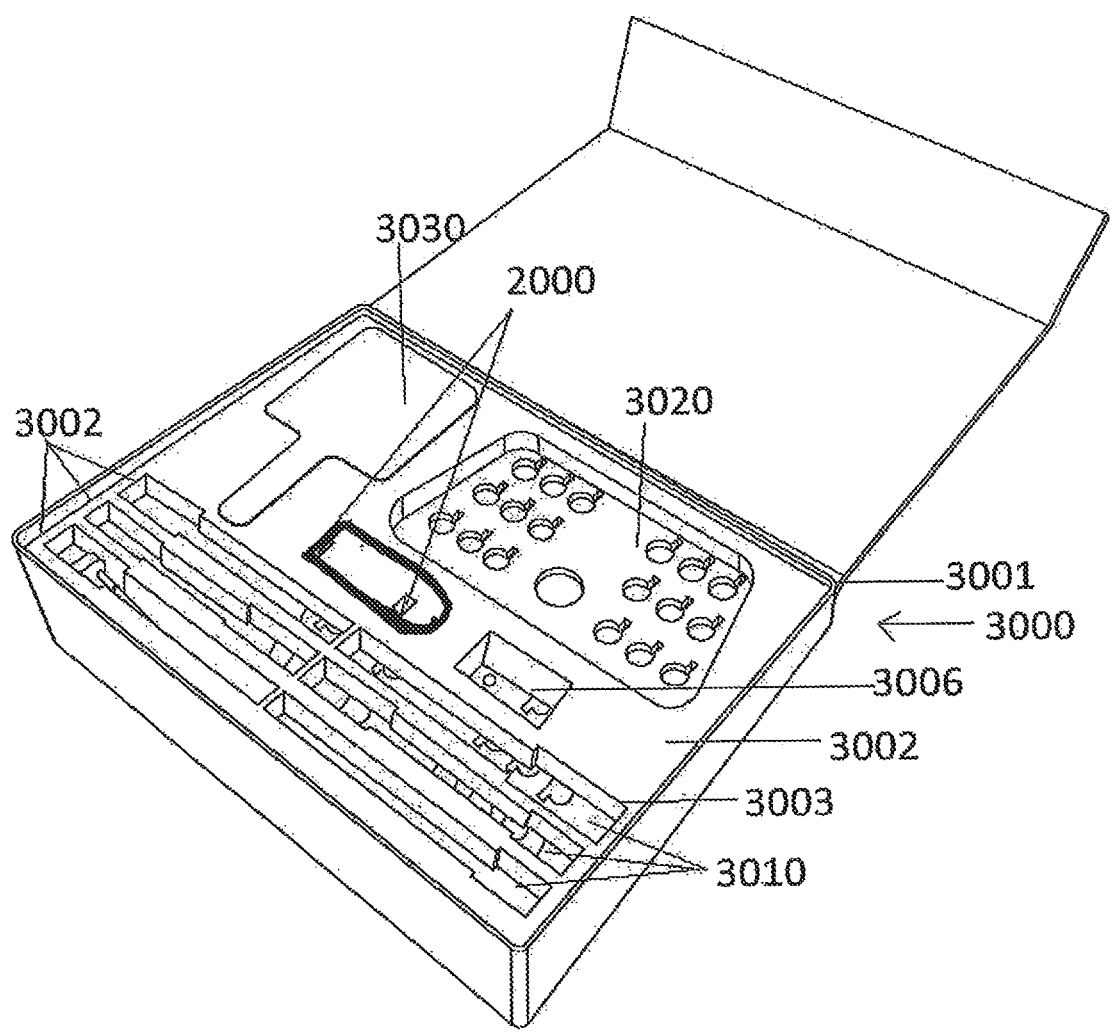
FIG. 25 is a perspective view of a kit associated with the present invention, including at least a storage tray, a plurality of cartridges and at least one mirror.
Figure 26:
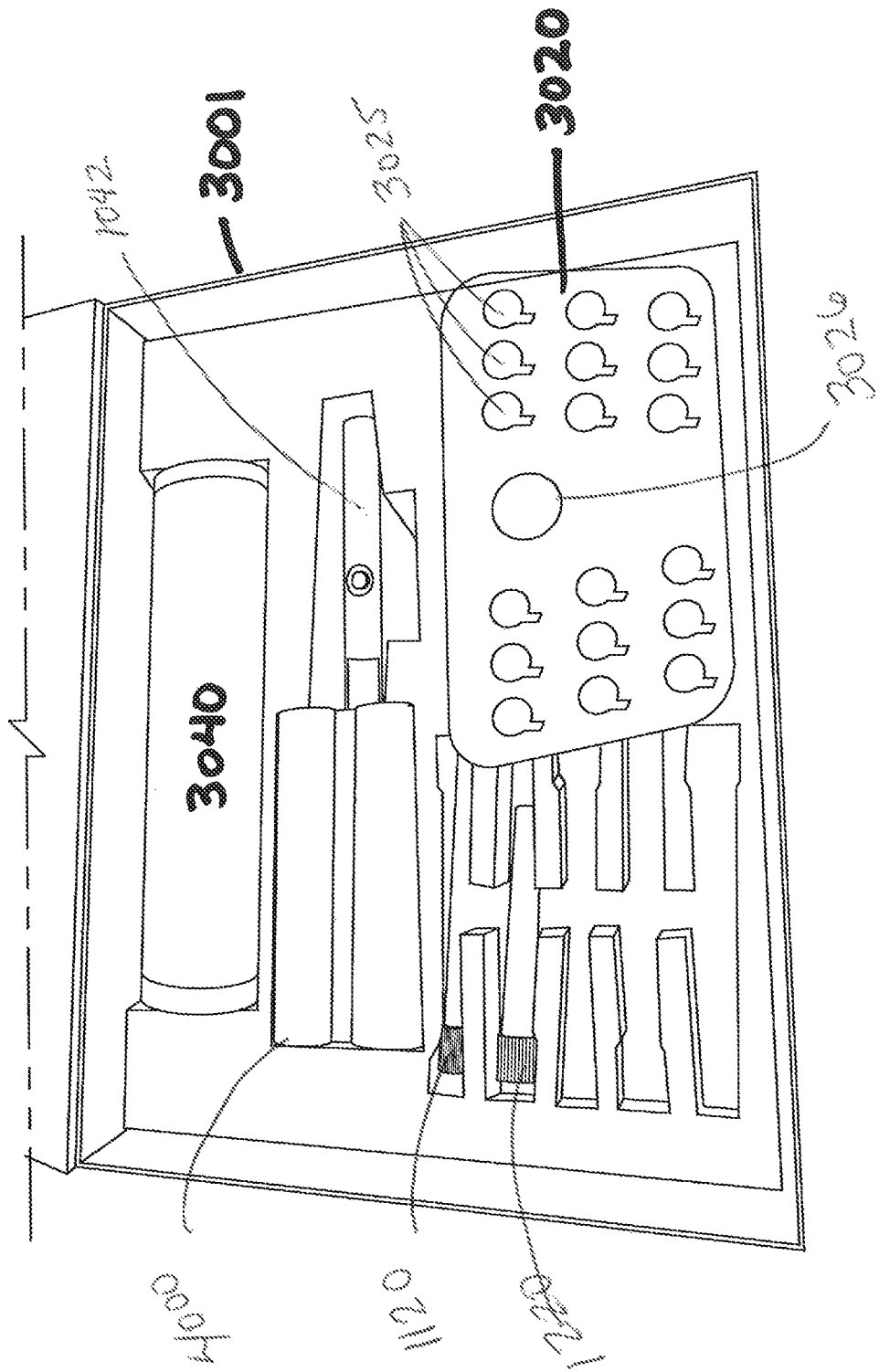
FIG. 26 is also a perspective view of a kit associated with the present invention, including at least the inventive device, one storage tray, a cape and a plurality of cartridges.

Referring now to FIGS. 25 and 26, the present invention is also directed to a kit 3000 that is particularly suited to accompany the inventive device 1000. The kit 3000 comprises a housing structure 3001 such as a box, for at least the device 1000 and a supply of cartridges or cartridge assemblies 3010. The housing structure 3001 may comprise one or more layers of foam material with cut-out sections for storing and displaying these and other components. As a non-limiting example, and as illustrated in FIG. 25, the kit 3000 and housing structure 3001 may comprise a layer of foam 3002 with cut-out portions 3003 sized and configured to store and display all of the following: a plurality of cartridge assemblies at 3010, such as cartridge assemblies 1120 and 1220 shown in FIGS. 16 and 17, a mirror attachment 2000 such as shown in FIG. 19-A, a storage tray 3020, and a hand held mirror 3030, and may include cut-out sections 3006 for other components, such as batteries, small rubber covers and/or replacement tips for the penetrating tip 1035 of movable member 1042. As another non-limiting example, and as shown in FIG. 25-A, the kit 3000 and box or other housing structure 3001 may comprise another layer of foam 3012 with cut-out portions sized and configured to store and display all of the following: the inventive device 1000, with or without a cover guard 4000, additional cartridge assemblies as at 3010 and/or a storage tray 3020, and a cape 3040. The cape 3040 is preferably made of a fabric or preferably silicone and is sized to be worn around the neck and shoulders of a user, in order to limit or prevent contact of hair building materials, whether dry materials, powders, wet materials, gels, and/or other hair care materials, including color, with the user's skin or clothing. Additionally, the cape 3040 associated with the kit 3000 can include a magnetic closure about the neck, and may be easily rolled up or folded and kept in the kit 3000, as shown, in an appropriately sized container.

Figure 22A:
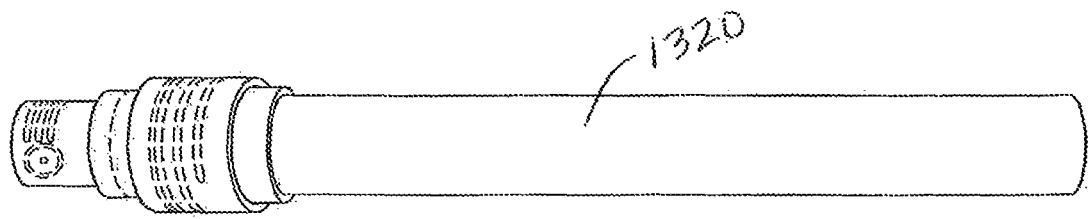
Figure 22B:
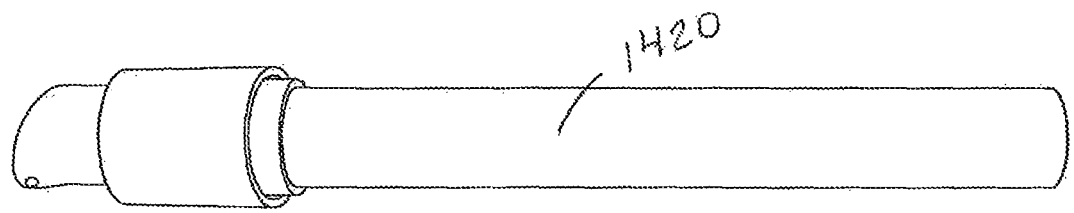

Referring now to FIGS. 26-A and 26-B, the storage tray 3020 or 3020' can be associated with the kit 3000 or alternatively, considered a stand-alone item for the inventive device and/or a plurality of cartridge assemblies. In at least one embodiment, the storage tray 3020 or 3020' is preferably formed from a lightweight and waterproof material. Storage tray 3020 can include a mounting element 3050, shown in FIGS. 27 and 27-A, to allow for mounting to a wall, whether in the vanity area of a bathroom or in a shower. In at least one embodiment, the storage tray 3020 for use in the shower is generally constructed from a water-resistant, rubber coated plastic or non-oxidizing metal. In the illustrated embodiments, the storage tray 3020 or 3020' includes a planar surface and comprises a plurality of slots or key hole like openings 3025, with each being structured and dimensioned to hold one of a plurality of supply cartridges, such as 1120 or 1220, as well as a larger opening 3026 for holding the handle 1042 of the device 1000, for convenient access and use wherever the storage tray 3020 is mounted. Furthermore, the storage tray 3020 may additionally house cartridges containing other hair care products, whether atomizer sprays or pump sprays such as shown in FIGS. 22A and 22B, spray soaps, shampoos, conditioners, and shampoo dyes. Also, and as set forth previously herein, one or more of the cartridges held by storage tray 3020 may be sonically activated bio-active cartridges. Further, it is within the spirit and scope of the present invention for the dimensions and/or overall shape of the storage tray to be modified such that it may be wider or longer or deeper than the illustrated embodiments.

The storage tray is shown in an alternative embodiment in FIGS. 26-B and 27-A. As illustrated therein, the storage tray 3020' also includes an opening 3026' structured and dimensioned for holding the handle 1042 of the device 1000, but can also receive within it and/or be replaced by a tube 3027 which is structured to include suitable electrical wiring and/or connectivity to an electrical power source, to serve as a recharging station for the battery or batteries within the handle 1042 of the device 1000. Additionally, storage tray 3020' can include an activation mechanism 3030 associated with a small housing 3028 and motor disposed on the storage tray 3020' as shown, which collectively, when activated, serve to apply a vibrating force to the storage tray 3020' and to any cartridges, atomizers, sprays, etc. carried thereon. This can be useful towards keeping the ingredients contained therein mixed and/or to limit settling of such contents.

Figure 28:
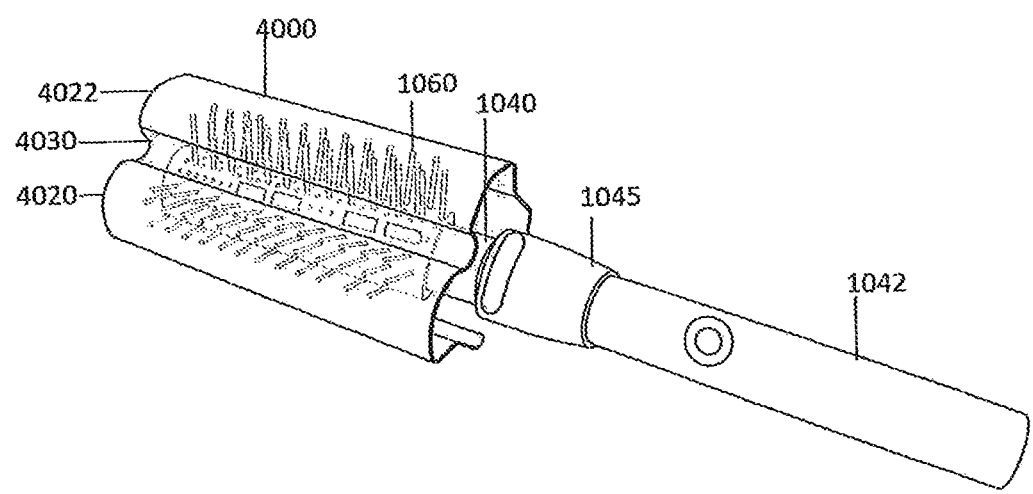
FIG. 28-A is an isolated view of a cover guard for the inventive device.
Figure 28:
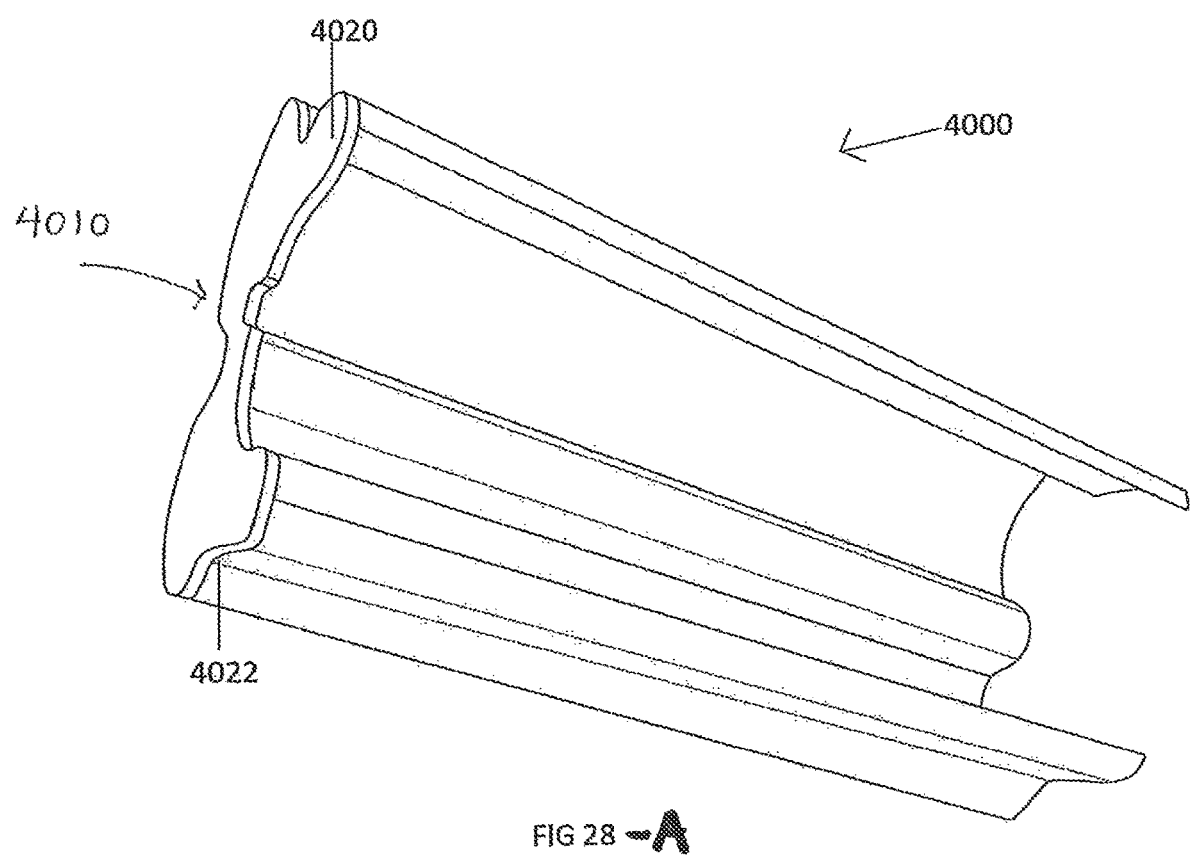
Figure 29:
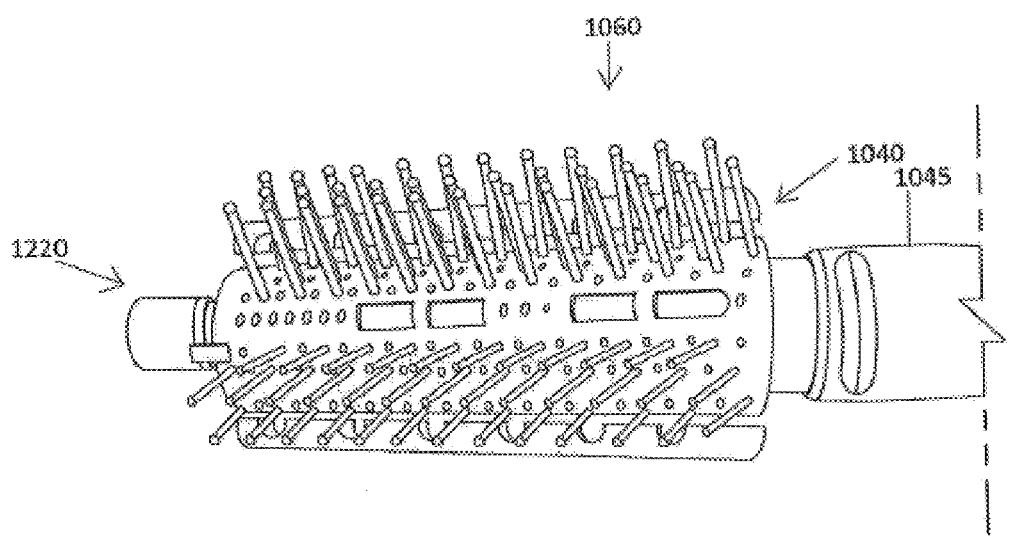
FIG. 29 is an isolated perspective view of the base, bristle assembly and an improved cartridge assembly associated with the inventive device.

With reference now to FIGS. 28-A and 28, the inventive device 1000 can also include a cover guard 4000. Preferably, the cover guard 4000 is sized and configured to be attached to the base 1040 of the device 1000 having a bristle assembly 1060 and further, is preferably also sized to extend both laterally, from one side thereof to the other, as well as longitudinally, from one end of the base 1040 to the other, and closely adjacent to the intermediate section 1045 of the handle 1042, (when the base 1040 is connected to a handle 1042). Additionally, the cover guard 4000 can include a distal end 4010 structured to cover the one or more openings, such as 1050' and 1072, of the base 1040, as shown in FIGS. 22 and 29. The cover guard 4000 can further include a particular shape in its cross section which includes a pair of arched sections joined together, and can be described as somewhat "m" shaped. That is, and as best shown in FIG. 29, the shape of the cover guard 4000 includes an arched section 4020 and 4022, each sized and configured to correspond to a lateral section of the bristle elements 1068 shown in FIG. 19 and a central segment 4030 that joins the arched sections 4020 and 4022 together and extends downwardly into covering relation over the aligned openings 1055 and 1065 associated with the base 1040 and bristle assembly 1060, respectively. As such, the cover guard 4000 can also be said to serve as a "spread guard," and to protect against any leakage of hair building materials when not in the process of being used or being prepared for use. Also, and while not shown in FIG. 29, the cover guard 4000 may be attached to the base 1040 and bristle assembly 1060 of the device 1000 while one or more auxiliary housings are attached thereto, although this is not required.

With reference now to FIG. 29, the inventive device 1000 is shown in assembled form. More specifically, the base 1040 and bristle assembly 1060 are assembled and a cartridge assembly, such as 1220 is inserted into the central housing 1050 of the base. In addition, the handle 1042 has been mounted to the base 1040, with the movable member thereof inserted into the tube 1221 (not shown) of the cartridge assembly 1220 and is operable to provide sonic oscillation to the hair building materials container therein.

Figures 30, 31:
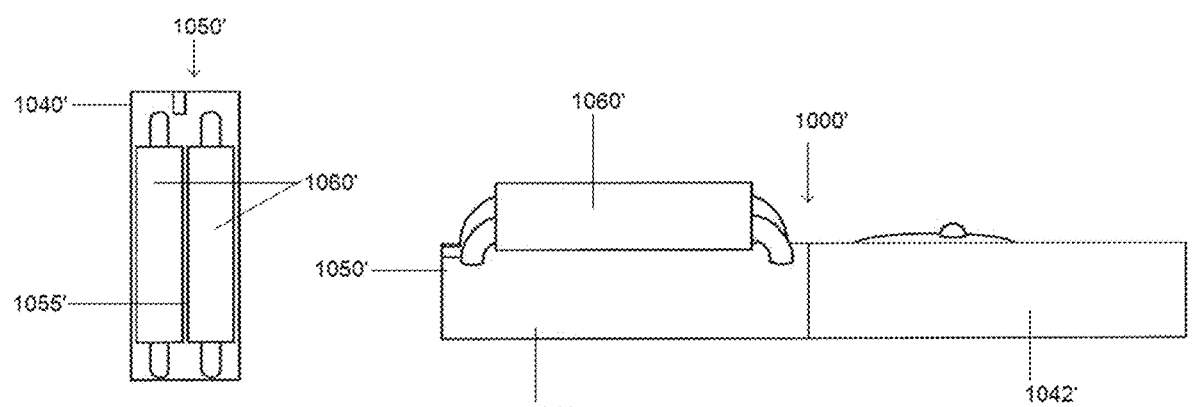
FIG. 30 is a side view of an alternative device for storing and dispensing hair building material which includes a plurality of rollers.
FIG. 31 is an isolated view of the roller assembly shown in FIG. 30.

Referring now to FIGS. 30-31, the inventive device 1000' is shown in an alternative embodiment. More specifically, the inventive device 1000' shown in FIG. 30 includes a base 1040' having a central housing 1050' and a plurality of rollers 1060', instead of a bristle assembly. In this illustrated embodiment, the base 1040' is also attachable to a handle 1042', such as that shown in FIG. 24 and having a movable member associated therewith. In addition, the central housing 1050' is sized and configured to receive a cartridge assembly therein, such as cartridge assembly 1120 shown in FIG. 16, or cartridge 1520 shown in FIG. 22-C, or others described herein. Thus, a selected cartridge assembly can be inserted within the central housing 1050' shown in FIGS. 30-31, and rotated within it. The central housing 1050' further includes an elongated slot 1055' disposed thereon in adjacent relation to the plurality of rollers and in fluid flow communicating relation with the interior of the central housing 1050' and, the contents of the cartridge assembly can therefore, pass through one or more apertures formed in the cartridge assembly and through the elongated slot 1055' of the central housing 1050' for dispersing onto the rollers 1060' during use, and application thereof to a selected treatment area. The illustrated embodiment shown in FIGS. 30-31 is adapted and suitable for storing and dispersing not only a desired hair care treatment onto the scalp, but preferably also other materials onto a person's skin, such as but not limited to a skin cream, moisturizer, body gel, soap, etc. Additionally, the plurality of rollers 1060' associated with this alternative device 1000' may comprise a pair of rubber rollers joined to the base 1040', and as best shown in FIG. 31, with each of these rollers preferably disposed in parallel relation to each other and further, being sized and configured to correspond generally, if not closely, to the length dimension of the base, such as but not limited to 120 mm.

Figure 32:
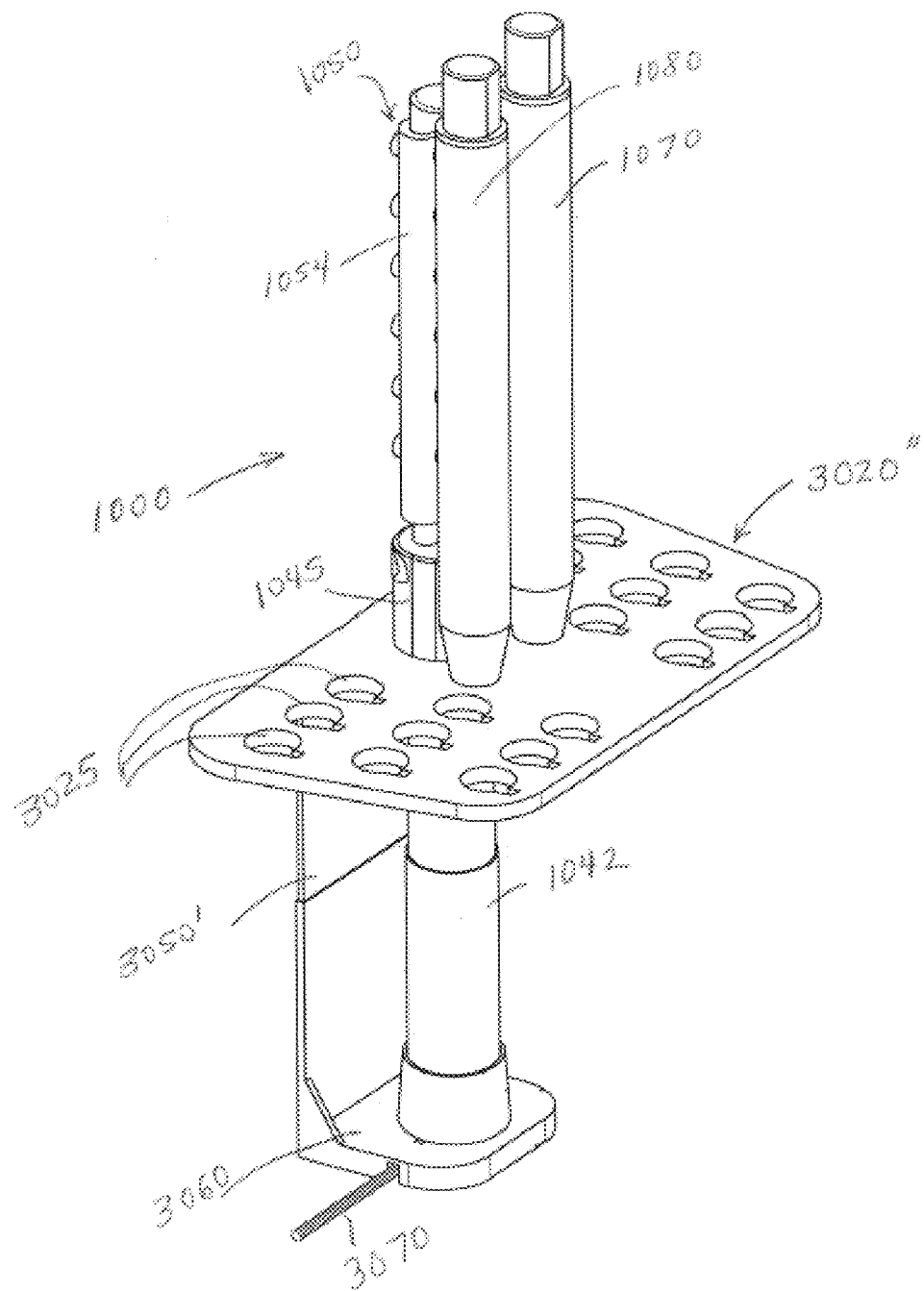
FIG. 32 is a front perspective view of a storage tray similar to that which shown in FIG. 26-B but illustrating the inventive device having a plurality of cartridges attached to it mounted into the storage tray for storage and/or recharging of any battery/batteries.
Figure 33:
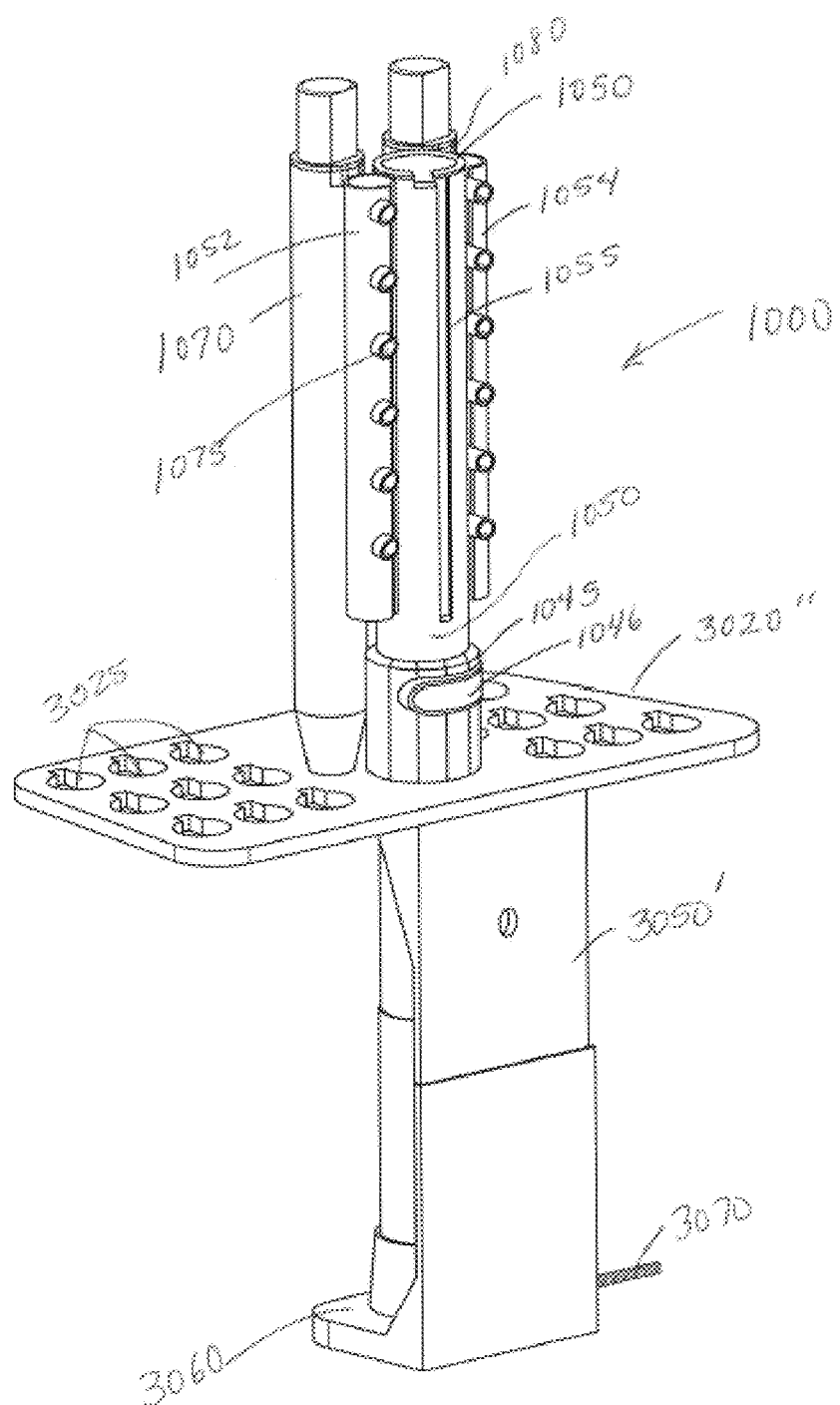
FIG. 33 is a rear perspective view of the storage tray and inventive device shown in FIG. 32.

With reference now to FIGS. 32-33, the inventive device 1000 is shown in assembled form, including an integral base and central housing 1050, attached to a handle 1042, and with a pair of auxiliary housings 1070, 1080 mounted thereon, each carrying a cartridge assembly within the hollow interior of each auxiliary housing, and in stored position on a storage tray 3020". As shown, in this embodiment, the storage tray 3020" has an extended mounting element 3050' with a lower section thereof structured to serve as a ledge or platform 3060 on which the handle 1042 of the device 1000 can stand, with power source connectivity 3070 so that any battery or batteries associated with the device 1000 can be recharged while the device 1000 is stored on the storage tray 3020".

Since many modifications, variations and changes in detail can be made to the described preferred embodiment of the invention, it is intended that all matters in the foregoing description and shown in the accompanying drawings be interpreted as illustrative and not in a limiting sense. As a non-limiting example, the bristle assemblies 60 or 1060 shown in the drawings could be made to assume other forms, or to be larger in size, including extending substantially or completely around a base of the device with a central housing. As another non-limiting example, one or more cartridge assemblies could assume the form of a tube or sleeve. Additionally, the inventive device should not be limited to dispersing hair building materials. Thus, the scope of the invention set forth in the foregoing description and shown in the accompanying drawings should be interpreted as illustrative, when taken in consideration with the following claims and their legal equivalents.

Now that the invention has been described,

What is claimed is:

1. A device for dispensing a hair building material, said device comprising:
   a base including a central housing,
   said base further including a first retaining channel formed along one longitudinal side and a second retaining channel formed along an oppositely disposed longitudinal side,
   said central housing defined by a body having at least one open end and a hollow interior sized and configured to carry a first supply of hair building material therein,
   said central housing including at least one elongated opening formed in said body sized and configured for passage of said first supply of hair building material therethrough,
   a bristle assembly including an at least partially flexible mat and a plurality of bristle elements,
   said at least partially flexible mat including a mating structure formed on each longitudinal side thereof, each mating structure being sized and configured to be removably joined to either said first retaining channel or said second retaining channel of said base, with said at least partially flexible mat also being sized and configured to extend substantially across an exposed surface of said base, including said central housing,
   said at least partially flexible mat further including at least one opening formed therein adjacent to said base and in fluid flow communication with said opening formed in said body of said central housing, and further, in fluid flow communication with said plurality of bristle elements,
   said plurality of bristle elements structured and disposed to dispense said first supply of hair building material onto a person's scalp,
   a handle connected to said base, said handle including a movable member, a motor and a power source coupled thereto,
   said movable member disposed within said central housing in connected relation to said first supply of hair building material when said handle is connected to said base, and
   said movable member structured to selectively apply at least a vibratory force to said first supply of the hair building material.

2. The device as recited in claim 1 wherein said handle is removably connected to said base.

3. The device as recited in claim 1 wherein said elongated opening of said central housing and said base, together with said at least one opening in said flexible mat define a first fluid flow path for said first supply of hair building material for delivery to said plurality of bristle elements.

4. The device as recited in claim 3 wherein said handle is connected in driving relation to at least said movable member, and is further structured to exert a vibratory force on said plurality of bristle elements, said plurality of bristle elements movable relative to one another and said first supply of hair building material delivered thereto.

5. The device as recited in claim 1 wherein said first supply of hair building material is in the form of a gel and wherein said vibrating force is sufficient to at least partially liquefy said first supply of hair building material.

6. The device as recited in claim 5, further including a first cartridge assembly carrying said first supply of hair building material and an access opening formed therein, said first cartridge assembly being sized and configured to be disposed in and rotatable within said central housing for alignment of said access opening with said elongated opening of said central housing, thereby further defining said first fluid flow path.

7. The device as recited in claim 6, wherein said movable member is disposed within said central housing in connected relation to said first cartridge assembly disposed therein; said movable member capable of exerting a vibrating force on said cartridge assembly and said first supply of hair building material contained therein.

8. The device as recited in claim 6 wherein said first cartridge assembly includes a first chamber and a second chamber, said first chamber carrying said first supply of hair building material in a wet form, and said second chamber carrying said second supply of hair building material in a dry form.

9. The device as recited in claim 6 wherein at least a portion of said first cartridge assembly is made from a bio-degradable material.

10. The device as recited in claim 9 wherein said bio-degradable material comprises any material capable of interacting with any of said hair building materials.

11. The device as recited in claim 9 wherein said bio-degradable material is polylactic acid.

12. The device as recited in claim 11 wherein said bio-degradable material further comprises polybutylene adipate terephthalate.

13. The device as recited in claim 9 wherein at least a portion of said hair building material in said dry form is in a powder form and selected from the group comprising: Activated Charcoal, Potato Starch, #2 baking soda, sodium acid pyrophosphate and Amla Powder.

14. The device as recited in claim 1 wherein said first retaining channel and said second retaining channel of said base each include a plurality of openings, each of said plurality of openings configured for passage of a second supply of hair building material therethrough.

15. The device as recited in claim 8 further comprising a first auxiliary housing mounted on said base, said first auxiliary housing sized and configured to carry said second supply of hair building material.

16. The device as recited in claim 15, wherein said first auxiliary housing includes a peg structure having a plurality of openings formed therein and in communication with said second supply of hair building material, said first auxiliary housing mounted on said first retaining channel of said base with said peg structure received within said plurality of openings of said first retaining channel.

17. The device as recited in claim 16 wherein said plurality of openings of said peg structure and said plurality of openings of said retaining channel define a second fluid flow path for said second supply of hair building material, for delivery to said plurality of bristle elements.

18. The device as recited in claim 17, wherein said second fluid flow path is disposed in spaced apart and generally parallel relation to said first fluid flow path.

19. The device as recited in claim 18 further comprising a second cartridge assembly carrying said second supply of hair building material, and having at least one access opening formed therein.

20. The device as recited in claim 19, wherein said second cartridge assembly is sized and configured to be received in and rotatable within said first auxiliary structure for alignment of said access opening with said plurality of openings in said peg structures, thereby further defining said second fluid flow path.

21. The device as recited in claim 20 further comprising a second auxiliary housing mounted on said base, said second auxiliary housing sized and configured to carry a different supply of hair care material.

22. The device as recited in claim 1 wherein at least a portion of said hair building materials is selected from the group comprising: water, glycerin, carbomer, polysorbate 20, PVP, Aminomethyl Propanol, Methylparaben, Fragrance, Glyceryl, Polymethacrylate, Rahnella and Soy Protein Ferment, Propylene Glycol, Peg 8, Palmitoyl, Tripeptide-1, Keratin Amino Acides, Panthenyl Ethyl, Ether, Diazolidinyl, Urea, Potassium Sorbate, Tetrasodium EDTA, Methylchloroisothiazolinone, Methylsothiazolinone, *Aloe ferox, Aloe baredensis*, Decolorized *Aloe barbadensis*, Lemon, Cotton Cellulose, Iron Oxides, Carbon Dioxide ($CO_2$), Phenoxyethanol, Capryl Glycol, Sorbic Acid, Apple Cider Vinegar, Citric acid, Arrowroot Powder, Xanthan Gum, Keratin protein, Dimethicone, Coconut Oil, Tea tree oil, Rosemary Oil, Argan Oil, Black Castor Oil, Maltodextrin, Epsom Salt, Himalaya Salt, Silk Amino Acids, Caffeine, Cannabidiol (CBD), Hemp Extract, whole oranges, whole cucumbers, soybean, sugarcane, hyaluronic acid, lactobacillus, lactic acid, polyquaternium-4, sodium benzoate, witch hazel, Pantenol B 5, Vegetable emulsifying wax, Ethelhexyl stearate, I Ethelhexyl palmitate, hydrogenated olive oil unsaponifiables and/or Potassium cocoate.

23. The device as recited in claim 1 further comprising a mirror assembly removably connected to said base and disposable between a closed position in substantially parallel relation to said base and an open position while connected to said base to permit viewing of the mirror during use of the base and bristle assembly.

24. The device as recited in claim 1 further comprising a cover guard removably attached to said base in covering relation to said bristle assembly.

25. A device for carrying and dispensing material onto a person's hair comprising:
- a base including a central housing,
  - said central housing having at least one open end and a hollow interior sized and configured to carry a cartridge with at least a first supply of a hair care material therein,
  - said central housing including at least one additional opening sized and configured to allow passage of a portion of said first supply of the hair care material therethrough,
- a bristle assembly including a plurality of bristle elements,
  - said bristle assembly removably joined to said base and including a plurality of openings formed therein adjacent to said base and in fluid flow communication with said at least one additional opening formed in said central housing, and configured to allow for fluid flow communication of said first supply of the hair care material along a first fluid flow path for delivery to said plurality of bristle elements,
- at least one auxiliary housing removably connected to said base and disposed in substantially parallel relation to said base, said auxiliary housing carrying a second supply of a hair care material and having at least one opening sized and configured to allow passage of a portion of said second supply of the hair care material therethrough,
  - said at least one opening of said auxiliary housing disposed in fluid flow communication with said bristle assembly and in spaced apart relation to said at least one opening formed in said central housing, to define a second fluid flow path for delivery to said plurality of bristle elements,
- said plurality of bristle elements disposed in fluid communicating relation to both said first supply of the hair care material and said second supply of the hair care material, and structured to deliver substantially concurrently to a person's scalp hair both said first and second supply of the hair care material for blending at said plurality of bristle elements,
- a handle connected to said base, said handle including a movable member, a motor and a power source coupled thereto,
- said movable member disposed within said central housing in connected relation to said first supply of hair building material when said handle is connected to said base, and
- said movable member structured to selectively apply a vibratory force to said first supply of the hair building material.

26. The device as recited in claim 25 wherein said handle is removably connected to said base.

27. The device as recited in claim 25 further comprising a cartridge assembly disposed within said central housing, said cartridge assembly including a first chamber for carrying a first supply of hair building material, a second chamber for carrying a different supply of hair building material, and a plurality of openings in fluid flow communication with said additional opening in said central housing.

28. The device as recited in claim 25 further comprising a second auxiliary removably connected to said base and disposed in substantially parallel relation to both said base and said first auxiliary housing, said second auxiliary housing carrying an additional supply of a hair care material and having at least one opening sized and configured to allow passage of a portion of said additional supply of the hair care material therethrough.

29. The device as recited in claim 28 further comprising a cartridge assembly disposed within said second auxiliary housing, said cartridge assembly carrying said additional supply of hair care material and means for spraying said additional supply of hair care material for application thereof.

30. A device for carrying and dispensing material onto a person's hair comprising:
- a base including a central housing,
  - said central housing having at least one open end and a hollow interior sized and configured to carry a cartridge with at least a first supply of a hair care material therein,
  - said central housing including at least one additional opening sized and configured to allow passage of a portion of said first supply of the hair care material therethrough, a bristle assembly including a plurality of bristle elements, said bristle assembly removably joined to said base and including a plurality of openings formed therein adjacent to said base and in fluid flow communication with said at least one additional opening formed in said central housing, and configured to allow for fluid flow communication of said first supply of the hair care material along a first fluid flow path for delivery to said plurality of bristle elements, at least one auxiliary housing removably connected to said base and disposed in substantially parallel relation to said base, said auxiliary housing carrying a second supply of a hair care material and having at least one opening sized and configured to allow passage of a portion of said second supply of the hair care material therethrough, said at least one opening of said auxiliary housing disposed in fluid flow communication with said bristle assembly and in spaced apart relation to said at least one opening formed in said central housing, to define a second fluid flow path for delivery to said plurality of bristle elements, said at least one auxiliary housing further including a plurality of peg structures, each of said peg structures having an opening at a distal end thereof configured to allow passage said second supply of hair care material therethrough, and mountable onto one of either said first retaining channel or said second retaining channel of said base, said plurality of bristle elements disposed in fluid communicating relation to both said first supply of the hair care material and said second supply of the hair care material, and structured to deliver substantially concurrently to a person's scalp hair both said first and second supply of the hair care material for blending at said plurality of bristle elements, and said base further including a first retaining channel formed along one longitudinal side thereof and a second retaining channel formed along an oppositely disposed longitudinal side thereof, with each of said first and second retaining channels including a plurality of openings formed therein.

31. The device as recited in claim 30 further comprising a cartridge assembly disposed within said auxiliary housing, said cartridge assembly including a plurality of slots formed therein and carrying a supply of hair care material.

32. A device for carrying and dispensing material onto a person's hair comprising:

a base including a central housing, said central housing having at least one open end and a hollow interior sized and configured to carry a cartridge with at least a first supply of a hair care material therein, said central housing including at least one additional opening sized and configured to allow passage of a portion of said first supply of the hair care material therethrough, a bristle assembly including a plurality of bristle elements, said bristle assembly removably joined to said base and including a plurality of openings formed therein adjacent to said base and in fluid flow communication with said at least one additional opening formed in said central housing, and configured to allow for fluid flow communication of said first supply of the hair care material along a first fluid flow path for delivery to said plurality of bristle elements, at least one auxiliary housing removably connected to said base and disposed in substantially parallel relation to said base, said auxiliary housing carrying a second supply of a hair care material and having at least one opening sized and configured to allow passage of a portion of said second supply of the hair care material therethrough, said at least one opening of said auxiliary housing disposed in fluid flow communication with said bristle assembly and in spaced apart relation to said at least one opening formed in said central housing, to define a second fluid flow path for delivery to said plurality of bristle elements, said plurality of bristle elements disposed in fluid communicating relation to both said first supply of the hair care material and said second supply of the hair care material, and structured to deliver substantially concurrently to a person's scalp hair both said first and second supply of the hair care material for blending at said plurality of bristle elements, and said auxiliary housing further including a plurality of peg structures, each of said plurality of peg structures having an opening at a distal end thereof configured to allow passage said second supply of hair care material therethrough.

* * * * *